United States Patent [19]

Eidenschink et al.

[11] Patent Number: 4,985,583
[45] Date of Patent: Jan. 15, 1991

[54] CYCLOHEXANE DERIVATIVES

[75] Inventors: Rudolf Eidenschink, Münster; Joachim Krause, Dieburg; Andreas Wächtler, Griesheim; Reinhard Hittich, Modautal; Bernhard Scheuble, Alsbach; Georg Weber, Erzhausen; Hans-Adolf Kurmeier, Seeheim-Jugenheim, all of Fed. Rep. of Germany

[73] Assignee: Merck Patent Gesellschaft mit beschränkter Haftung, Darmstadt, Fed. Rep. of Germany

[21] Appl. No.: 35,548

[22] Filed: Apr. 7, 1987

Related U.S. Application Data

[63] Continuation of Ser. No. 705,811, Feb. 26, 1985, abandoned, which is a continuation-in-part of Ser. No. 526,927, Aug. 26, 1983, Pat. No. 4,510,069.

[30] Foreign Application Priority Data

Aug. 26, 1982 [DE] Fed. Rep. of Germany ....... 3231707
Jun. 3, 1983 [DE] Fed. Rep. of Germany ....... 3320024
Feb. 27, 1984 [DE] Fed. Rep. of Germany ....... 3407013

[51] Int. Cl.$^5$ .................... C07C 255/00; C09K 19/52
[52] U.S. Cl. ........................... 558/431; 252/299.01; 252/299.61; 252/299.63; 350/350 R; 558/426; 544/241; 544/242; 544/295; 544/296; 544/298; 544/336; 544/357; 546/186; 546/187; 546/189; 546/190; 546/191; 546/192; 546/193; 546/194; 546/255; 546/256; 546/275; 546/276; 546/286; 546/287
[58] Field of Search ........... 252/299.01, 299.5, 299.61, 252/299.62, 299.63; 350/350 R; 558/426, 431; 544/241, 242, 295, 296, 298, 336, 357; 546/186, 187, 189, 190, 191, 192, 193, 194, 255, 256, 275, 276, 286, 287

[56] References Cited

U.S. PATENT DOCUMENTS

| | | | |
|---|---|---|---|
| 4,181,625 | 1/1980 | Eidenschink et al. | 252/299.63 |
| 4,510,069 | 4/1985 | Eidenschink et al. | 252/299.63 |
| 4,629,581 | 12/1986 | Petrzilka et al. | 252/299.63 |
| 4,659,499 | 4/1987 | Ferrato | 252/299.63 |

FOREIGN PATENT DOCUMENTS 3328638 2/1985 Fed. Rep. of Germany .

Primary Examiner—Robert L. Stoll
Assistant Examiner—Richard Treanor
Attorney, Agent, or Firm—Millen, White & Zelano

[57] ABSTRACT

New cyclohexane derivatives of the formula I $$R^1-A^1-Z^1-A^2-R^2 \qquad I$$

wherein $R^1$ and $R^2$ are each H, an unsubstituted or substituted alkyl group with 1–15 C atoms, it also being possible for one or two non-adjacent $CH_2$ groups to be replaced by at least one grouping from the group comprising —O—, —CO—, —O—CO—, —CO—O—, —C≡C—, —CH=CH—, —S—, —SO— and —SO$_2$—, F, Cl, Br, CN or $R^3-(A^3)_p-Z^2-$, $A^1$ is —A—, —A$^4$—Z$^3$—A— or —A—Z$^3$—A$^4$—, A is a 1,4-cyclohexylene group which is substituted in the 1- and/or 4-position by unsubstituted or substituted alkyl or fluorinated alkyl with in each case 1–5 C atoms, it also being possible for one or two non-adjacent $CH_2$ groups to be replaced by one grouping from the group comprising —O—, —CO—, —O—CO—, —CO—O—, —C≡C—, —CH=CH—, —S—, —SO— and —SO$_2$—, or by F, Cl, Br, CN and/or —CHO, and which can carry 1 or 2 further substituents, $A^2$, $A^3$ and $A^4$ in each case denote 1,4-phenylene which is unsubstituted or substituted by one or two F and/or Cl atoms and/or $CH_3$ groups and/or CN groups, it also being possible for one or two CH groups to be replaced by N atoms, 1,4-cyclohexylene, it also being possible for one or two non-adjacent $CH_2$ groups to be replaced by O atoms, 1,4-cyclo-1-enyl, 1,3-dithiane-2,5-diyl, piperidine-1,4-diyl, 1,4-bicyclo(2,2,2)-octylene, unsubstituted or CN-substituted decahydronaphthalene-2,6-diyl or 1,2,3,4-tetrahydronaphthalene-2,6-diyl or —A—, $Z^1$, $Z^2$ and $Z^3$ each are —CO—O—, —O—CO—, —OCH$_2$—, —CH$_2$O—, —CH$_2$CH$_2$—, substituted ethylene or a single bond, $R^3$ is H, an unsubstituted or substituted alkyl group with 1–15 C atoms, it also being possible for one or two non-adjacent $CH_2$ groups to be replaced by a grouping from the group comprising —O—, —CO—, —O—CO—, —CO—O—, —C≡C—, —CH=CH—, —S—, —SO— and —SO$_2$—, F, Cl, Br or CN and p is 1 or 2, and, if p=2, the groups $A^3$ can be identical or different, and the acid addition salts of the basic compounds of this type, are suitable for use as components of liquid crystal dielectrics.

33 Claims, No Drawings

CYCLOHEXANE DERIVATIVES

CROSS-REFERENCE TO RELATED APPLICATION

This is a continuation of application Ser. No. 705,811 filed Feb. 26, 1985 now abandoned, which is a continuation-in-part of U.S. Patents Application Ser. No. 526,927 of Aug. 26, 1983, now U.S. Pat. No. 4,510,069 and which disclosure is incorporated by reference herein.

This invention relates to new compounds having valuable liquid crystalline properties.

SUMMARY OF THE INVENTION

It is an object of this invention to provide new stable liquid crystal or mesogenic compounds which are suitable as components of liquid crystal phases.

Upon further study of the specification and appended claims, further objects and advantages of this invention will become apparent to those skilled in the art.

These objects have been achieved by providing cyclohexane derivatives of the formula I $$R^1—A^1—Z^1—A^2—R^2 \quad I$$

wherein $R^1$ and $R^2$ are each H, an unsubstituted or substituted alkyl group with 1-15 C atoms, it also being possible for one or two non-adjacent $CH_2$ groups to be replaced by at least one grouping from the group comprising —O—, —CO—, —O—CO—, —CO—O—, —C≡C—, —CH=CH—, —S—, —SO— and —$SO_2$—, F, Cl, Br, CN or $R^3$—$(A^3)_p$—$Z^2$—, $A^1$ is —A—, —$A^4$—$Z^3$—A— or —A—$Z^3$—$A^4$—, A is a 1,4-cyclohexylene group which is substituted in the 1- and/or 4-position by unsubstituted or substituted alkyl or fluorinated alkyl with in each case 1-5 C atoms, it also being possible for one or two non-adjacent $CH_2$ groups to be replaced by one grouping from the group comprising —O—, —CO—, —O—CO—, —CO—O—, —C≡C—, —S—, —SO— and —$SO_2$—, or by F, Cl, Br, CN and/or —CHO, and which can carry 1 or 2 further substituents, $A^{2,} A^3$ in each case are 1,4-phenylene which is unsubstituted unsubstituted or substituted by one or two F and/or Cl atoms and/or $CH_3$ groups and/or CN groups, it also being possible for one or two CH groups to be replaced by N atoms, 1,4-cyclohexylene, it also being possible for one or two non-adjacent $CH_2$ groups to be replaced by O atoms. 1,4-cyclohexylene 1-enyl, 1,3-dithiane-2,5-diyl, piperidine-1,4-diyl, 1,4-bicyclo(2,2,2)-octylene, unsubstituted or CN-substituted decahydronaphthalene-2,6-diyl or 1,2,3,4-tetrahydronaphthalene-2,6-diyl or —A—, $Z^{1,} Z^2$ each are —CO—O—, —O—CO—, —$OCH_2$—, —$CH_2$—, and $Z^3$ —$CH_2CH_2$—, substituted ethylene or a single bond, $R^3$ is H, an unsubstituted or substituted alkyl group with 1-15 C atoms, it also being possible for one or two non-adjacent $CH_2$ groups to be replaced by a grouping from the group comprising —O—, —CO—, —O—CO—, —CO—O—, —C≡C—, —CH=CH—, —S—, —SO— and —$SO_2$—, F, Cl, Br or CN and p is 1 or 2, and, if p=2, the groups $A^3$ can be identical or different, and the acid addition salts of the basic compounds of this type.

DETAILED DISCUSSION

For simplicity, in the following text Phe is an unsubstituted or substituted 1,4-phenylene group, Cy is a 1,4-cyclohexylene group, Dio is a 1,3-dioxane-2,5-diyl group, Dit is a 1,3-dithiane-2,5-diyl group, Bi is a bicyclo(2,2,2)-octylene group, Pip is a piperidine-1,4diyl group, Pyn is a pyridazine-3,6-diyl group and Pyr is a pyrimidine-2,5-diyl group.

The compounds of the formula I can be used as components of liquid crystal phases, in particular for displays which are based on the principle of the twisted cell, the guest/host effect, the effect of deformation of aligned phases or the effect of dynamic scattering.

It has been found that the compounds of the formula I are outstandingly suitable as components of liquid crystal phases. In particular, stable liquid crystal phases with highly negative dielectric anisotropy and thus a smaller threshold or control voltage of electrooptical effects, very low optical anisotropy and comparatively low viscosity can be prepared with the aid of these compounds.

Surprisingly, it has been found that when compounds of the formula I are added to mixtures with positive dielectric anisotropy, even the addition of relatively large amounts (for example of 30%) only insignificantly increases the threshold voltage. At the same time, a completely unexpected substantial improvement in the steepness of the characteristic line of the mixture occurs, so that compounds of type I are particularly advantageously suitable substances for the preparation of liquid crystal mixtures with a steep characteristic line. They thus enable the development of highly multiplyable mixtures of very small optical anisotropy, with which a rotating cell, in particular, can be operated in the first transmission minimum in accordance with the Gooch-Tarry method. This results in a very small dependency of the contrast on the observation angle.

By providing the compounds of the formula I, the range of liquid crystal substances which are suitable, from various technological viewpoints, for the preparation of nematic mixtures is also quite generally considerably increased.

The compounds of the formula I have a wide range of application. Depending on the choice of the substituents, these compounds can be used as base materials from which liquid crystal phases are predominantly composed; however, it is also possible to add compounds of the formula I to liquid crystal base materials from other classes of compounds, for example in order to reduce the dielectric and/or optical anisotropy of such a dielectric. The compounds of the formula I are furthermore suitable as intermediates for the preparation of other substances which can be used as constituents of liquid crystal phases.

The compounds of the formula I are colorless in the pure state and form liquid crystal mesophases in a temperature range which is advantageously located for electrooptical use. They are very stable towards chemicals, heat and light.

The invention thus relates to the compounds of the formula I and to a process for their preparation, characterized in that a compound which otherwise corresponds to the formula I but contains one or more reducible groups and/or C-C bonds instead of H atoms is treated with a reducing agent, or in that a compound of the formula HX (wherein X is F, Cl, Br or CN) is added onto a compound which otherwise corresponds to the formula I but, instead of the radical A, contains a 1-cyclohexene-1,4-diyl group which can carry 1 or 2 further F, Cl or. Br atoms and/or CN groups, or in that, to prepare esters of the formula I (wherein $R^1$ and/or $R^2$ are an alkyl group in which one or two $CH_2$ groups are replaced by a carboxyl group, and/or wherein $Z^1$ and/or $Z^2$ and/or $Z^3$ are —CO—O— or O——CO—), a corresponding carboxylic acid or one of its reactive derivatives is reacted with a corresponding alcohol or one of its reactive derivatives, or in that, to prepare dioxane derivatives derivatives of the formula I (wherein $A^2$ and/or $A^3$ and/or $A^4$ are 1,3-dioxane-2,5-diyl or 1,3-dithiane-2,5-diyl), a corresponding aldehyde or one of its reactive derivatives is reacted with a corresponding diol, or in that, to prepare nitriles of the formula I (wherein $R^1$ and/or $R^2$ denote CN and/or wherein A and/or $A_2$ and/or $A^3$ and/or $A^4$ are substituted by at least one CN group), a corresponding carboxylic acid amide is dehydrated or a corresponding carboxylic acid halide is reacted with sulfamide, or in that, to prepare nitriles of the formula I (wherein A is a 1,4-cyclohexylene group which is substituted in the 1- or 4-position by CN), a corresponding acetonitrile is reacted with a corresponding 3-substituted 1,5-dihalogenopentane or 1,5-pentanediol or one of their reactive derivatives, or in that, to prepare nitriles of the formula I (wherein A is 1,4-cyclohexylene group which is substituted in the 1- or 4position by CN and can additionally carry 1 or 2 further substituents), a corresponding 4-substituted cyclohexanecarbonitrile is reacted with a corresponding halogen compound or hydroxy compound or one of their reactive derivatives, or in that, to prepare compounds of the formula I (wherein A is a 1,4-cyclohexylene group which is substituted in the 1- or 4-position by an alkoxycarbonyl group with 1 to 4 C atoms and which can additionally carry 1 or 2 further substituents), a corresponding 4-substituted cyclohexanecarboxylic acid ester is reacted with a corresponding halogen compound or hydroxy compound or one of their reactive derivatives, or in that, to prepare aldehydes of the formula I (wherein A is a 1,4-cyclohexylene group which is substituted in the 1- or 4-position by —CHO and which can additionally carry 1 or 2 further substituents), a corresponding nitrile of the formula I is reduced, or in that, to prepare compounds of the formula I (wherein A is a 1,4-cyclohexylene group which is substituted in the 1- or 4-position by —$CH_3$ and which can additionally carry 1 or 2 further substituents), a corresponding aldehyde is reduced, or in that, to prepare compounds of the formula I (wherein A is a 1,4-cyclohexylene group which is substituted in the 1- or 4-position by F and can additionally carry 1 or 2 further substituents), a corresponding hydroxy or halogen compound is treated with a fluorinating agent, or in that, to prepare ethers of the formula I (wherein $R^1$ and/or $R^2$ are an alkyl group, in which one or two $CH_2$ groups are replaced by O atoms, and/or $Z^1$ and/or $Z^2$ and/or $Z^3$ are an —$OCH_2$— or —$CH_2O$—group), a corresponding hydroxy compound is etherified, or in that, to prepare compounds of the formula I wherein $R^1$ and/or $R^2$ are an alkyl group, in which one or two $CH_2$ groups are replaced by —SO— or —$SO_2$—, a corresponding compound wherein $R^1$ and/or $R^2$ are SR or SOR is oxidized, or in that, to prepare compounds of the formula I (wherein A is a 1,4-cyclohexylene group which is substituted in the 1- or 4-position by an alkyl group, wherein one or two non-adjacent $CH_2$ groups are replaced by —SO— or —$SO_2$—, and which can additionally carry 1 or 2 further substituents), a corresponding thio or sulfinyl compound is oxidized, or in that, to prepare compounds of the formula I which contain $CF_3$ groups, a corresponding carboxylic acid is reacted with $SF_4$, and/or in that, if appropriate, a chlorine or bromine compound of the formula I (wherein $R^1$ and/or $R^2$ denote Cl or Br and/or wherein A is substituted by at least one chlorine or bromine atom and/or $A^2$ and/or $A^3$ and/or $A^4$ are substituted by at least one chlorine atom) is reacted with a cyanide, and/or in that, if appropriate, a base of the formula I is converted into one of its acid addition salts by treatment with an acid, or in that, if appropriate, a compound of the formula I is liberated from one of its acid addition salts by treatment with a base.

The invention furthermore relates to the use of compounds of the formula I as components of liquid crystal phases. The invention also relates to liquid crystal phases containing at least one compound of the formula I, and to liquid crystal display elements, in particular electrooptical display elements, containing such phases.

Above and below, $R^1$, $R^2$, $R^3$, $A^1$, $A^2$, $A^3$, $A^4$, A, $Z^1$, $Z^2$, $Z^3$, X and p have the meaning given, unless expressly indicated otherwise.

The compounds of the formula I accordingly include, in particular, compounds of the part formulae I1 and I2 (with two rings), I3-I20 (with 3 rings), I21-I71 (with 4 rings) and I72-I94 (with 5 rings):

| | |
|---|---|
| $R^1$—A—$A^2$—$R^2$ | I1 |
| $R^1$—A—$Z^1$—$A^2$—$R^2$ | I2 |
| $R^1$—$A^4$—A—$A^2$—$R^2$ | I3 |
| $R^1$—A—$A^4$—$A^2$—$R^2$ | I4 |
| $R^3$—$A^3$—A—$A^2$—$R^2$ | I5 |
| $R^1$—A—$A^2$—$A^3$—$R^3$ | I6 |
| $R^1$—$A^4$—$Z^3$—A—$A^2$—$R^2$ | I7 |
| $R^1$—A—$Z^3$—$A^4$—$A^2$—$R^2$ | I8 |
| $R^1$—A—$Z^1$—$A^2$—$A^3$—$R^3$ | I9 |
| $R^1$—$A^4$—$Z^3$—A—$A^2$—$R^2$ | I10 |
| $R^1$—A—$Z^3$—$A^4$—$A^2$—$R^2$ | I11 |
| $R^1$—$A^4$—A—$Z^1$—$A^2$—$R^2$ | I12 |
| $R^1$—A—$A^4$—$Z^1$—$A^2$—$R^2$ | I13 |
| $R^3$—$A^3$—A—$Z^1$—$A^2$—$R^2$ | I14 |
| $R^1$—A—$A^2$—$Z^2$—$A^3$—$R^3$ | I15 |
| $R^3$—$A^3$—$Z^2$—A—$A^2$—$R^2$ | I16 |
| $R^3$—$A^3$—$Z^2$—A—$Z^1$—$A^2$—$R^2$ | I17 |
| $R^1$—A—$Z^1$—$A^2$—$Z^2$—$A^3$—$R^3$ | I18 |
| $R^1$—$A^4$—$Z^3$—A—$Z^1$—$A^2$—$R^2$ | I19 |
| $R^1$—A—$Z^3$—$A^4$—$Z^1$—$A^2$—$R^2$ | I20 |
| $R^3$—$A^3$—$A^4$—A—$A^2$—$R^2$ | I21 |
| $R^3$—$A^3$—A—$A^4$—$A^2$—$R^2$ | I22 |
| $R^1$—$A^4$—A—$A^2$—$A^3$—$R^3$ | I23 |
| $R^1$—A—$A^4$—$A^2$—$A^3$—$R^3$ | I24 |
| $R^3$—$A^3$—A—$A^2$—$A^3$—$R^3$ | I25 |
| $R^3$—$A^3$—$A^3$—A—$A^2$—$R^3$ | I26 |
| $R^1$—A—$A^2$—$A^3$—$A^3$—$R^3$ | I27 |
| $R^3$—$A^3$—$Z^2$—A—$A^2$—$A^3$—$R^3$ | I28 |
| $R^3$—$A^3$—A—$Z^1$—$A^2$—$A^3$—$R^3$ | I29 |
| $R^3$—$A^3$—A—$Z^1$—$A^2$—$A^3$—$R^3$ | I30 |
| $R^3$—$A^3$—A—$A^2$—$Z^2$—$A^3$—$R^3$ | I31 |
| $R^1$—A—$A^4$—$Z^1$—$A^2$—$A^3$—$R^3$ | I32 |
| $R^1$—$A^4$—A—$Z^1$—$A^2$—$A^3$—$R^3$ | I33 |
| $R^3$—$A^3$—$A^4$—A—$Z^1$—$A^2$—$R^2$ | I34 |
| $R^3$—$A^3$—A—$A^4$—$Z^1$—$A^2$—$R^2$ | I35 |
| $R^1$—$A^4$—A—$A^2$—$Z^2$—$A^3$—$R^3$ | I36 |
| $R^1$—A—$A^4$—$A^2$—$Z^2$—$A^3$—$R^3$ | I37 |
| $R^3$—$A^3$—$Z^2$—$A^4$—A—$A^2$—$R^2$ | I38 |
| $R^3$—$A^3$—$Z^2$—A—$A^4$—$A^2$—$R^2$ | I39 |
| $R^3$—$A^3$—A—$A^2$—$Z^2$—$A^3$—$R^3$ | I40 |
| $R^3$—$A^3$—$Z^2$—A—$A^2$—$A^3$—$R^3$ | I41 |
| $R^3$—$A^3$—$A^3$—A—$Z^1$—$A^2$—$R^2$ | I42 |
| $R^3$—$A^3$—$A^4$—$Z^3$—A—$A^2$—$R^2$ | I43 |
| $R^3$—$A^3$—A—$Z^3$—$A^4$—$A^2$—$R^2$ | I44 |
| $R^1$—A—$A^2$—$Z^2$—$A^3$—$A^3$—$R^3$ | I45 |
| $R^1$—$A^4$—$Z^3$—A—$A^2$—$A^3$—$R^3$ | I46 |
| $R^1$—A—$Z^3$—$A^4$—$A^2$—$A^3$—$R^3$ | I47 |

-continued

| | |
|---|---|
| $R^3-A^3-A^3-Z^2-A-A^2-R^2$ | I48 |
| $R^1-A-Z^1-A^2-A^3-A^3-R^3$ | I49 |
| $R^3-A^3-Z^2-A^4-A-Z^1-A^2-R^2$ | I50 |
| $R^3-A^3-Z^2-A-A^4-Z^1-A^2-R^2$ | I51 |
| $R^1-A^4-A-Z^1-A^2-Z^2-A^3-R^3$ | I52 |
| $R^1-A-A^4-Z^1-A^2-Z^2-A^3-R^3$ | I53 |
| $R^3-A^3-A-Z^1-A^2-Z^2-A^3-R^3$ | I54 |
| $R^3-A^3-Z^2-A-A^2-Z^2-A^3-R^3$ | I55 |
| $R^3-A^3-Z^2-A-Z^1-A^2-A^3-R^3$ | I56 |
| $R^3-A^3-A^4-Z^3-A-Z^1-A^2-R^2$ | I57 |
| $R^3-A^3-A-Z^3-A^4-Z^1-A^2-R^2$ | I58 |
| $R^1-A^4-Z^3-A-A^2-Z^2-A^3-R^3$ | I59 |
| $R^1-A-Z^3-A^4-A^2-Z^2-A^3-R^3$ | I60 |
| $R^3-A^3-Z^2-A^4-Z^3-A-A^2-R^2$ | I61 |
| $R^3-A^3-Z^2-A-Z^3-A^4-A^2-R^2$ | I62 |
| $R^1-A^4-Z^3-A-Z^1-A^2-A^3-R^3$ | I63 |
| $R^1-A-Z^3-A^4-Z^1-A^2-A^3-R^3$ | I64 |
| $R^3-A^3-A^3-Z^2-A-Z^1-A^2-R^2$ | I65 |
| $R^1-A-Z^1-A^2-Z^2-A^3-A^3-R^3$ | I66 |
| $R^3-A^3-Z^2-A-Z^1-A^2-Z^2-A^3-R^3$ | I67 |
| $R^3-A^3-Z^2-A^4-Z^3-A-Z^1-A^2-R^2$ | I68 |
| $R^3-A^3-Z^2-A-Z^3-A^4-Z^1-A^2-R^2$ | I69 |
| $R^1-A^4-Z^3-A-Z^1-A^2-Z^2-A^3-R^3$ | I70 |
| $R^1-A-Z^3-A^4-Z^1-A^2-Z^2-A^3-R^3$ | I71 |
| $R^3-A^3-A^4-A-A^2-A^3-R^3$ | I72 |
| $R^3-A^3-A-A^4-A^2-A^3-R^3$ | I73 |
| $R^3-A^3-A^4-A-A^2-A^3-R^3$ | I74 |
| $R^3-A^3-A-A^4-A^2-A^3-R^3$ | I75 |
| $R^1-A-A^4-A^2-A^3-A^3-R^3$ | I76 |
| $R^3-A^3-A-A^4-A^2-Z^2-A^3-R^3$ | I77 |
| $R^3-A^3A-A^4-A^2-Z^2-A^3-R^3$ | I78 |
| $R^3-A^3A^4-A-Z^1-A^2-A^3-R^3$ | I79 |
| $R^3-A^3-A-A^4-Z^1-A^2-A^3-R^3$ | I80 |
| $R^3-A^3-Z^2-A^4A-A^2-A^3-R^3$ | I81 |
| $R^3-A^3-Z^2-A-A^4-A^2-A^3-R^3$ | I82 |
| $R^3-A^3-Z^4-A-Z^1-A^2-Z^2-A^3-R^3$ | I83 |
| $R^3-A^3-A-A^4-Z^1-A^2-Z^2-A^3-R^3$ | I84 |
| $R^3-A^3-Z^2-A^4-A-A^2-Z^2-A^3-R^3$ | I85 |
| $R^3-A^3-Z^2-A-A^4-A^2-Z^2-A^3-R^3$ | I86 |
| $R^3-A^3-Z^2-A-A^4-Z^1-A^2-A^3-R^3$ | I87 |
| $R^3-A^3-Z^2-A-A^4-Z^1-A^2-A^3-R^3$ | I88 |
| $R^3-A^3-Z^2-A^4-A-Z^1-A^2-Z^2-A^3-R^3$ | I89 |
| $R^3-A^3-Z^2-A-A^4-Z^1-A^2-Z^2-A^3-R^3$ | I90 |
| $R^1-A^4-Z^3-A-Z^1-A^2-Z^2-A^3-A^3-R^3$ | I91 |
| $R^1-A-Z^3-A^4-Z^1-A^2-Z^2-A^3-A^3-R^3$ | I92 |
| $R^3-A^3-A^3-Z^2-A-Z^1-A^2-Z^2-A^3-R^3$ | I93 |
| $R^3-A^3-Z^2-A-Z^1-A^2-Z^2-A^3-A^3-R^3$ | I94 |

Particularly preferred smaller groups of compounds are those of the formulae I001 to I002:

| | |
|---|---|
| $R^1$—Phe—$Z^1$—A—$R^2$ | I001 |
| $R^1$—Cy—$Z^1$—A—$R^2$ | I002 |
| $R^1$—Dio—$Z^1$—A—$R^2$ | I003 |
| $R^1$—Pip—$Z^1$—A—$R^2$ | I004 |
| $R^1$—Bi—$Z^1$—A—$R^2$ | I005 |
| $R^1$—Pyr—$Z^1$—A—$R^2$ | I006 |
| $R^1$—Phe—$Z^1$—A—$Z^2$—Phe—$R^2$ | I007 |
| $R^1$—Dio—$Z^1$—A—$Z^2$—Cy—$R^2$ | I008 |
| $R^1$—Cy—$Z^1$—A—$Z^2$—Phe—$R^2$ | I009 |
| $R^1$—Cy—$Z^1$—A—$Z^2$—Cy—$R^2$ | I010 |
| $R^1$—Phe—Phe—$Z^1$—A—$R^2$ | I011 |
| $R^1$—Phe—Cy—$Z^1$—A—$R^2$ | I012 |
| $R^1$—Cy—Phe—$Z^1$—A—$R^2$ | I013 |
| $R^1$—Cy—Cy—$Z^1$—A—$R^2$ | I014 |
| $R^1$—Phe—Phe—$Z^1$—A—$Z^2$—Phe—$R^2$ | I015 |
| $R^1$—Phe—Phe—$Z^1$—A—$Z^2$—Cy—$R^2$ | I016 |
| $R^1$—Phe—Cy—$Z^1$—A—$Z^2$—Phe—$R^2$ | I017 |
| $R^1$—Phe—Cy—$Z^1$—A—$Z^2$—Cy—$R^2$ | I018 |
| $R^1$—Cy—Phe—$Z^1$—A—$Z^2$—Phe—$R^2$ | I019 |
| $R^1$—Cy—Phe—$Z^1$—A—$Z^2$—Cy—$R^2$ | I020 |
| $R^1$—Cy—Cy—$Z^1$—A—$Z^2$—Phe—R | I021 |
| $R^1$—Cy—Cy—$Z^1$—A—$Z^2$—Cy—$R^2$ | I022 |

Compounds which are also preferred are the cyclohexane derivatives of the formula II $$R^{1'}-A-Z^0-(A^{1'}-Z^{1'})_m-(A^{2'})_n-R^{2'} \qquad II$$

wherein $R^{1'}$ and $R^{2'}$ are each H, an alkyl group with 1–10 C atoms, it also being possible for one or two non-adjacent $CH_2$ groups to be replaced by O atoms, F, Cl, Br, CN, —COOR, —O—COR, SOR, $SO_2R$ or —C≡C—$R^{3'}$, $A^{1'}$ and $A^{2'}$ are each 1,4-phenylene, 1,4-cyclohexylene, 1,3-dioxane-2,5-diyl, 1,3-dithiane-2,5-diyl, piperidine-1,4-diyl, 1,4-bicyclo(2,2,2)-octylene, pyridazine-3,6-diyl or pyrimidine-2,5-diyl groups which are unsubstituted or substituted (according to the above) by one or two F and/or Cl atoms and/or $CH_3$ groups and/or CN groups, or A, A is a 1,4-cyclohexylene group which is substituted in the 1- and/or 4-position by unsubstituted or substituted alkyl or fluorinated alkyl with in each case 1–5 C atoms, it also being possible for one or two non-adjacent $CH_2$ groups to be replaced by a grouping from the group comprising —O—, —CO—, —O—CO—, —CO—O—, —C≡C—, —S—, —SO— and —$SO_2$—, or by F, Cl, Br, CN and/or —CHO, and which can carry 1 or 2 further substituents, $Z^0$ and $Z^{1'}$ are each —CO—O—, —O—CO—, —$CH_2CH_2$—, —$OCH_2$—, —$CH_2O$— or a single bond, $R^{3'}$ is H, CN or an alkyl group with 1–7 C atoms, R is an alkyl group with 1–10 C atoms and m and n are each independently of one another 1 or 2, and $(m+n) \geq 3$, or, if $Z^0$ is a single bond and $Z^{1'}$ is not a single bond, $\geq 2$, wherein, for $m=2$ and/or $n=2$, the groups $A^{1'}$ and/or $A^{2'}$ and/or $Z^{1'}$ can be identical or different, and the acid addition salts of the basic compounds of this type.

The invention thus furthermore relates to the compounds of the formula II and to a process for their preparation, characterized in that a compound which otherwise corresponds to the formula II but contains one or more reducible groups and/or C-C bonds instead of H atoms is treated with a reducing agent, or in that a compound of the formula HX (wherein X is F, Cl, Br or CN) is added onto a compound which otherwise corresponds to the formula II but, instead of the radical A, contains a 1-cyclohexene-1,4-diyl group which can carry 1 or 2 further F, Cl or Br atoms and/or CN groups, or in that, to prepare esters of the formula II (wherein $R^{1'}$ and/or $R^{2'}$ are —OCOR and/or —COOR and/or wherein $Z^0$ and/or $Z^{1'}$ are —CO—O— or —O—CO—), a corresponding carboxylic acid or one of its reactive derivatives is reacted with a corresponding alcohol or one of its reactive derivatives, or in that, to prepare dioxane derivatives or dithiane derivatives of the formula II (wherein $A^{1'}$ and/or $A^{2'}$ are 1,3-dioxane-2,5-diyl or 1,3-dithiane-2,5-diyl), a corresponding aldehyde or one of its reactive derivatives is reacted with a corresponding diol or dithiol, or in that, to prepare nitriles of the formula II (wherein $R^{1'}$ and/or $R^{2'}$ are CN and/or wherein A and/or $A^{1'}$ and/or $A^{2'}$ are substituted by at least one CN group), a corresponding carboxylic acid amide is dehydrated or a corresponding carboxylic acid halide is reacted with sulfamide, or in that, to prepare nitriles of the formula II (wherein A is a 1,4-cyclohexylene group which is substituted in the 1- or 4-position by CN), an acetonitrile of the formula III $$E^1-CH_2CN \qquad III$$

wherein $E^1$ is (a) $R^{1'}$— or (b) $R^{2'}$—$(A^{2'})_n$—$(Z^{1'}$—$A^{1'})_m$—$Z^0$—and $R^{1'}$, $R^{2'}$, $A^{1'}$, $A^{2'}$, $Z^{1'}$, $Z^0$, m and n have the meanings given, is reacted with a compound of the formula IV $$(X^1-CH_2-CH_2)_2CH-E^2 \qquad IV$$

wherein $X^1$ is Cl, Br, I, OH or a reactive esterified OH group, $E^2$ is (a) $R^{2'}$—$(A^{2'})_n$—$(Z^{1'}$—$A^{1'})_m$—$Z^0$— or (b) $R^{1'}$— and $R^{1'}$, $R^{2'}$, $A^{1'}$, $A^{2'}$, $Z^{1'}$, $Z^0$, m and n have the meanings given, or in that, to prepare nitriles of the formula II (wherein A is a 1,4-cyclohexylene group which is substituted in the 1- or 4-position by CN and which can additionally be substituted by one or two F atoms and/or CN groups; and wherein, furthermore, in (a) $Z^0$ is a single bond), a nitrile of the formula V $$Q^1-Q^3-CN \qquad V$$

wherein $Q^1$ is (a) $R^{1'}$— or (b) $R^{2'}$—$(A^{2'})_n$—$(Z^{1'}$—$A^{1'})_m$—$Z^0$— and $Q^3$ is a 1,4-cyclohexylene group which is unsubstituted or mono- or di-substituted by F and/or CN, and $R^{1'}$, $R^{2'}$, $A^{1'}$, $A^{2'}$, $Z^{1'}$, $Z^0$, m and n have the meanings given, is reacted with a compound of the formula VI $$Q^2-X^1 \qquad VI$$

wherein $Q^2$ is (a) $R^{2'}$—$(A^{2'})_n$—$(Z^{1'}$—$A^{1'})_m$— or (b) $R^{1'}$ and and $X^{1'}$, $R^{1'}$, $R^{2'}$, $A^{1'}$, $A^{2'}$, $Z^{1'}$, m and n have the meanings given, or in that to prepare ethers of the formula II (wherein $R^{1'}$ and/or $R^{2'}$ are an alkyl group, in which one or two $CH_2$ groups are replaced by O atoms, and/or $Z^0$ and/or $Z^{1'}$ are an —$OCH_2$— or —$CH_2O$— group), a corresponding hydroxy compound is etherified, or in that, to prepare compounds of the formula II wherein $R^{1'}$ and/or $R^{2'}$ is SOR or $SO_2R$, a corresponding compound wherein $R^1$ and/or $R^2$ are SR or SOR is oxidized, or in that, to prepare compounds of the formula II which contain $CF_3$ groups, a corresponding carboxylic acid is reacted with $SF_4$, and/or in that, if appropriate, a chlorine or bromine compound of the formula II (wherein $R^{1'}$ and/or $R^{2'}$ are Cl or Br and/or wherein A is substituted by at least one chlorine or bromine atom and/or $A^{1'}$ and/or $A^{2'}$ are substituted by at least one chlorine atom) is reacted with a cyanide, and/or in that, if appropriate, a base of the formula II is converted into one of its acid addition salts by treatment with an acid, or in that, if appropriate, a compound of the formula II is liberated from one of its acid addition salts by treatment with a base.

The invention furthermore relates to the use of the compounds of the formula II as components of liquid crystal phases. The invention also relates to liquid crystal phases containing at least one compound of the formula II and liquid crystal display elements, in particular electrooptical display elements, containing such phases.

Above and below, $R^{1'}$, $R^{2'}$, $R^{3'}$, R, $A^{1'}$, $A^{2'}$, A, $Z^0$, $Z^{1'}$, m, n, $X^1$, $E^1$, $E^2$, $Q^1$, $Q^2$ and $Q^3$ have the meaning given, unless expressly indicated otherwise.

The compounds of the formula II include, in particular, compounds of the part formula IIa (with three rings), IIb-IIg (with four rings) and IIh and IIi (with five rings):

| | |
|---|---|
| $R^{1'}$—A—$A^{1'}$—$Z^{1'}$—$A^{2'}$—$R^{2'}$ | IIa |
| $R^{1'}$—A—$(A^{1'})_2$—$A^{2'}$—$R^{2'}$ | IIb |
| $R^{1'}$—A—$A^{1'}$—$Z^{1'}$—$(A^{2'})_2$—$R^{2'}$ | IIc |
| $R^{1'}$—A—$(A^{1'})_2$—$Z^{1'}$—$A^{2'}$—$R^{2'}$ | IId |
| $R^{1'}$—A—$Z^0$—$(A^{1'})_2$—$A^{2'}$—$R^{2'}$ | IIe |
| $R^{1'}$—A—$Z^0$—$(A^{1'})_2$—$Z^{1'}$—$A^{2'}$—$R^{2'}$ | IIf |
| $R^{1'}$—A—$(A^{1'}$—$Z^{1'})_2$—$A^{2'}$—$R^{1'}$ | IIg |
| $R^{1'}$—A—$(A^{1'})_2$—$(A^{2'})_2$—$R^{2'}$ | IIh |
| $R^{1'}$—A—$(A^{1'})_2$—$Z^{1'}$—$(A^{2'})_2$—$R^{2'}$ | IIi. |

Of these, those of the part formulae IIa, IIb, IIc, IId and IIe are preferred.

The preferred compounds of the part formula IIa include those of the part formulae IIa1 to IIa25:

| | |
|---|---|
| $R^{1'}$—A—Phe—$Z^{1'}$—Phe—$R^{2'}$ | IIa1 |
| $R^{1'}$—A—Phe—$Z^{1'}$—Cy—$R^{2'}$ | IIa2 |
| $R^{1'}$—A—Cy—$Z^{1'}$—Cy—$R^{2'}$ | IIa3 |
| $R^{1'}$—A—Cy—$Z^{1'}$—Phe—$R^{2'}$ | IIa4 |
| $R^{1'}$—A—Pyr—$Z^{1'}$—Phe—$R^{2'}$ | IIa5 |
| $R^{1'}$—A—Pyr—$Z^{1'}$—Cy—$R^{2'}$ | IIa6 |
| $R^{1'}$—A—Cy—$Z^{1'}$—Dio—$R^{2'}$ | IIa7 |
| $R^{1'}$—A—Cy—$Z^{1'}$—Dit—$R^{2'}$ | IIa8 |
| $R^{1'}$—A—Cy—$Z^{1'}$—Pyr—$R^{2'}$ | IIa9 |
| $R^{1'}$—A—Cy—$Z^{1'}$—Pyn—$R^{2'}$ | IIa10 |
| $R^{1'}$—A—Cy—$Z^{1'}$—Bi—$R^{2'}$ | IIa11 |
| $R^{1'}$—A—Phe—$Z^{1'}$—Dio—$R^{2'}$ | IIa12 |
| $R^{1'}$—A—Phe—$Z^{1'}$—Dit—$R^{2'}$ | IIa13 |
| $R^{1'}$—A—Phe—$Z^{1'}$—Bi—$R^2$ | IIa14 |
| $R^{1'}$—A—Phe—$Z^{1'}$—Pyn—$R^{2'}$ | IIa15 |
| $R^{1'}$—A—Dio—$Z^{1'}$—Phe—$R^{2'}$ | IIa16 |
| $R^{1'}$—A—Dio—$Z^{1'}$—Cy—$R^{2'}$ | IIa17 |
| $R^{1'}$—A—Dit—$Z^{1'}$—Phe—$R^{2'}$ | IIa18 |
| $R^{1'}$—A—Dit—$Z^{1'}$—Cy—$R^{2'}$ | IIa19 |
| $R^{1'}$—A—Bi—$Z^{1'}$—Fhe—$R^{2'}$ | IIa20 |
| $R^{1'}$—A—Bi—$Z^{1'}$—Cy—$R^{2'}$ | IIa21 |
| $R^{1'}$—A—Pyr—$Z^{1'}$—Cy—$R^{2'}$ | IIa22 |
| $R^{1'}$—A—Pyr—$Z^{1'}$—Phe—$R^{2'}$ | IIa23 |
| $R^{1'}$—A—Pyn—$Z^{1'}$—Phe—$R^{2'}$ | IIa24 |
| $R^{1'}$—A—Pyn—$Z^{1'}$—Cy—$R^{2'}$ | IIa25 |

Of these, those of the formulae IIa1 to IIa4, in particular IIa1 and IIa2, are particularly preferred.

In the compounds of part formula IIa, $Z^{1'}$ and $Z^0$ are preferably —CO—O—, —O—CO— or —$CH_2CH_2$—.

The preferred compounds of part formula IIb include those of the part formulae IIb1 to IIb16:

| | |
|---|---|
| $R^{1'}$—A—Phe—Phe—Cy—$R^{2'}$ | IIb1 |
| $R^{1'}$—A—Phe—Phe—Dio—$R^{2'}$ | IIb2 |
| $R^{1'}$—A—Phe—Phe—A—$R^{2'}$ | IIb3 |
| $R^{1'}$—A—Cy—Phe—Phe—$R^{2'}$ | IIb4 |
| $R^{1'}$—A—Cy—Phe—Cy—$R^{2'}$ | IIb5 |
| $R^{1'}$—A—Cy—Phe—Dio—$R^{2'}$ | IIb6 |
| $R^{1'}$—A—Phe—Phe—Dit—$R^2$ | IIb7 |
| $R^{1'}$—A—Phe—Phe—Bi—$R^2$ | IIb8 |
| $R^{1'}$—A—Phe—Cy—Cy—$R^{2'}$ | IIb9 |
| $R^{1'}$—A—Phe—Cy—Dio—$R^{2'}$ | IIb10 |
| $R^{1'}$—A—Phe—Cy—Dit—$R^{2'}$ | IIb11 |
| $R^{1'}$—A—Phe—Pyr—Cy—$R^{2'}$ | IIb12 |
| $R^{1'}$—A—Phe—Pyn—Cy—$R^{2'}$ | IIb13 |
| $R^{1'}$—A—Pyr—Phe—Cy—$R^{2'}$ | IIb14 |
| $R^{1'}$—A—Pyn—Phe—Cy—$R^{2'}$ | IIb15 |
| $R^{1'}$—A—Pyn—Phe—Dio—$R^{2'}$ | IIb16 |

Of these, those of the formulae IIb1 to IIb4 are particularly preferred.

Compounds of the formula IIb wherein at least one of the rings $A^{1'}$ is substituted, preferably by F, are furthermore especially preferred.

The preferred compounds of the part formula IIc include those wherein $A^{1'}$ and $A^{2'}$ are chosen from the series Cy, Phe and Dio and $Z^{1'}$ is —CO—O—, —O—CO— or —CH$_2$CH$_2$—.

The preferred compounds of the part formula IId include those of the part formulae IId1 to IId8:

|  |  |
|---|---|
| $R^{1'}$—A—Phe—Phe—$Z^{1'}$—Cy—$R^{2'}$ | IId1 |
| $R^{1'}$—A—Phe—Phe—$Z^{1'}$—Dio—$R^{2'}$ | IId2 |
| $R^{1'}$—A—Phe—Phe—$Z^{1'}$—Phe—$R^{2'}$ | IId3 |
| $R^{1'}$—A—Cy—Phe—$Z^{1'}$—Cy—$R^{2'}$ | IId4 |
| $R^{1'}$—A—Cy—Phe—$Z^{1'}$—Phe—$R^{2'}$ | IId5 |
| $R^{1'}$—A—Cy—Cy—$Z^{1'}$—Phe—$R^{2'}$ | IId6 |
| $R^{1'}$—A—Cy—Cy—$Z^{1'}$—Cy—$R^{2'}$ | IId7 |
| $R^{1'}$—A—Cy—Phe—$Z^{1'}$—Dio—$R^{2'}$ | IId8. |

The preferred compounds of the part formula IIe include those of the part formulae IIe1 to IIe8:

|  |  |
|---|---|
| $R^{1'}$—A—$Z^0$—Phe—Phe—Cy—$R^{2'}$ | IIe1 |
| $R^{1'}$—A—$Z^0$—Cy—Phe—Phe—$R^{2'}$ | IIe2 |
| $R^{1'}$—A—$Z^0$—Cy—Phe—Cy—$R^{2'}$ | IIe3 |
| $R^{1'}$—A—$Z^0$—Phe—Phe—Dio—$R^{2'}$ | IIe4 |
| $R^{1'}$—A—$Z^0$—Cy—Cy—Phe—$R^{2'}$ | IIe5 |
| $R^{1'}$—A—$Z^0$—Phe—Cy—Cy—$R^2$ | IIe6 |
| $R^{1'}$—A—$Z^0$—Dio—Cy—Phe—$R^2$ | IIe7 |
| $R^{1'}$—A—$Z^0$—Phe—Cy—Dio—$R^2$ | IIe8. |

Of these, those of the formulae IIe1, IIe4 and IIe6 are particularly preferred. Compounds of the formulae IIe1 to IIe8 wherein at least one of the rings $A^{1'}$ is substituted, preferably by F, and/or those wherein $Z^0$ is —CO—O—, —O—CO— or —CH$_2$CH$_2$—, particularly preferably —CH$_2$CH$_2$—, are furthermore especially preferred.

In the compounds of the formulae I and II above and below, a substituted alkyl group or substituted ethylene is an alkyl group or —CH$_2$CH$_2$— (ethylene) group which is monosubstituted or polysubstituted, on different C atoms, by halogen, preferably fluorine or chlorine, or CN. Preferably there will be only one halo or cyano substituent on each C-atom.

In the compounds of the formulae I and II above and below, $R^1$ and $R^2$, or $R^{1'}$ and $R^{2'}$, are preferably alkyl, and furthermore alkoxy or another oxaalkyl group. Compounds of the formulae I and II wherein one of the radicals $R^1$ and $R^2$, or $R^{1'}$ and $R^{2'}$, is H, CN, F, Cl, Br, SOR or SO$_2$R, in particular H, CN, F or Cl, are furthermore preferred.

$A^2$, $A^3$ and $A^4$, or $A^{1'}$ and $A^{2'}$, are preferably independently of one another Cy, Dio or Phe, and furthermore preferably Dit, Pyr or Pip; the compound of the formula I or II preferably contains not more than one of the radicals Dio, Dit, Pip, Bi, Pyn or Pyr.

A is preferably a 1—X—1,4-cyclohexylene group which carries no further substituents and wherein X is alkyl, alkoxy, fluorinated alkyl or fluorinated alkoxy with in each case 1-5 C atoms, or F, Cl, Br or CN. Particularly preferred is CN. X is preferably a CN, CH$_3$, CH$_3$O or CF$_3$ group. A is furthermore preferably a 1-X-1,4-cyclohexylene group which carries no further substituents and wherein X is —CHO, —COO—alkyl, —S—alkyl, —SO—alkyl, —SO$_2$—alkyl, wherein alkyl is a straight-chain alkyl group with 1-4 C atoms. $Z^1$, $Z^2$ and $Z^3$, or $Z^{0'}$ and $Z^{1'}$, are preferably independently of one another single bonds or —CH$_2$CH$_2$—, —CO—O— or —O—CO— groups. Further substituents of A are preferably CH$_3$, F or CN. but in general all A substituents disclosed for the 1- and/or 4-positions are possible further substituents.

n and p are preferably 1. Substituted ethylene is preferably —CH$_2$CHX—, wherein X has one of the meanings indicated above. F substitution on the alkyl groups includes one F-atom to perfluorination.

$X^1$ is preferably Cl or Br, but also I, OH or reactively esterified OH, such as alkylsulphonyloxy with, in particular, 1-6 C atoms (for example methylsulfonyloxy) or arylsulfonyloxy with, in particular, 6-10 C atoms (for example phenyl-, p-tolyl- or naphthyl-sulfonyloxy).

If $R^{1'}$ and/or $R^{2'}$, or $R^1$ and/or $R^2$ and/or $R^3$, are alkyl radicals in which one ("alkoxy" or "oxaalkyl") or two ("alkoxyalkoxy" or "dioxaalkyl") non-adjacent CH$_2$ groups can be replaced by O atoms, they can be straight-chain or branched. Preferably, they are straight-chain and have 2, 3, 4, 5, 6 or 7 C atoms, and are accordingly preferably ethyl, propyl, butyl, pentyl, hexyl, heptyl, ethoxy, propoxy, butoxy, pentoxy, hexoxy, heptoxy, 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl or 2-, 3-, 4-, 5- or 6-oxaheptyl, and furthermore methyl, octyl, nonyl, decyl, methoxy, octoxy, nonoxy, decoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl or 1,3-, 1,4-, 1,5-, 1,6-, 2,4-, 2,5-, 2,6-, 3,5-, 3,6- or 4,6-dioxaheptyl.

Compounds of the formulae I and II with branched end group substituents $R^1$, $R^2$ and/or $R^3$ or $R^{1'}$ and/or $R^{2'}$ can occasionally be of importance because of a better solubility in the usual liquid crystal base materials, but in particular as chiral doping substances, if they are optically active.

Branched groups of this type as a rule contain not more than one chain branching. Preferred branched radicals are isopropyl, 2-butyl (=1-methyloropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

In the case of compounds with branched end group substituents, the formulae I and II include both the optical antipodes and the racemates as well as mixtures thereof.

In the radicals R and X, the alkyl groups and/or alkoxy groups are likewise preferably straight-chain and are, in particular, methyl or ethyl, and furthermore propyl, butyl or pentyl, and X is also methoxy or ethoxy, and furthermore propoxy, butoxy or pentoxy.

Of the compounds of the formulae I and II and their sub-formulae, those in which at least one of the radicals contained therein has one of the preferred meanings mentioned are preferred. Particularly preferred smaller groups of compounds are those of the formulae VIII 1-56 (corresponding to formula I) and VIII 57-81 (corresponding to formula II):

|  |  |
|---|---|
| Alkyl—$A^1$—$Z^1$—A—Alkyl | VIII 1 |

| | |
|---|---|
| -continued | |
| Alkoxy—A¹—Z¹—A—Alkyl | VIII 2 |
| Alkyl—Phe—Z¹—A—Alkyl | VIII 3 |
| Alkoxy—Phe—Z¹—A—Alkyl | VIII 4 |
| Alkyl—Phe—A—Alkyl | VIII 5 |
| Alkoxy—Phe—A—Alkyl | VIII 6 |
| Alkyl—Phe—CO—O—A—Alkyl | VIII 7 |
| Alkoxy—Phe—CO—O—A—Alkyl | VIII 8 |
| Alkyl—Phe—O—CO—A—Alkyl | VIII 9 |
| Alkoxy—Phe—O—CO—A—Alkyl | VIII 10 |
| Alkyl—Phe—CH₂CH₂—A—Alkyl | VIII 11 |
| Alkoxy—Phe—CH₂CH₂—A—Alkyl | VIII 12 |
| Alkyl—Phe—Phe—CH₂CH₂—A—Alkyl | VIII 13 |
| Alkoxy—Phe—Phe—CH₂CH₂—A—Alkyl | VIII 14 |
| Alkyl—Phe—O—CH₂—A—Alkyl | VIII 15 |
| Alkoxy—Phe—O—CH₂—A—Alkyl | VIII 16 |
| Alkyl—Phe—CH₂—O—A—Alkyl | VIII 17 |
| Alkoxy—Phe—CH₂—O—A—Alkyl | VIII 18 |
| Alkyl—Cy—Z¹—A—Alkyl | VIII 19 |
| Alkyl—Cy—A—Alkyl | VIII 20 |
| Alkyl—Cy—CO—O—A—Alkyl | VIII 21 |
| Alkyl—Cy—O—CO—A—Alkyl | VIII 22 |
| Alkyl—Cy—CH₂CH₂—A—Alkyl | VIII 23 |
| Alkyl—Cy—O—CH₂—A—Alkyl | VIII 24 |
| Alkyl—Cy—CH₂—O—A—Alkyl | VIII 25 |
| Alkyl—Dio—A—Alkyl | VIII 26 |
| Alkyl—Dit—A—Alkyl | VIII 27 |
| Alkyl—Pip—A—Alkyl | VIII 28 |
| Alkyl—Pyr—A—Alkyl | VIII 29 |
| Alkoxy—Pry—A—Alkyl | VIII 30 |
| Alkyl—Pyn—A—Alkyl | VIII 31 |
| Alkyl—Phe—Phe—A—Alkyl | VIII 32 |
| Alkoxy—Phe—Phe—A—Alkyl | VIII 33 |
| Alkyl—Phe—Cy—A—Alkyl | VIII 34 |
| Alkoxy—Phe—Cy—A—Alkyl | VIII 35 |
| Alkyl—Phe—A—Cy—Alkyl | VIII 36 |
| Alkyl—Cy—Cy—A—Alkyl | VIII 37 |
| Alkoxy—Cy—Cy—A—Alkyl | VIII 38 |
| Alkyl—Cy—Phe—A—Alkyl | VIII 39 |
| Alkyl—Cy—A—Cy—Alkyl | VIII 40 |
| Alkyl—Cy—A—Cy—Alkoxy | VIII 41 |
| Alkyl—Cy—Phe—O—CO—A—Alkyl | VIII 42 |
| Alkyl—Cy—Cy—CO—O—A—Alkyl | VIII 43 |
| Alkyl—Cy—Cy—O—CO—A—Alkyl | VIII 44 |
| Alkyl—Dio—Phe—CO—O—A—Alkyl | VIII 45 |
| Alkyl—Dio—Phe—O—CO—A—Alkyl | VIII 46 |
| Alkyl—Dit—Phe—CO—O—A—Alkyl | VIII 47 |
| Alkyl—Dit—Phe—O—CO—A—Alkyl | VIII 48 |
| Alkyl—Cy—Phe—CH₂CH₂—A—Alkyl | VIII 49 |
| Alkyl—Cy—CY—CH₂CH₂—A—Alkyl | VIII 50 |
| Alkyl—Dio—Phe—CH₂CH₂—A—Alkyl | VIII 51 |
| Alkyl—Dit—Phe—CH₂CH₂—A—Alkyl | VIII 52 |
| Alkyl—Phe—Phe—CO—O—A—Alkyl | VIII 53 |
| Alkoxy—Phe—Phe—CO—O—A—Alkyl | VIII 54 |
| Alkyl—Phe—Phe—O—CO—A—Alkyl | VIII 55 |
| Alkoxy—Phe—Phe—O—CO—A—Alkyl | VIII 56 |
| Alkyl—A—Phe—Phe—C—Alkyl | VIII 57 |
| Alkyl—A—Phe—Phe—Dio—Alkyl | VIII 58 |
| Alkyl—A—Phe—Phe—Dio—Alkoxy | VIII 59 |
| Alkyl—A—Phe—Phe—A—Alkyl | VIII 60 |
| Alkyl—A—Cy—Phe—Phe—Alkyl | VIII 61 |
| Alkyl—A—Cy—Phe—Phe—Alkoxy | VIII 62 |
| Alkyl—A—Cy—Phe—Phe—CN | VIII 63 |
| Alkyl—A—Phe—CH₂CH₂—Phe—Alkyl | VIII 64 |
| Alkyl—A—Phe—CH₂CH₂—Phe—Alkoxy | VIII 65 |
| Alkyl—A—Phe—CH₂CH₂—Phe—CN | VIII 66 |
| Alkyl—A—Phe—CH₂CH₂—Cy—Alkyl | VIII 67 |
| Alkyl—A—Cy—CH₂CH₂—Cy—Alkyl | VIII 68 |
| Alkyl—A—Cy—CH₂CH₂—Phe—Alkyl | VIII 69 |
| Alkyl—A—Cy—CH₂CH₂—Phe—Alkoxy | VIII 70 |
| Alkyl—A—Cy—CH₂CH₂—Phe—CN | VIII 71 |
| Alkyl—A—Phe—COO—Phe—Alkyl | VIII 72 |
| Alkyl—A—Phe—COO—Phe—Alkoxy | VIII 73 |
| Alkyl—A—Phe—COO—Phe—CN | VIII 74 |
| Alkyl—A—Phe—OCO—Phe—Alkyl | VIII 75 |
| Alkyl—A—Phe—OCO—Phe—Alkoxy | VIII 76 |
| Alkyl—A—Phe—OCO—Phe—CN | VIII 77 |
| Alkyl—A—Phe—COO—Cy—Alkyl | VIII 78 |
| Alkyl—A—Phe—OCO—Cy—Alkyl | VIII 79 |
| Alkyl—A—CH₂CH₂—Phe—Phe—Cy—Alkyl | VIII 80 |
| Alkyl—A—Phe—Phe—CH₂CH₂—Cy—Alkyl | VIII 81 |

In the compounds VIII 1-81 Alkyl and Alkoxy are preferably straight-chain alkyl and alkoxy groups having in each case 2 to 7 carbon atoms. VIII 32, VIII 33, VIII 36, VIII 37, VIII 39, VIII 40 and VIII 41 are particularly preferred.

In the compounds of the above formulae VIII 1-81, in particular VIII 32, 33, 57, 58, 59, 60, 61, 62 and 63, Phe can also be a 1,4-phenylene group which is laterally substituted in the 2- or 3-position, in particular by F. In the compounds of the abovementioned formulae, the group A contains a substituent X, which can be in the 1- or 4-position. Thus, for example, the compounds of the formula II include those of the following part formulae II' and II''

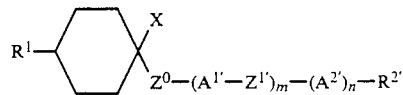

II'

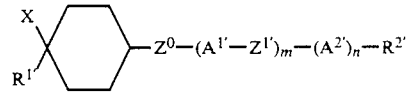

II''

(wherein the cyclohexane ring can additionally carry a further substituent X in the opposite position (4- or 1-position) of the cyclohexene ring and 1 or 2 further F, Cl or Br atoms and/or CN groups). In this context, particularly preferred compounds of the above formulae I are furthermore those in which the radical A is in each case

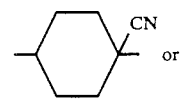

(1)

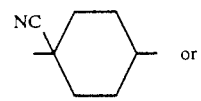

(2)

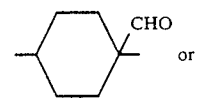

(3)

(4)

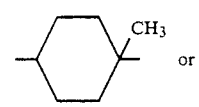

(5)

(6)

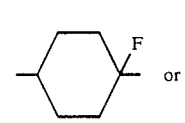

(7)

-continued

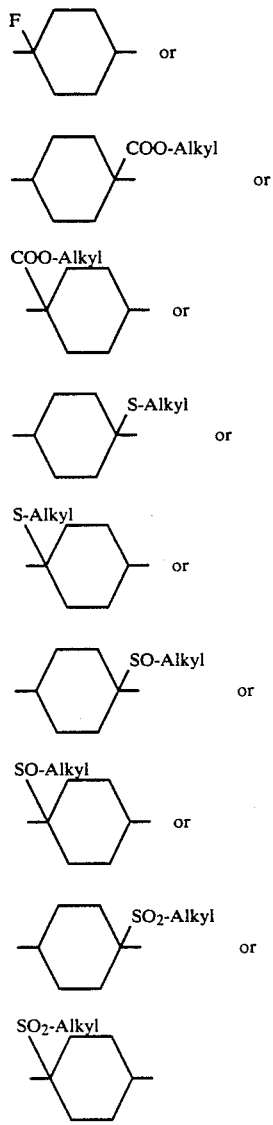

wherein alkyl in each case is a straight-chain alkyl group with 1-4 C atoms.

Those stereoisomers here in which the groups $R^{1'}$— and —$Z^0$—$(A^{1'}-Z^{1'})_m$—$(A^{2'})_n$—$R^{2'}$ are in the trans-position relative to one another, while the substituent X is in the cis-position relative to the opposite group are preferred. Thus, for example, the following stereoisomers of the compounds of the formula II' are preferred:

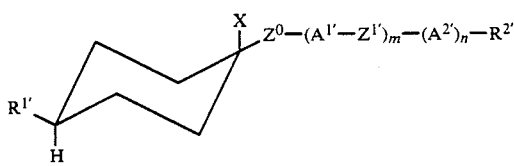

In general, those compounds of the formula I and II in which, in the ring A, the substituents in the 1- and 4-position with the longest chain length are in the trans-position are preferred. If mixtures of stereoisomers are obtained in the synthesis, the preferred isomers can be isolated by separation processes which are known per se, for example chromatography or crystallization (if appropriate in the presence of urea).

Those of the abovementioned formulae which contain one or more of the groups Dio, Dit, Pip and/or Pyr include in each case the two possible 2,5-position isomers (Dio, Dit or Pyr) or 1,4-position isomers (Pip).

Particularly preferred compounds of the formula I are those wherein $R^1$ and $R^2$ are each straight-chain or at most singly branched alkyl groups with 1-10 C atoms, it also being possible for one or two CH$_2$ groups to be replaced by O atoms or —CH=CH—, or F, Cl, Br, CN or —O—COR and $A^1$, $A^2$, A, $Z^0$, $Z^1$, R, m and n have the meaning given in the case of formula I. Alkenyl groups in the compounds of the formula I (or II) are preferably straight-chain trans-alkenyl groups of the formula,

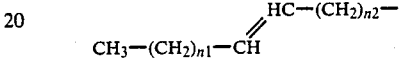

wherein n2 is 0 or 2, preferably 2, and n1 is 1 to 5.

Compounds of the formula I (wherein one of the radicals $R^1$, $R^2$ and $R^3$ is F, Cl, Br or CN, in particular CN) or of the formula II (wherein one of the radicals $R^{1'}$, $R^{2'}$ and $R^{3'}$ is F, Cl, Br or CN, in particular CN) wherein A in each case is a 1,4-cyclohexylene group which is substituted in the 1-position and/or 4-position by unsubstituted or substituted alkyl or fluorinated alkyl, each having 1 to 5 carbon atoms, wherein one or two CH$_2$ groups which are not adjacent to one another may furthermore be replaced with a grouping from the group comprising —O—, —CO—, —O—CO—, —CO—O—, —C—C—, —S—, —SO— and —SO$_2$—, and/or by —CHO, being compounds which exhibit positive dielectric anisotropy, are particularly suitable as components of liquid-crystalline phases having an overall positive dielectric anisotropy. In this context, A is preferably a 1,4-cyclohexylene group (formula (5) or (6)) which is substituted in the 1- position or 4-position by methyl. Particularly preferred compounds exhibiting positive dielectric anisotropy are those of the formula I, wherein $A^1$—$A^4$—$Z^3$—A— or —A—$Z^3$—$A^4$— and/or $A^2$ and, if appropriate, $A^3$ or $A^4$ are each 1,4-cyclohexylene. Particularly preferred compounds are those of the formulae Ia to Ie,

| | |
|---|---|
| $R^1$—Cy—Phe—CN | Ia |
| $R^1$—A—Cy—COO—Phe—CN | Ib |
| $R^1$—A—Phe—COO—Phe—CN | Ic |
| $R^2$—Cy—A—CN | Id |
| $R^2$—Cy—Cy—A—CN | Ie | wherein A has the preferred meaning given above, $R^1$ and $R^2$ are each preferably n-alkyl having 1 to 10, preferably 2 to 7, carbon atoms, and —Phe—CN is 4-cyanophenyl or 3-fluoro-4-cyanophenyl.

The liquid-crystalline phases according to the invention, containing these positive compounds of the formulae I and/or II, preferably contain at least one further component selected from the compounds of the following formulae:

alkyl—Phe—Phe—CN alkyl—Cy—Phe—CN alkyl—Cy—Phe—Phe—CN alkyl—Cy—Cy—Phe—CN alkyl—Cy—Cy—Cy—CN alkyl—Cy—Cy—CN alkyl—Dio—Phe—CN wherein alkyl in each case is n-alkyl having 2 to 7 carbon atoms.

The compounds of the formulae I and II are prepared by methods which are known per se, such as are described in the literature (for example in the standard works, such as Houben-Weyl, Methoden der Organischer Chemie (Methods of Organic Chemistry), Georg-Thieme-Verlag, Stuttgart), and in particular under reaction conditions which are known and suitable for the reactions mentioned. It is also possible to utilize variants which are known per se and are not mentioned in more detail here.

If desired, the starting substances can also be formed in situ, by a process in which they are not isolated from the reaction mixture but are immediately reacted further to give the compounds of the formula I or II.

Thus, the compounds of the formula I can be prepared by reducing a compound which otherwise corresponds to the formula I but contains one or more reducible groups and/or C-C bonds instead of H atoms.

Preferred possible reducible groups are carbonyl groups, in particular keto groups, and furthermore, for example, free or esterified hydroxyl groups or aromatically bonded halogen atoms. Preferred starting substances for the reduction correspond to the formula I, but can contain a cyclohexene ring or cyclohexanone ring instead of a cyclohexane ring and/or a —CH=CH— group instead of a —CH$_2$CH$_2$— group, and/or a —CO— group instead of a —CH$_2$— group, and/or a free or functionally modified (for example in the form of its p-toluenesulfonate) OH group instead of an H atom.

The reduction can be carried out, for example, by catalytic hydrogenation at temperatures between about 0° and about 200° and under pressures between about 1 bar and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are advantageously noble metals, such as Pt or Pd, which can be used in the form of oxides (for example PtO$_2$ or PdO) on a support (for example Pd on charcoal, calcium carbonate or strontium carbonate), or in finely divided form.

Ketones can also be reduced by the methods of Clemmensen (with zinc, zinc amalgam or tin and hydrochloric acid, advantageously in aqueous-alcohol solution or in a heterogeneous phase system with water/toluene at temperatures between about 80° and 120°) or Wolff-Kishner (with hydrazine, advantageously in the presence of alkali, such as KOH or NaOH, in a high-boiling solvent, such as diethylene glycol or triethylene glycol, at temperatures between about 100° and 200°), to give the corresponding compounds of the formula I containing alkyl groups and/or —CH$_2$CH$_2$— bridges.

Reductions with complex hydrides are furthermore possible. For example, arylsulfonyloxy groups can be removed by reduction with LiAlH$_4$, in particular p-toluenesulfonyloxymethyl groups can be reduced to methyl groups, advantageously in an inert solvent, such as diethyl ether or THF, at temperatures between about 0° and 100° C. Double bonds can be hydrogenated with NaBH$_4$ or tributyl-tin hydride in methanol (even in the presence of CN groups!); thus, for example, the corresponding cyclohexane derivatives are formed from 1-cyanocyclohexene derivatives.

Aldehydes of the formula I (wherein A denotes a 1,4-cyclohexylene group which is substituted in the 1-or 4-position by —CHO and which can additionally carry one or two further substituents) can also be obtained in an analogous manner by reduction of corresponding nitriles of the formula I.

Compounds of the formula I can furthermore be obtained by adding a compound of the formula HX (hydrogen fluoride, chloride, bromide or cyanide) onto a corresponding cyclohexene derivative (which corresponds to the formula I but contains, instead of the radical A, a 1-cyclohexene-1,4-diyl group which can carry 1 or 2 further F, Cl or Br atoms and/or CN groups).

This addition reaction is effected, for example, in the presence of an inert solvent, for example a halogenated hydrocarbon, such as CH$_2$Cl$_2$ or CHCl$_3$, a nitrile, such as acetonitrile, or an amide, such as dimethylformamide (DMF) at temperatures between about −10° and +150° and under pressures between about 1 and 100 bar. It may be advantageous to add catalysts, for example addition of HCN can be catalyzed by adding palladium bis-[2,3-O-isopropylidene-2,3-dihydroxy-1,4-bis-(diphenylphosphino)-butane].

Esters of the formula I (R$^1$ and/or R$^2$=—O—COR and/or —COOR and/or Z$^0$ and/or Z$^1$=—CO—O— or —O—CO—) can also be obtained by esterification of corresponding carboxylic acids, for example of the formulae R—COOH, R$^1$—A—COOH, R$^1$—A—Z$^0$—(A$^1$)$_m$—COOH or R$^1$—A—Z$^0$—(A$^1$)$_m$—A$^2$—COOH (or their reactive derivatives) with alcohols or phenols of the formulae R$^1$—A—Z$^0$—(A$^1$—Z$^1$)$_m$—(A$^2$)$_n$—OH, R$^2$—(A$^2$)$_n$—(Z$^1$—A$^1$)$_m$—Z$^0$—A—OH, R$^2$—(A$^2$)$_n$—(Z$^1$—A$^1$)$_m$—OH, R$^2$—(A$^2$)$_n$—OH or R$^2$—(A$^2$)$_{n-1}$—OH or their reactive derivatives).

Particularly suitable reactive derivatives of the carboxylic acids mentioned are the acid halides, above all the chlorides and bromides, and furthermore the anhydrides, for example also mixed anhydrides of the formulae R$^1$—A—CO—O—COCH$_3$, R$^1$—A—Z$^0$—(A$^1$—Z$^1$)$_m$—CO—O—COCH$_3$ or R$^1$—A—Z$^0$—(A$^1$—Z$^1$)$_m$—(A$^2$)$_n$—CO—O—COCH$_3$, azides or esters, in particular alkyl esters with 1-4 C atoms in the alkyl group.

The corresponding metal alcoholates or phenolates of the formula —R$^1$—A—Z$^0$—(A$^1$—Z$^1$)$_m$—(A$^2$)$_n$—OM, R$^2$—(A$^2$)$_n$—(Z$^1$—A$^1$)$_m$—Z$^0$—A—OM, R$^2$—(A$^2$)$_n$—(Z$^1$A$^1$)$_m$—OM, R$^2$—(A$^2$)$_n$—OM or R$^2$—(A$^2$)$_{n-1}$—OM, wherein M is one equivalent of a metal, preferably an alkali metal, such as Na or K, are particularly suitable reactive derivatives of the alcohols and phenols mentioned.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenohydrocarbons, such as carbon tetrachloride or tetrachloroethylene, and sulfoxides, such as dimethylsulfoxide or sulfolane. Water-immiscible solvents can at the same time advantageously be used for removal of the water formed during the esterification by azeotropic distillation. An excess of an organic base, for example pyridine, quinoline or triethylamine, may occasionally also be used as the solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are as a rule ended after 15 minutes to 48 hours.

In detail, the reaction conditions for the esterification largely depend on the nature of the starting substances used. Thus, a free carboxylic acid is as a rule reacted with a free alcohol or phenol in the presence of a strong acid, for example a mineral acid, such as hydrochloric acid or sulfuric acid. A preferred reaction procedure is the reaction of an acid anhydride or, in particular, an acid chloride with an alcohol, preferably in a basic medium, important bases being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. Another preferred embodiment of the esterification comprises first converting the alcohol or the phenol into the sodium alcoholate or phenolate or potassium alcoholate or phenolate, for example by treatment with ethanolic sodium hydroxide solution or potassium hydroxide solution, isolating this product and suspending it in acetone or diethyl ether, together with sodium bicarbonate or potassium carbonate, with stirring, and adding a solution of the acid chloride or anhydride in diethyl ether, acetone or DMF to this suspension, advantageously at temperatures between about −25° and +20°.

Dioxane derivatives and dithiane derivatives of the formula I (wherein one of the groups $A^1$ and/or $A^2$ is a 1,3-dioxane-2,5-diyl group or 1,3-dithiane-2,5-diyl group) are advantageously prepared by reacting a corresponding aldehyde, for example of the formula $R^1-A-Z^0-(A^1-Z^1)_m-A^2-CHO$, $R^1-A-Z^0-(A^1)_m-CHO$ or $O=CH-R^2$ (or one of its reactive derivatives), with a corresponding 1,3-diol, for example of the formulae $(HOCH_2)_2CH-(A^2)_{n-2}-R^2$, $(HOCH_2)_2CH-(A^2)_{n-1}-R^2$ or $R^1-A-Z^0-(A^1-Z^1)_m-(A^2)_{n-1}-CH(CH_2OH)_2$ (or one of its reactive derivatives), or a corresponding 1,3-dithiol, preferably in the presence of an inert solvent, such as benzene or toluene, and/or a catalyst, for example a strong acid, such as sulfuric acid or benzene-or p-toluene-sulfonic acid, at temperatures between about 20° and about 150°, preferably between 80° and 120°. Suitable reactive derivatives of the starting substances are, above all, acetals, for example of the formulae $R^1-A-Z^0-(A^1-Z^1)_m-A^2-CH(OR^4)_2$, $R^1-A-Z^0-(A^1)_m-CH(OR^4)_2$, $(R^4O)_2-R^2$, $R^1-A-Z^0-(A^1-Z^1)_m-A_2-CH(CH_2O)_2CH-R^5$ or $R^1-A-Z^o-(A^1)_m-CH(CH_2O)_2CHR^5$, wherein $R^4$ is alkyl with 1-4 C atoms, or two radicals $R^4$ together are also alkylene with 2 or 3 C atoms, and $R^5$ is H, alkyl with 1-4 C atoms or phenyl.

The aldehydes and 1,3-diols or 1,3-dithiols mentioned and their reactive derivatives are known in some cases, and some of them can be prepared without difficulty by standard methods of organic chemistry from compounds which are known from the literature. For example, the aldehydes can be obtained by oxidation of corresponding alcohols or by reduction of corresponding carboxylic acids or their derivatives, the diols can be obtained by reduction of corresponding diesters and the dithiols can be obtained by reacting corresponding dihalides with NaSH.

To prepare nitriles of the formula I (wherein $R^1$ and/or $R^2$ are CN and/or wherein A and/or $A^1$ and/or $A^2$ are substituted by at least one CN group), corresponding acid amides, for example those in which the radical X is replaced by a $CONH_2$ group, can be dehydrated. The amides can be obtained, for example, from corresponding esters or acid halides by reaction with ammonia. Examples of suitable dehydrating agents are inorganic acid chlorides, such as $SOCl_2$, $PCl_3$, $PCl_5$, $POCl_3$, $SO_2Cl_2$ or $COCl_2$, and furthermore $P_2O_5$, $P_2S_5$, $AlCl_3$ (for example as a double compound with NaCl) and aromatic sulfonic acids and sulfonic acid halides. The reaction can be carried out in the presence or absence of an inert solvent at temperatures between about 0° and 150°; examples of possible solvents are bases, such as pyridine or triethylamine, aromatic hydrocarbons, such as benzene, toluene or xylene, or amides, such as DMF.

To prepare the abovementioned nitriles of the formula I, it is also possible to react corresponding acid halides, preferably the chlorides, with sulfamide, advantageously in an inert solvent, such as tetramethylene sulfone, at temperatures between about 80° and 150°, preferably at 120°. After customary working up, the nitriles can be isolated directly.

Nitriles of the formula I wherein A is a 1,4-cyclohexylene group which is substituted by CN can also be obtained by alkylation of acetonitriles of the formula II with 1,5-di-$X^1$-pentane derivatives of the formula III. The acetonitriles can be obtained, for example, from corresponding halides of the formula $E^1-CH_2X^1$ and metal cyanides, and the compounds III can be obtained by reduction of corresponding glutaric acid diesters to give the corresponding diols (III, $X^1=OH$) and, if appropriate, reaction thereof with inorganic halides, such as $SOCl_2$, HBr or HI. The acetonitrile is advantageously first converted into the corresponding carbanion with a strong base, such as NaH, $NaNH_2$, lithium diisopropylamide, piperidide or 2,5-diisopropyl-piperidide or K tert.-butylate, preferably in an inert solvent, for example a hydrocarbon, such as toluene, an ether, such as THF or dioxane, an amide, such as DMF, a sulfoxide, such as dimethyl sulfoxide, or a mixture of such solvents. After adding III (wherein $X^1$ is other than OH), the mixture is advantageously kept at temperatures between 0° and 150° for 0.5 to 16 hours. In contrast, reaction of II with III ($X^1=OH$) is advantageously effected in the presence of azodicarboxylic acid esters/triphenylphosphine in THF at temperatures between about −30° and +30°.

In a completely analogous manner, nitriles or esters of the formula 1 wherein A is a 1,4-cyclohexylene group which is substituted in the 1- or 4-position by CN or —COO-alkyl and which additionally can be substituted by 1-2 F atoms and/or CN groups can be obtained by reacting a nitrile of the formula IV or a corresponding ester compound with a halide of the formula V. The nitriles of the formula IV can be obtained, for example, from corresponding amides of the formula $Q^1-A^3CONH_2$ by dehydration, the esters can be obtained by hydrolysis of the corresponding nitriles and esterification, and the halides of the formula V can be obtained from corresponding alcohols of the formula $Q^2$—OH.

Fluorine compounds of the formula I wherein A is a 1,4-cyclohexylene group which is substituted in the 1- or 4-position by F and which can additionally carry 1 or 2 further substituents can be obtained by treatment of the corresponding hydroxy compounds or bromine or chlorine compounds with a fluorinating agent. Fluorinating agents which can be used are all the compounds known for these exchange reactions, for example diethylaminesulfur trifluoride (J. Org. Chem. 40 (5), 574–8 (1975)). The hydroxy, bromine and chlorine compounds can be obtained, for example, from the corresponding cyclohexene compounds by adding on $H_2O$, HBr or HCl.

Ethers of the formula I (wherein $R^1$ and/or $R^2$ are an alkyl group, in which one or two $CH_2$ groups are replaced by O atoms, and/or wherein $Z^0$ and/or $Z^1$ and/or $Z^2$ are an —$OCH_2$— or a —$CH_2O$— group) can be obtained by etherification of corresponding hydroxy compounds, preferably corresponding phenols, the hydroxy compound advantageously first being converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This product can then be reacted with the corresponding alkyl halide, sulfonate or dialkyl sulfate, advantageously in an inert solvent, such as acetone, 1,2-dimethoxyethane, DMF or dimethylsulfoxide, or an excess of aqueous or aqueous-alcoholic NaOH or KOH, at temperatures between about 20° and 100°.

To prepare compounds of the formula I wherein $R^1$ and/or $R^2$ are SOR or $SO_2R$, corresponding compounds wherein $R^1$ and/or $R^2$ are SR or SOR can be oxidized.

Depending on the chosen reagent and the conditions applied, the starting substances are oxidized to the corresponding sulfoxides or to the corresponding sulfones of the formula I; the reactions are carried out by methods which are known per se from the literature, and the reaction conditions can easily be found in detail in the literature. If the sulfoxides are to be obtained, the corresponding thioethers are oxidized, for example, with hydrogen peroxide, peracids, Cr(VI) compounds, such as chromic acid, nitric acid, nitrous gases, $N_2O_3$, halogens, such as chlorine, hypochlorites, $KMnO_4$, N-bromosuccinimide, 1-chlorobenzotriazole, Ce(IV) compounds, such as $(NH_4)_2Ce(NO_3)_6$, or negatively substituted aromatic diazonium salts, such as o- or p-nitrophenyldiazonium chloride, or electrolytically under relatively mild conditions and at relatively low temperatures (about −80° to +100°). In contrast, if the sulfones are to be obtained, the same oxidizing agents are used under more severe conditions and/or in excess and as a rule at higher temperatures. The usual inert solvents can be present or absent in these reactions. Examples of suitable inert solvents are water, aqueous mineral acids, aqueous alkali metal hydroxide solutions, lower alcohols, such as methanol or ethanol, esters, such as ethyl acetate, ketones, such as acetone, lower carboxylic acids, such as acetic acid, nitriles, such as acetonitrile, hydrocarbons, such as benzene, or chlorinated hydrocarbons, such as chloroform or $CCl_4$.

A preferred oxidizing agent is 30% strength aqueous hydrogen peroxide. This leads to the sulfoxides if the calculated amount is used in solvents such as acetic acid, acetone, ethanol or aqueous sodium hydroxide solution at temperatures between −20° and 100°, and in excess at higher temperatures, preferably in acetic acid or in a mixture of acetic acid and acetic anhydride, leads to the sulfones.

Another preferred oxidizing agent is 3-chloroperbenzoic acid. This as a rule leads to the sulfoxides if the calculated amount is used in solvents such as halogenohydrocarbons at temperatures below 0°, and in excess at temperatures between 0° and room temperature leads to the sulfones.

Another possibility of preparing the sulfoxides comprises treating the thioethers with chlorine, for example in moist benzene or in acetic acid. The dichlorine compounds intermediately formed are very easily converted into the sulfoxides by hydrolysis.

The thioethers are prepared by methods which are known per se, such as are described in the literature (for example in the standard works, such as Houben-Weyl, Methoden der Organischen Chemie (Methods of Organic Chemistry), Georg-Thieme-Verlag, Stuttgart), and in particular under reaction conditions which are known and suitable for the reactions mentioned. The thioethers are preferably obtained by treating corresponding halogen compounds, wherein halogen is chlorine, bromine or iodine, with salts of corresponding mercaptans.

These halogen compounds are either known, or they can be prepared without difficulty by methods which are known per se, analogously to known compounds. Thus, for example, p-substituted halogenobenzene derivatives are accessible by halogenation of the corresponding benzene derivatives. 4-Substituted cyclohexyl halides can be obtained, for example, by reduction of the corresponding 4-substituted cyclohexanones to the 4-substituted cyclohexanols and subsequent substitution by halogen.

In principle all methods which are known for the compounds which carry other substituents instead of the halogen can be applied in the synthesis of the halogen compounds. The expert can deduce the required synthesis methods by routine methods.

To prepare compounds of the formula I wherein A is a 1,4-cyclohexylene group which is substituted in the 1- or 4-position by an alkyl group with 1-5 C atoms, in which one or two non-adjacent $CH_2$ groups are replaced by —S—, —SO— or —$SO_2$—, methods analogous to those for the preparation of the compounds with sulfur-containing groups $R^1$, $R^2$ and/or $R^3$ can be used.

To prepare compounds of the formula I which contain $CF_3$ groups, corresponding carboxylic acids, which can in turn be obtained, for example, by hydrolysis of corresponding nitriles, can be reacted with $SF_4$, advantageously with an excess of $SF_4$, under pressure in the absence or in the presence of an inert solvent, such as cyclohexane or methylene chloride, at temperatures between about 70° and 200°. The reaction times vary between about 2 hours and about 4 days.

To prepare nitriles of the formula I (wherein $R^1$ and/or $R^2$ are CN and/or wherein A and/or $A^1$ and/or $A^2$ are substituted by at least one CN group), it is also possible to react corresponding chlorine or bromine compounds of the formula I (wherein $R^1$ and/or $R^2$ are Cl or Br and/or wherein A is substituted by at least one Cl or Br atom and/or $A^1$ and/or $A^2$ are substituted by at least one chlorine atom) with a cyanide, advantageously with a metal cyanide, such as NaCN, KCN or $Cu_2(CN)_2$, for example in the presence of pyridine, in an inert solvent, such as DMF or N-methylpyrrolidone, at temperatures between 20° and 200°.

A base of the formula I can be converted with an acid into the associated acid addition salt. For this reaction it is possible to use inorganic acids, for example sulfuric acid, nitric acid, hydrogen halide acids, such as hydrochloric acid or hydrobromic acid, phosphoric acids, such as orthophosphoric acid, or sulfamic acid, and furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-mono- and -di-sulfonic acids and laurylsulfuric acid.

Conversely, it is possible to liberate the base of the formula I from an acid addition salt of a compound of the formula I by treatment with a base, for example with a strong inorganic based such as KOH or NaOH.

The salts of this invention are useful in particular for preparation of the compounds of formulae I and II by routine procedures.

The compounds of the formula II can be prepared in a manner corresponding to that for the formula I, by analogous processes.

For example, esters of the formula II ($R^{1'}$ and/or $R^{2'}$=—O—COR and/or —COOR and/or $Z^0$ and/or $Z^{1'}$=—CO—O— or —O—CO—) can be obtained by esterification of corresponding carboxylic acids, for example of the formulae R—COOH, $R^{1'}$—A—COOH, $R^{1'}$—A—$Z^0$—$(A^{1'})_m$—COOH or $R^{1'}$—A—$Z^0$—$(A^{1'}$—$Z^{1'})_m$—$A^{2'}$—COOH (or their reactive derivatives) with alcohols or phenols of the formulae $R^{1'}$—A—$Z^0$—$(A^{1'}$—$Z^{1'})_m$—$(A^{2'})_n$—OH, $R^{2'}$—$(A^{2'})_n$—$(Z^{1'}$—$A^{1'})_m$—$Z^0$—A—OH, $R^{2'}$—$(A^{2'})_n$—$(Z^{1'}$—$A^{1'})_m$—OH, $R^{2'}$—$(A^{2'})_n$—OH or $R^{2'}$—$(A^{2'})_{n-1}$—OH (or their reactive derivatives).

Particularly suitable reactive derivatives of the carboxylic acids mentioned are the acid halides, above all the chlorides and bromides, and furthermore the anhydrides, for example also mixed anhydrides of the formulae $R^{1'}$—A—CO—O—$COCH_3$, $R^{1'}$—A—$Z^0$—$(A^{1'}$—$Z^{1'})_m$—CO—O—$COCH_3$ or $R^{1'}$—A—$Z^0$—$(A^{1'}$—$Z^{1'})_m$—$(A^{2'})_n$—CO—O—$COCH_3$, azides or esters, in particular alkyl esters with 1-4 C atoms in the alkyl group.

Particularly suitable reactive derivatives of the alcohols and phenols mentioned are the corresponding metal alcoholates or phenolates of the formulae $R^{1'}$—A—$Z^0$—$(A^{1'}$—$Z^{1'})_m$—$(A^{2'})_n$—OM, $R^{2'}$—$(A^{2'})_n$—$(Z^{1'}$—$A^{1'})_m$—$Z^0$—A—OM, $R^{2'}$—$(A^{2'})_n$—$(Z^{1'}$—$A^{1'})_m$—OM, $R^{2'}$—$(A^{2'})_n$—OM or $R^{2'}$—$(A^{2'})_{n-1}$—OM, wherein M is one equivalent of a metal, preferably an alkali metal, such as Na or K.

For example, dioxane derivatives or dithiane derivatives of the formula II (wherein one of the groups $A^{1'}$ and/or $A^{2'}$ is a 1,3-dioxane-2,5-diyl group or 1,3-dithiane-2,5-diyl group) can advantageously be prepared by reacting a corresponding aldehyde, for example of the formula $R^{1'}$—A—$Z^0$—$(A^{1'}$—$Z^{1'})_m$—$A^{2'}$—CHO, $R^{1'}$—A—$Z^0$—$(A^{1'})_m$—CHO or O=CH—$R^{2'}$ (or one of its reactive derivatives) with a corresponding 1,3-diol, for example of the formula $(HOCH_2)_2$—CH—$(A^{2'})_{n-2}$—$R^{2'}$, $(HOCH_2)_2CH$—$(A^{2'})_{n-1}$—$R^{2'}$ or $R^{1'}$—A—$Z^0$—$(A^{1'}$—$Z^{1'})_m$—$(A^{2'})_{n-1}$—$CH(CH_2OH)_2$ (or one of its reactive derivatives) or a corresponding 1,3-dithiol (or one of its reactive derivatives), preferably in the presence of an inert solvent, such as benzene or toluene, and/or a catalyst, for example a strong acid, such as sulfuric acid or benzene- or p-toluenesulfonic acid, at temperatures between about 20° and about 150°, preferably between 80° and 120°. Suitable reactive derivatives of the starting substances are, above all, acetals, for example of the formulae $R^{1'}$—A—$Z^0$—$(A^{1'}$—$Z^{1'})_m$—$A^{2'}$—$CH(OR^4)_2$, $R^{1'}$—A—$Z^0$—$(A^{1'})_m$—$CH(OR^4)_2$, $(R^4O)_2$—$R^{2'}$, $R^{1'}$—A—$Z^0$—$(A^{1'}$—$Z^{1'})_m$—$A^{2'}$—$CH(CH_2O)_2CH$—$R^5$ or $R^{1'}$—A—$Z^0$—$(A^{1'})_m$—$CH(CH_2O)_2CHR^5$, wherein $R^4$ is alkyl with 1-4 C atoms, or two radicals $R^4$ together are also alkylene with 2 or 3 C atoms, and $R^5$ is H, alkyl with 1-4 C atoms or phenyl.

Nitriles of the formula II wherein A is a 1,4-cyclohexylene group which is substituted by CN can also be obtained by alkylation of acetonitriles of the formula II with 1,5-di-$X^1$-pentane derivatives of the formula III. The acetonitriles can be obtained, for example, from corresponding halides of the formula $E^1$—$CH_2X^1$ and metal cyanides, and the compounds III can be obtained by reduction of corresponding glutaric acid diesters to give the corresponding diols (III, $X^1$=OH) and, if appropriate, reaction thereof with inorganic halides, such as $SOCl_2$, HBr or HI. The acetonitrile is advantageously first converted into the corresponding carbanion with a strong base, such as NaH, $NaNH_2$, lithium diisopropylamide, piperidide or 2,5-diisopropyl-piperidide or K tert.-butylate, preferably in an inert solvent, for example a hydrocarbon, such as toluene, an ether, such as THF or dioxane, an amide, such as DMF, a sulfoxide, such as dimethyl sulfoxide, or a mixture of such solvents. After addition of III (wherein $X^1$ is other than OH), the mixture is advantageously kept at temperatures between 0° and 150° for 0.5 to 16 hours. In contrast, reaction of II with III ($X^1$=OH) is advantageously effected in the presence of azodicarboxylic acid esters/triphenylphosphine in THF at temperatures between about $-30°$ and $+30°$.

In a completely analogous manner, nitriles of the formula II wherein A is a 1,4-cyclohexylene group which is substituted in the 1- or 4-position by CN and which can additionally be substituted by 1 or 2 F atoms and/or CN groups can be obtained by reacting a nitrile of the formula IV with a halide of the formula V. The nitriles of the formula IV can be obtained, for example, from corresponding amides of the formula $Q^1$—$A^{3'}$—$CONH_2$ by dehydration, and the halides of the formula V can be obtained from corresponding alcohols of the formula $Q^2$—OH.

Preferred intermediates for the preparation of the compounds of the formulae I and II according to the invention are the cyclohexanones of the formulae (A) and (B)

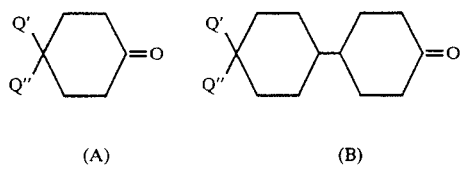

(A)   (B)

wherein

Q' is an alkyl group with 3-15 C atoms, it also being possible for one or two non-adjacent CH$_2$ groups to be replaced by a grouping from the group comprising —O—, —CO—, —S—, —SO— and —SO$_2$—, Q" is COOR$^0$, OR$^0$, SR$^0$, SOR$^0$, SO$_2$R$^0$, R$^0$, CF$_3$, CCl$_3$, CHF$_2$, CN, CHO, F, Cl or Br and R$^0$ is an alkyl group with 1-3 C atoms, and reactive derivatives thereof.

Particularly preferred intermediates are those compounds of the formulae (A) and (B) wherein Q' is a straight-chain alkyl group with 4-9 C atoms and Q" is —CN, —CHO, —CF$_3$, —CH$_3$, OCH$_3$—, —SCH$_3$, —SOCH$_3$, —SO$_2$CH$_3$, —COOCH$_3$ or F, in particular —CN, —CH$_3$ or F.

The compounds of the formulae (A) and (B) are prepared by methods which are known per se, such as are described in the literature (for example in the standard works, such as Houben-Weyl, Methoden der Organischen Chemie (Methods of Organic Chemistry), Georg-Thieme-Verlag, Stuttgart), and in particular under reaction conditions which are known and suitable for the reactions mentioned. It is also possible to utilize the variants which are known per se and are not mentioned here in more detail.

The compounds of the formulae (A) and (B) can be converted, for example, into ester derivatives of the formulae I and II by reduction of the carbonyl group and subsequent esterification. Ether derivatives of the formulae I and II can be obtained by etherification of the alcohols obtained from (A) and (B) by reduction.

A large number of compounds of the formulae I and II can be obtained by Grignard reaction with the cyclohexanones of the formulae (A) and (B) and subsequent reduction. Wittig reaction with 2-substituted 1-bromoethane derivatives/triphenylphosphine and subsequent hydrogenation gives a large number of compounds of the formulae I and II with —CH$_2$CH$_2$— groups between two ring structures.

The liquid crystal phases according to the invention comprise 2 to 15, preferably 3 to 12, components, at least one of which is a compound of the formula I and/or II. The other constituents are preferably chosen from the nematic or nematogenic substances, in particular the known substances from the classes of azoxybenzenes, benzylideneanilines, biphenyls, terphenyls, phenyl- or cyclohexyl-benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenyl-or cyclohexyl-pyrimidines, phenyl- or cyclohexyl-dioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolanes and substituted cinnamic acids.

Phases according to the invention which, besides at least one compound of the formula I, contain at least one compound of the formula II are furthermore preferred.

The most important compounds which are suitable as constituents of such liquid crystal phases can be characterized by the formula Ix $$R^6-L-G-E-R^7 \qquad \text{IX}$$

wherein L and E are each a carbocyclic or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaohthalene, quinazoline and tetrahydroquinazoline, G is

| G | —CH=CH— | —N(O)=N— |
|---|---|---|
|   | —CH=CY— | —CH=N(O)— |
|   | —C≡C— | —CH$_2$—CH$_2$— |
|   | —CO—O— | —CH$_2$—O— |
|   | —CO—S— | —CH$_2$—S— |
|   | —CH=N— | —COO—Phe—COO— | or a C-C single bond,

Y is halogen, preferably chlorine, or —CN and R$^6$ and R$^7$ are alkyl, alkoxy, alkanoyloxy or alkoxycarbonyloxy with up to 18, preferably up to 8, carbon atoms, or one of these radicals is also CN, NC, NO$_2$, CF$_3$, F, Cl or Br.

In most of these compounds, R$^6$ and R$^7$ are different, one of these radicals usually being an alkyl or alkoxy group. However, other variants of the envisaged substituents can also be used. Many such substances or mixtures thereof are commercially available. All these substances can be obtained by methods which are known from the literature.

The phases according to the invention contain about 0.1 to 99%, preferably 10 to 95%, of one or more compounds of the formula I and/or II. Liquid crystal phases according to the invention containing 0.1–40%, preferably 0.5–30%, of one or more compounds of the formula I and/or II are furthermore preferred.

The phases according to the invention are prepared in a manner which is customary per se. As a rule, the components are dissolved in one another, advantageously at elevated temperature.

The liquid crystal phases according to the invention can be modified by suitable additives so that they can be used in all the types of liquid crystal display elements which have hitherto been disclosed.

Such additives are known to the expert and are described in detail in the literature. For example, it is possible to add conductive salts, preferably ethyldimethyl-dodecyl-ammonium 4-hexyloxybenzoate, tetrabutylammonium tetraphenyl boranate or complex salts of crown ethers (compare, for example, I. Haller et al., Mol. Cryst.Liq.Cryst. Volume 24, pages 249-258 (1973)) to improve the conductivity, dichroic dyestuffs to prepare coloured guest/host systems or substances for modifying the dielectric anisotropy, the viscosity and/or the orientation of the nematic phases. Such substances are described, for example, in German Offenlegungsschriften 2,209,127, 2,240,864, 2,321,632, 2,338,281, 2,450,088, 2,637,430, 2,853,728 and 2,902,177.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials. Of course, the compounds of this invention can also be used to prepare one another using the reactions discussed above and other conventional methods.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. is the melting point and c.p. is the clear point of a liquid crystal substance.

"Customary working up" means: water is added, the mixture is extracted with methylene chloride, the organic phase is separated off, dried and evaporated and the product is purified by crystallization and/or chromatography.

EXAMPLE 1

62.5 ml (0.1 mole) of a 1.6M solution of n-butyllithium in hexane and 33.1 g (0.1 mole) of 4-(4-cyanocyclohexyl)-4'-pentylbiphenyl (obtainable by Grignard reaction of 4-bromo-4'-pentyl-biphenyl with 4-(4,5-dihydro-4,4-dimethyl-2-oxazolyl)-cyclohexanone (J. Org. Chem. 39 (18), 2787–93 (1974)), detachment of water and simultaneous removal of the oxazolyl protective group by boiling with ethanolic $H_2SO_4$, hydrogenation of the double bond and subsequent conversion of the ester into the nitrile) in 40 ml of THF are successively added dropwise to 10.1 g (0.1 mole) of diisopropylamine in 70 ml of THF at $-10°$, with exclusion of moisture and under a nitrogen atmosphere. The reaction mixture is then stirred for 20 minutes. 13.5 g (0.11 mole) of 1-bromopropane are then added, also at $-10°$, and the mixture is subsequently stirred at room temperature for a further 20 minutes. After customary working up, 4-(4-cyano-4-propylcyclohexyl)-4'-pentylbiphenyl is obtained.

The following compounds are prepared analogously:
4-(4-cyano-4-propylcyclohexyl)-4'-ethylbiphenyl
4-(4-cyano-4-propylcyclohexyl)-4'-propylbiphenyl
4-(4-cyano-4-propylcyclohexyl)-4'-butylbiphenyl
4-(4-cyano-4-propylcyclohexyl)-4'-heptylbiphenyl
4-(4-cyano-4-butylcyclohexyl)-4'-ethylbiphenyl
4-(4-cyano-4-butylcyclohexyl)-4'-propylbiphenyl
4-(4-cyano-4-butylcyclohexyl)-4'-butylbiphenyl
4-(4-cyano-4-butylcyclohexyl)-4'-pentylbiphenyl
4-(4-cyano-4-butylcyclohexyl)-4'-heptylbiphenyl
4-(4-cyano-4-pentylcyclohexyl)-4'-ethylbiphenyl
4-(4-cyano-4-pentylcyclohexyl)-4'-propylbiphenyl
4-(4-cyano-4-pentylcyclohexyl)-4'-butylbiphenyl
4-(4-cyano-4-pentylcyclohexyl)-4'-pentylbiphenyl
4-(4-cyano-4-pentylcyclohexyl)-4'-heptylbiphenyl
4-(4-cyano-4-heptylcyclohexyl)-4'-ethylbiphenyl
4-(4-cyano-4-heptylcyclohexyl)-4'-propylbiphenyl
4-(4-cyano-4-heptylcyclohexyl)-4'-butylbiphenyl
4-(4-cyano-4-heptylcyclohexyl)-4'-pentylbiphenyl
4-(4-cyano-4-heptylcyclohexyl)-4'-heptylbiphenyl
4-(4-cyano-4-nonylcyclohexyl)-4'-ethylbiphenyl
4-(4-cyano-4-nonylcyclohexyl)-4'-propylbiphenyl
4-(4-cyano-4-nonylcyclohexyl)-4'-butylbiphenyl
4-(4-cyano-4-nonylcyclohexyl)-4'-pentylbiphenyl
4-(4-cyano-4-nonylcyclohexyl)-4'-heptylbiphenyl

EXAMPLE 2

55 ml of a 1M solution of diisobutyl-aluminium hydride (DIBAH) in n-hexane are added to a solution of 8.6 g (0.05 mole) of 4-(4-cyano-4-propyl-cyclohexyl)-4'-n-pentylbiphenyl (Example 1) in 100 ml of hexane at 0°, under a nitrogen atmosphere and with exclusion of moisture. The mixture is stirred at room temperature for one hour and 5 ml of methanol are then carefully added. The reaction mixture is poured into 200 ml of ice-cold 10% $H_2SO_4$ and stirred for 30 minutes. The organic phase is then separated off and the aqueous phase is extracted twice more with hexane. The combined organic phases are neutralised with $NaHCO_3$ solution and then dried. Purification by chromatography gives 4-(4-formyl-4-propylcyclohexyl)-4'-pentylbiphenyl.

The following compounds are prepared analogously:
4-(4-formyl-4-n-propylcyclohexyl)-4'-n-ethylbiphenyl
4-(4-formyl-4-n-propylcyclohexyl)-4'-n-propylbiphenyl
4-(4-formyl-4-n-propylcyclohexyl)-4'-n-butylbiphenyl
4-(4-formyl-4-n-propylcyclohexyl)-4'-n-heptylbiphenyl
4-(4-formyl-4-n-butylcyclohexyl)-4'-n-ethylbiphenyl
4-(4-formyl-4-n-butylcyclohexyl)-4'-n-propylbiphenyl
4-(4-formyl-4-n-butylcyclohexyl)-4'-n-butylbiphenyl
4-(4-formyl-4-n-butylcyclohexyl)-4'-n-pentylbiphenyl
4-(4-formyl-4-n-butylcyclohexyl)-4'-n-heptylbiphenyl
4-(4-formyl-4-n-pentylcyclohexyl)-4'-n-ethylbiphenyl
4-(4-formyl-4-n-pentylcyclohexyl)-4'-n-propylbiphenyl
4-(4-formyl-4-n-pentylcyclohexyl)-4'-n-butylbiphenyl
4-(4-formyl-4-n-pentylcyclohexyl)-4'-n-pentylbiphenyl
4-(4-formyl-4-n-pentylcyclohexyl)-4'-n-heptylbiphenyl
4-(4-formyl-4-n-heptylcyclohexyl)-4'-n-ethylbiphenyl
4-(4-formyl-4-n-heptylcyclohexyl)-4'-n-propylbiphenyl
4-(4-formyl-4-n-heptylcyclohexyl)-4'-n-butylbiphenyl
4-(4-formyl-4-n-heptylcyclohexyl)-4'-n-pentylbiphenyl
4-(4-formyl-4-n-heptylcyclohexyl)-4'-n-heptylbiphenyl

EXAMPLE 3

A mixture of 3.7 g (0.01 mole) of 4-(4-formyl-4-propylcyclohexyl)-4'-pentylbiphenyl (Example 2), 40 ml of diethylene glycol, 15 ml of 90% hydrazine hydrate and 5.5 g of potassium hydroxide is heated and the hydrazine and water are distilled off until the temperature has risen to about 230° C. The reaction mixture is then boiled for 12 hours and, when cold, 200 ml of water are subsequently added. After customary working up, 4-(4-methyl-4-propylcyclohexyl)-4'-pentylbiphenyl is obtained.

The following compounds are prepared analogously:
4-(4-methyl-4-n-propylcyclohexyl)-4'-n-ethylbiphenyl
4-(4-methyl-4-n-propylcyclohexyl)-4'-n-propylbiphenyl
4-(4-methyl-4-n-propylcyclohexyl)-4'-n-butylbiphenyl
4-(4-methyl-4-n-propylcyclohexyl)-4'-n-heptylbiphenyl
4-(4-methyl-4-n-butylcyclohexyl)-4'-n-ethylbiphenyl
4-(4-methyl-4-n-butylcyclohexyl)-4'-n-propylbiphenyl
4-(4-methyl-4-n-butylcyclohexyl)-4'-n-butylbiphenyl 4-(4-methyl-4-n-butylcyclohexyl)-4'-n-pentylbiphenyl
4-(4-methyl-4-n-butylcyclohexyl)-4'-n-heptylbiphenyl
4-(4-methyl-4-n-pentylcyclohexyl)-4'-n-ethylbiphenyl
4-(4-methyl-4-n-pentylcyclohexyl)-4'-n-propylbiphenyl
4-(4-methyl-4-n-pentylcyclohexyl)-4'-n-butylbiphenyl
4-(4-methyl-4-n-pentylcyclohexyl)-4'-n-pentylbiphenyl
4-(4-methyl-4-n-pentylcyclohexyl)-4'-n-heptylbiphenyl
4-(4-methyl-4-n-heptylcyclohexyl)-4'-n-ethylbiphenyl
4-(4-methyl-4-n-heptylcyclohexyl)-4'-n-propylbiphenyl
4-(4-methyl-4-n-heptylcyclohexyl)-4'-n-butylbiphenyl
4-(4-methyl-4-n-heptylcyclohexyl)-4'-n-pentylbiphenyl
4-(4-methyl-4-n-heptylcyclohexyl)-4'-n-heptylbiphenyl

EXAMPLE 4

4-(4-Cyano-4-propylcyclohexyl)-4'-(4-pentylcyclohexyl)-biphenyl is obtained from 4-(4-cyanocyclohexyl)-4'-(4-pentylcyclohexyl)-biphenyl (obtainable from 4-bromo-4'-(4-pentylcyclohexyl)-biphenyl analogously to Example 1) and 1-bromopropane analogously to Example 1.

The following compounds are prepared analogously:
4-(4-cyano-4-propylcyclohexyl)-4'-(4-ethylcyclohexyl)-biphenyl
4-(4-cyano-4-propylcyclohexyl)-4'-(4-propylcyclohexyl)biphenyl
4-(4-cyano-4-propylcyclohexyl)-4'-(4-butylcyclohexyl)-biphenyl
4-(4-cyano-4-propylcyclohexyl)-4'-(4-heptylcyclohexyl)biphenyl
4-(4-cyano-4-butylcyclohexyl)-4'-(4-ethylcyclohexyl)-biphenyl
4-(4-cyano-4-butylcyclohexyl)-4'-(4-propylcyclohexyl)-biphenyl
4-(4-cyano-4-butylcyclohexyl)-4'-(4-butylcyclohexyl)-biphenyl
4-(4-cyano-4-butylcyclohexyl)-4'-(4-pentylcyclohexyl)-biphenyl
4-(4-cyano-4-butylcyclohexyl)-4'-(4-heptylcyclohexyl)-biphenyl
4-(4-cyano-4-pentylcyclohexyl)-4'-(4-ethylcyclohexyl)-biphenyl
4-(4-cyano-4-pentylcyclohexyl)-4'-(4-propylcyclohexyl)biphenyl
4-(4-cyano-4-pentylcyclohexyl)-4'-(4-butylcyclohexyl)-biphenyl
4-(4-cyano-4-pentylcyclohexyl)-4'-(4-pentylcyclohexyl)biphenyl
4-(4-cyano-4-pentylcyclohexyl)-4'-(4-heptylcyclohexyl)biphenyl
4-(4-cyano-4-heptylcyclohexyl)-4'-(4-ethylcyclohexyl)-biphenyl
4-(4-cyano-4-heptylcyclohexyl)-4'-(4-propylcyclohexyl)biphenyl
4-(4-cyano-4-heptylcyclohexyl)-4'-(4-butylcyclohexyl)-biphenyl
4-(4-cyano-4-heptylcyclohexyl)-4'-(4-pentylcyclohexyl)biphenyl
4-(4-cyano-4-heptylcyclohexyl)-4'-(4-heptylcyclohexyl)biphenyl

EXAMPLE 5

4-(4-Formyl-4-propylcyclohexyl)-4'-(4-pentylcyclohexyl)-biphenyl is obtained from 4-(4-cyano-4-propylcyclohexyl)-4'-(4-pentylcyclohexyl)-biphenyl (Example 4) analogously to Example 2.

The following compounds are prepared analogously:
4-(4-formyl-4-propylcyclohexyl)-4'-(4-ethylcyclohexyl)biphenyl
4-(4-formyl-4-propylcyclohexyl)-4'-(4-propylcyclohexyl)biphenyl
4-(4-formyl-4-propylcyclohexyl)-4'-(4-butylcyclohexyl)biphenyl
4-(4-formyl-4-propylcyclohexyl)-4'-(4-heptylcyclohexyl)biphenyl
4-(4-formyl-4-butylcyclohexyl)-4'-(4-ethylcyclohexyl)-biphenyl
4-(4-formyl-4-butylcyclohexyl)-4'-(4-propylcyclohexyl)biphenyl
4-(4-formyl-4-butylcyclohexyl)-4'-(4-butylcyclohexyl)-biphenyl
4-(4-formyl-4-butylcyclohexyl)-4'-(4-pentylcyclohexyl)biphenyl
4-(4-formyl-4-butylcyclohexyl)-4'-(4-heptylcyclohexyl)biphenyl
4-(4-formyl-4-pentylcyclohexyl)-4'-(4-ethylcyclohexyl)biphenyl
4-(4-formyl-4-pentylcyclohexyl)-4'-(4-propylcyclohexyl)biphenyl
4-(4-formyl-4-pentylcyclohexyl)-4'-(4-butylcyclohexyl)biphenyl
4-(4-formyl-4-pentylcyclohexyl)-4'-(4-pentylcyclohexyl)biphenyl
4-(4-formyl-4-pentylcyclohexyl)-4'-(4-heptylcyclohexyl)biphenyl
4-(4-formyl-4-heptylcyclohexyl)-4'-(4-ethylcyclohexyl)biphenyl
4-(4-formyl-4-heptylcyclohexyl)-4'-(4-propylcyclohexyl)biphenyl
4-(4-formyl-4-heptylcyclohexyl)-4'-(4-butylcyclohexyl)biphenyl
4-(4-formyl-4-heptylcyclohexyl)-4'-(4-pentylcyclohexyl)biphenyl
4-(4-formyl-4-heptylcyclohexyl)-4'-(4-heptylcyclohexyl)biphenyl

EXAMPLE 6

4-(4-Methyl-4-propylcyclohexyl)-4'-(4-pentylcyclohexyl)-biphenyl is obtained from 4-(4-formyl-4-propylcyclohexyl)-4'-(4-pentylcyclohexyl)-biphenyl (Example 5) analogously to Example 3.

The following compounds are prepared analogously:
4-(4-methyl-4-propylcyclohexyl)-4'-(4-ethylcyclohexyl)biphenyl
4-(4-methyl-4-propylcyclohexyl)-4'-(4-propylcyclohexyl)biphenyl
4-(4-methyl-4-propylcyclohexyl)-4'-(4-butylcyclohexyl)biphenyl
4-(4-methyl-4-propylcyclohexyl)-4'-(4-heptylcyclohexyl)biphenyl
4-(4-methyl-4-butylcyclohexyl)-4'-(4-ethylcyclohexyl)-biphenyl
4-(4-methyl-4-butylcyclohexyl)-4'-(4-propylcyclohexyl)biphenyl
4-(4-methyl-4-butylcyclohexyl)-4'-(4-butylcyclohexyl)-biphenyl
4-(4-methyl-4-butylcyclohexyl)-4'-(4-pentylcyclohexyl)biphenyl
4-(4-methyl-4-butylcyclohexyl)-4'-(4-heptylcyclohexyl)biphenyl
4-(4-methyl-4-pentylcyclohexyl)-4'-(4-ethylcyclohexyl)biphenyl
4-(4-methyl-4-pentylcyclohexyl)-4'-(4-propylcyclohexyl)biphenyl
4-(4-methyl-4-pentylcyclohexyl)-4'-(4-butylcyclohexyl)biphenyl 4-(4-methyl-4-pentylcyclohexyl)-4'-(4-pentylcyclohexyl)biphenyl 4-(4-methyl-4-pentylcyclohexyl)-4'-(4-heptylcyclohexyl)biphenyl 4-(4-methyl-4-heptylcyclohexyl)-4'-(4-ethylcyclohexyl)biphenyl 4-(4-methyl-4-heptylcyclohexyl)-4'-(4-propylcyclohexyl)biphenyl 4-(4-methyl-4-heptylcyclohexyl)-4'-(4-butylcyclohexyl)biphenyl 4-(4-methyl-4-heptylcyclohexyl)-4'-(4-pentylcyclohexyl)biphenyl 4-(4-methyl-4-heptylcyclohexyl)-4'-(4-heptylcyclohexyl)biphenyl

EXAMPLE 7

62.5 ml (0.1 mole) of a 1.6M solution of n-butyllithium in hexane and 36.5 g (0.1 mole) of 1-(p-(4-cyanocyclohexyl)-phenyl)-2-(trans-4-pentylcyclohexyl)ethane [obtainable by Friedel-Crafts acylation of benzene with trans-4-pentylcyclohexylacetyl chloride, reduction of the carbonyl group by a Wolff-Kishner reaction, bromination of the aromatic ring in the p-position and subsequent Grignard reaction of the resulting 1-(p-bromophenyl)-2-(trans-4-pentylcyclohexyl)-ethane with 4-(4,5-dihydro-4,4-dimethyl-2-oxazoyl)-cyclohexanone, detachment of water, with simultaneous removal of the oxazolyl protective group, by boiling with ethanolic $H_2SO_4$, hydrogenation of the double bond and conversion of the ethyl ester into the nitrile] in 50 ml of THF are added dropwise in succession to 10.1 g (0.1 mole) of diisopropylamine in 100 ml of THF at $-10°$ with the exclusion of moisture and under a nitrogen atmosphere. The reaction mixture is stirred for 20 minutes. 16.6 g (0.11 mole) of bromopentane are then added at $-10°$ and the mixture is subsequently stirred at room temperature for a further 20 minutes. After customary working up, 1-[p-(4-cyano-4-pentylcyclohexyl)-phenyl]-2-(trans-4-pentyl-cyclohexyl)ethane is obtained.

The following compounds are prepared analogously:

1-[p-(4-cyano-4-pentylcyclohexyl)-phenyl]-2-(trans-4-ethylcyclohexyl)-ethane

1-[p-(4-cyano-4-pentylcyclohexyl)-phenyl]-2-(trans-4-propylcyclohexyl)-ethane

1-[p-(4-cyano-4-pentylcyclohexyl)-phenyl]-2-(trans-4-butylcyclohexyl)-ethane

1-[p-(4-cyano-4-pentylcyclohexyl)-phenyl]-2-(trans-4-heptylcyclohexyl)-ethane

1-[p-(4-cyano-4-heptylcyclohexyl)-phenyl]-2-(trans-4-ethylcyclohexyl)-ethane

1-[p-(4-cyano-4-heptylcyclohexyl)-phenyl]-2-(trans-4-propylcyclohexyl)-ethane

1-[p-(4-cyano-4-heptylcyclohexyl)-phenyl]-2-(trans-4-butylcyclohexyl)-ethane

1-[p-(4-cyano-4-heptylcyclohexyl)-phenyl]-2-(trans-4-pentylcyclohexyl)-ethane

1-[p-(4-cyano-4-heptylcyclohexyl)-phenyl]-2-(trans-4-heptylcyclohexyl)-ethane

1-[p-(4-cyano-4-butylcyclohexyl)-phenyl]-2-(trans-4-ethylcyclohexyl)-ethane

1-[p-(4-cyano-4-butylcyclohexyl)-phenyl]-2-(trans-4-propylcyclohexyl)-ethane

1-[p-(4-cyano-4-butylcyclohexyl)-phenyl]-2-(trans-4-butylcyclohexyl)-ethane

1-[p-(4-cyano-4-butylcyclohexyl)-phenyl]-2-(trans-4-pentylcyclohexyl)-ethane

1-[p-(4-cyano-4-butylcyclohexyl)-phenyl]-2-(trans-4-heptylcyclohexyl)-ethane

1-[p-(4-cyano-4-propylcyclohexyl)-phenyl]-2-(trans-4-ethylcyclohexyl)-ethane

1-[p-(4-cyano-4-propylcyclohexyl)-phenyl]-2-(trans-4-propylcyclohexyl)-ethane

1-[p-(4-cyano-4-propylcyclohexyl)-phenyl]-2-(trans-4-butylcyclohexyl)-ethane

1-[p-(4-cyano-4-propylcyclohexyl)-phenyl]-2-(trans-4-pentylcyclohexyl)-ethane

1-[p-(4-cyano-4-propylcyclohexyl)-phenyl]-2-(trans-4-heptylcyclohexyl)-ethane

1-[p-(4-cyano-4-ethylcyclohexyl)-phenyl]-2-(trans-4-ethylcyclohexyl)-ethane

1-[p-(4-cyano-4-ethylcyclohexyl)-phenyl]-2-(trans-4-propylcyclohexyl)-ethane

1-[p-(4-cyano-4-ethylcyclohexyl)-phenyl]-2-(trans-4-butylcyclohexyl)-ethane

1-[p-(4-cyano-4-ethylcyclohexyl)-phenyl]-2-(trans-4-pentylcyclohexyl)-ethane

1-[p-(4-cyano-4-ethylcyclohexyl)-phenyl]-2-trans-4-heptylcyclohexyl)-ethane

EXAMPLE 8

1-[p-(4-Formyl-4-pentylcyclohexyl)-phenyl]-2-(trans-4-pentylcyclohexyl)-ethane is obtained from 1-[p-( 4-cyano-4-pentylcyclohexyl)-phenyl]-2-(trans-4-pentylcyclohexyl)-ethane (Example 7) analogously to Example 2.

The following compounds are prepared analogously:

1-[p-(4-formyl-4-pentylcyclohexyl)-phenyl]-2-(trans-4-ethylcyclohexyl)-ethane

1-[p-(4-formyl-4-pentylcyclohexyl)-phenyl]-2-(trans-4-propylcyclohexyl)-ethane

1-[p-(4-formyl-4-pentylcyclohexyl)-phenyl]-2-(trans-4-butylcyclohexyl)-ethane

1-[p-(4-formyl-4-pentylcyclohexyl)-phenyl]-2-(trans-4-heptylcyclohexyl)-ethane

1-[p-(4-formyl-4-heptylcyclohexyl)-phenyl]-2-(trans-4-ethylcyclohexyl)-ethane

1-[p-(4-formyl-4-heptylcyclohexyl)-phenyl]-2-(trans-4-propylcyclohexyl)-ethane

1-[p-(4-formyl-4-heptylcyclohexyl)-phenyl]-2-(trans-4-butylcyclohexyl)-ethane

1-[p-(4-formyl-4-heptylcyclohexyl)-phenyl]-2-(trans-4-pentylcyclohexyl)-ethane

1-[p-(4-formyl-4-heptylcyclohexyl)-phenyl]-2-(trans-4-heptylcyclohexyl)-ethane

1-[p-(4-formyl-4-butylcyclohexyl)-phenyl]-2-(trans-4-ethylcyclohexyl)-ethane

1-[p-(4-formyl-4-butylcyclohexyl)-phenyl]-2-(trans-4-propylcyclohexyl)-ethane

1-[p-(4-formyl-4-butylcyclohexyl)-phenyl]-2-(trans-4-butylcyclohexyl)-ethane

1-[p-(4-formyl-4-butylcyclohexyl)-phenyl]-2-(trans-4-pentylcyclohexyl)-ethane

1-[p-(4-formyl-4-butylcyclohexyl)-phenyl]-2-(trans-4-heptylcyclohexyl)-ethane

1-[p-(4-formyl-4-propylcyclohexyl)-phenyl]-2-(trans-4-ethylcyclohexyl)-ethane

1-[p-(4-formyl-4-propylcyclohexyl)-phenyl]-2-(trans-4-propylcyclohexyl)-ethane

1-[p-(4-formyl-4-propylcyclohexyl)-phenyl]-2-(trans-4-butylcyclohexyl)-ethane

1-[p-(4-formyl-4-propylcyclohexyl)-phenyl]-2-(trans-4-pentylcyclohexyl)-ethane

1-[p-(4-formyl-4-propylcyclohexyl)-phenyl]-2-(trans-4-heptylcyclohexyl)-ethane

EXAMPLE 9

A mixture of 4.4 g (0.01 mole) of 1-[p-(4-formyl-4-pentylcyclohexyl)-phenyl]-2-(trans-4-pentyl-cyclohexyl)ethane (Example 8), 40 ml of diethylene glycol, 15 ml of 90% hydrazine and 5.5 g of potassium hydroxide is heated and the hydrazine and water are distilled off until the temperature has risen to about 230° C. The reaction mixture is then boiled for 12 hours and, when cold, 200 ml of water are subsequently added. After customary working up, 1-[p-(4-methyl-4-pentylcyclohexyl)-phenyl]-2-(trans-4-pentylcyclohexyl)-ethane is obtained.

The following compounds are prepared analogously:
1-[p-(4-methyl-4-pentylcyclohexyl)-phenyl]-2-(trans-4-ethylcyclohexyl)-ethane
1-[p-(4-methyl-4-pentylcyclohexyl)-phenyl]-2-(trans-4-propylcyclohexyl)-ethane
1-[p-(4-methyl-4-pentylcyclohexyl)-phenyl]-2-(trans-4-butylcyclohexyl)-ethane
1-[p-(4-methyl-4-pentylcyclohexyl)-phenyl]-2-(trans-4-heptylcyclohexyl)-ethane
1-[p-(4-methyl-4-heptylcyclohexyl)-phenyl]-2-(trans-4-ethylcyclohexyl)-ethane
1-[p-(4-methyl-4-heptylcyclohexyl)-phenyl]-2-(trans-4-propylcyclohexyl)-ethane
1-[p-(4-methyl-4-heptylcyclohexyl)-phenyl]-2-(trans-4-butylcyclohexyl)-ethane
1-[p-(4-methyl-4-heptylcyclohexyl)-phenyl]-2-(trans-4-pentylcyclohexyl)-ethane
1-[p-(4-methyl-4-heptylcyclohexyl)-phenyl]-2-(trans-4-heptylcyclohexyl)-ethane
1-[p-(4-methyl-4-butylcyclohexyl)-phenyl]-2-(trans-4-ethylcyclohexyl)-ethane
1-[p-(4-methyl-4-butylcyclohexyl)-phenyl]-2-(trans-4-propylcyclohexyl)-ethane
1-[p-(4-methyl-4-butylcyclohexyl)-phenyl]-2-(trans-4-butylcyclohexyl)-ethane
1-[p-(4-methyl-4-butylcyclohexyl)-phenyl]-2-(trans-4-pentylcyclohexyl)-ethane
1-[p-(4-methyl-4-butylcyclohexyl)-phenyl]-2-(trans-4-heptylcyclohexyl)-ethane
1-[p-(4-methyl-4-propylcyclohexyl)-phenyl]-2-(trans-4-ethylcyclohexyl)-ethane
1-[p-(4-methyl-4-propylcyclohexyl)-phenyl]-2-(trans-4-propylcyclohexyl)-ethane
1-[p-(4-methyl-4-propylcyclohexyl)-phenyl]-2-(trans-4-butylcyclohexyl)-ethane
1-[p-(4-methyl-4-propylcyclohexyl)-phenyl]-2-(trans-4-pentylcyclohexyl)-ethane
1-[p-(4-methyl-4-propylcyclohexyl)-phenyl]-2-(trans-4-heptylcyclohexyl)-ethane
1-[p-(4-methyl-4-ethylcyclohexyl)-phenyl]-2-(trans-4-ethylcyclohexyl)-ethane
1-[p-(4-methyl-4-ethylcyclohexyl)-phenyl]-2-(trans-4-propylcyclohexyl)-ethane
1-[p-(4-methyl-4-ethylcyclohexyl)-phenyl]-2-(trans-4-butylcyclohexyl)-ethane
1-[p-(4-methyl-4-ethylcyclohexyl)-phenyl]-2-(trans-4-pentylcyclohexyl)-ethane
1-[p-(4-methyl-4-ethylcyclohexyl)-phenyl]-2-(trans-4-heptylcyclohexyl)-ethane

EXAMPLE 10

1 g of 4-dimethylaminopyridine and 30.3 g (0.1 mole) of 4-cyano-4-heptyl-4'-hydroxybicyclohexane (obtainable from 4-(1,4-dioxaspiro[4,5]dec-8-yl)-cyclohexanone by introduction of the nitrile group with tosylmethyl isocyanide (TOSMIC), alkylation with LDA (diisopropylamine/butyl-lithium) and heptyl bromide, detachment of the keto-protective group, reduction of the ketone with $NaBH_4$ to the alcohol and separation of the isomers) are added to 19.8 g (0.1 mole) of trans-4-pentylcyclohexanecarboxylic acid in 75 ml of $CH_2Cl_2$, with stirring. A solution of 27.7 g (0.105 mole) of dicyclo-hexylcarbodiimide in 50 ml of methylene chloride is added dropwise at 0°, while controlling the temperature, and the mixture is then stirred at room temperature for a further hour. The urea precipitated is separated off and the methylene chloride phase is washed with dilute HCl and saturated $NaHCO_3$ solution and dried. The product is then purified by filtration over a short silica gel column and by crystallisation. 4-Cyano-4-heptyl-4'-(trans-4-pentylcyclohexylcarbonyloxy)-bicyclohexane is obtained.

The following compounds are prepared analogously:
4-cyano-4-heptyl-4'-(trans-4-ethylcyclohexylcarbonyloxy)bicyclohexane
4-cyano-4-heptyl-4'-(trans-4-propylcyclohexylcarbonyloxy)bicyclohexane
4-cyano-4-heptyl-4'-(trans-4-butylcyclohexylcarbonyloxy)bicyclohexane
4-cyano-4-heptyl-4'-(trans-4-heptylcyclohexylcarbonyloxy)bicyclohexane
4-cyano-4-pentyl-4'-(trans-4-ethylcyclohexylcarbonyloxy)bicyclohexane
4-cyano-4-pentyl-4'-(trans-4-propylcyclohexylcarbonyloxy)bicyclohexane
4-cyano-4-pentyl-4'-(trans-4-butylcyclohexylcarbonyloxy)bicyclohexane
4-cyano-4-pentyl-4'-(trans-4-pentylcyclohexylcarbonyloxy)bicyclohexane
4-cyano-4-pentyl-4'-(trans-4-heptylcyclohexylcarbonyloxy)bicyclohexane
4-cyano-4-propyl-4'-(trans-4-ethylcyclohexylcarbonyloxy)bicyclohexane
4-cyano-4-propyl-4'-(trans-4-propylcyclohexylcarbonyloxy)bicyclohexane
4-cyano-4-propyl-4'-(trans-4-butylcyclohexylcarbonyloxy)bicyclohexane
4-cyano-4-propyl-4'-(trans-4-pentylcyclohexylcarbonyloxy)bicyclohexane
4-cyano-4-propyl-4'-(trans-4-heptylcyclohexylcarbonyloxy)bicyclohexane
4-cyano-4-ethyl-4'-(trans-4-ethylcyclohexylcarbonyloxy)bicyclohexane
4-cyano-4-ethyl-4'-(trans-4-propylcyclohexylcarbonyloxy)bicyclohexane
4-cyano-4-ethyl-4'-(trans-4-butylcyclohexylcarbonyloxy)bicyclohexane
4-cyano-4-ethyl-4'-(trans-4-pentylcyclohexylcarbonyloxy)bicyclohexane
4-cyano-4-ethyl-4'-(trans-4-heptylcyclohexylcarbonyloxy)bicyclohexane

EXAMPLE 11

1 g of 4-dimethylaminopyridine and 22.3 g (0.1 mole) of 4-cyano-4-propylcyclohexanol (isomer mixture) [obtainable from 1,4-dioxaspiro[4,5]decan-8-one by introduction of the nitrile group with tosylmethyl isocyanide, alkylation with LDA and n-heptyl bromide, detachment of the keto-protective group and reduction of the ketone with $NaBH_4$] are added to 26.6 g (0.1 mole) of 4'-butylbicyclohexane-4-carboxylic acid in 75 ml of $CH_2Cl_2$, with stirring. A solution of 21.7 g (0.105 mole) of dicyclohexylcarbodiimide in 50 ml of $CH_2Cl_2$ is added dropwise, while controlling the temperature, and the mixture is then stirred at room temperature for a further hour. The urea precipitated is separated off and the methylene chloride phase is washed with dilute HCl and saturated NaHCO$_3$ solution and dried. After the solvent has been evaporated off, the residue is separated into its constituents by column chromatography (silica gel/petroleum ether (30–70):ether (5:1)). 4-(4-Cyano-4-heptylcyclohexyloxycarbonyl)-4'-butylbicyclohexane is obtained.

The following compounds are prepared analogously:
4-(4-cyano-4-n-heptylcyclohexyloxycarbonyl)-4'-ethylbicyclohexane
4-(4-cyano-4-n-heptylcyclohexyloxycarbonyl)-4'-propylbicyclohexane
4-(4-cyano-4-n-heptylcyclohexyloxycarbonyl)-4'-pentylbicyclohexane
4-(4-cyano-4-n-heptylcyclohexyloxycarbonyl)-4'-bicyclohexane
4-(4-cyano-4-n-pentylcyclohexyloxycarbonyl)-4'-ethylbicyclohexane
4-(4-cyano-4-n-pentylcyclohexyloxycarbonyl)-4'-propylbicyclohexane
4-(4-cyano-4-n-pentylcyclohexyloxycarbonyl)-4'-butylbicyclohexane
4-(4-cyano-4-n-pentylcyclohexyloxycarbonyl)-4'-pentylbicyclohexane
4-(4-cyano-4-n-pentylcyclohexyloxycarbonyl)-4'-heptylbicyclohexane
4-(4-cyano-4-n-butylcyclohexyloxycarbonyl)-4'-ethylbicyclohexane
4-(4-cyano-4-n-butylcyclohexyloxycarbonyl)-4'-propylbicyclohexane
4-(4-cyano-4-n-butylcyclohexyloxycarbonyl)-4'-butylbicyclohexane
4-(4-cyano-4-n-butylcyclohexyloxycarbonyl)-4'-pentylbicyclohexane
4-(4-cyano-4-n-butylcyclohexyloxycarbonyl)-4'-heptylbicyclohexane
4-(4-cyano-4-n-propylcyclohexyloxycarbonyl)-4'-ethylbicyclohexane
4-(4-cyano-4-n-propylcyclohexyloxycarbonyl)-4'-propylbicyclohexane
4-(4-cyano-4-n-propylcyclohexyloxycarbonyl)-4'-butylbicyclohexane
4-(4-(4-cyano-4-n-propylcyclohexyloxycarbonyl)-4'-pentylbicyclohexane
4-(4-cyano-4-n-propylcyclohexyloxycarbonyl)-4'-heptylbicyclohexane

EXAMPLE 12

27.2 g (0.1 mole) of p-(4-methyl-4-pentylcyclohexyl)-benzaldehyde (obtainable from 4-cyanocyclohexylbenzene by alkylation with LDA and heptyl bromide, stepwise conversion of the nitrile group into the methyl group by reduction with DIBAH and hydrazine in a Wolff-Kishner reaction and introduction of the formyl group by chloromethylation and a Sommelet reaction) are boiled with 16.0 g (0.1 mole) of 2-hexylpropane-1,3-diol and 0.1 g of p-toluenesulfonic acid in 150 ml of toluene, using a water separator, until no further water of reaction is formed. The cooled reaction mixture is washed twice with 5% NaHCO$_3$ solution (100 ml each time) and then with water and dried. After the solvent has been evaporated off, the residue is recrystallised from ethanol. p-(4-Methyl-4-pentylcyclohexyl)-(5-hexyl-1,3-dioxan-2-yl)-benzene is obtained.

The following compounds are prepared analogously:

p-(4-methyl-4-pentylcyclohexyl)-(5-ethyl-1,3-dioxan-2-yl)-benzene.
p-(4-methyl-4-pentylcyclohexyl)-(5-propyl-1,3-dioxan-2-yl)-benzene
p-(4-methyl-4-pentylcyclohexyl)-(5-butyl-1,3-dioxan-2-yl)-benzene
p-(4-methyl-4-pentylcyclohexyl)-(5-pentyl-1,3-dioxan-2-yl)-benzene
p-(4-methyl-4-pentylcyclohexyl)-(5-heptyl-1,3-dioxan-2-yl)-benzene
p-(4-methyl-4-propylcyclohexyl)-(5-ethyl-1,3-dioxan-2-yl)-benzene
p-(4-methyl-4-propylcyclohexyl)-(5-propyl-1,3-dioxan-2-yl)-benzene
p-(4-methyl-4-propylcyclohexyl)-(5-butyl-1,3-dioxan-2-yl)-benzene
p-(4-methyl-4-propylcyclohexyl)-(5-pentyl-1,3-dioxan-2-yl)-benzene
p-(4-methyl-4-propylcyclohexyl)-(5-heptyl-1,3-dioxan-2-yl)-benzene
p-(4-cyano-4-pentylcyclohexyl)-(5-ethyl-1,3-dioxan-2-yl)-benzene
p-(4-cyano-4-pentylcyclohexyl)-(5-propyl-1,3-dioxan-2-yl)-benzene
p-(4-cyano-4-pentylcyclohexyl)-(5-butyl-1,3-dioxan-2-yl)-benzene
p-(4-cyano-4-pentylcyclohexyl)-(5-pentyl-1,3-dioxan-2-yl)-benzene
p-(4-cyano-4-pentylcyclohexyl)-(5-heptyl-1,3-dioxan-2-yl)benzene
p-(4-cyano-4-butylcyclohexyl)-(5-ethyl-1,3-dioxan-2-yl)benzene
p-(4-cyano-4-butylcyclohexyl)-(5-propyl-1,3-dioxan-2-yl)benzene
p-(4-cyano-4-butylcyclohexyl)-(5-butyl-1,3-dioxan-2-yl)benzene
p-(4-cyano-4-butylcyclohexyl)-(5-pentyl-1,3-dioxan-2-yl)benzene
p-(4-cyano-4-butylcyclohexyl)-(5-heptyl-1,3-dioxan-2-yl)benzene
p-(4-cyano-4-propylcyclohexyl)-(5-ethyl-1,3-dioxan-2-yl)benzene
p-(4-cyano-4-propylcyclohexyl)-(5-propyl-1,3-dioxan-2-yl)-benzene
p-(4-cyano-4-propylcyclohexyl)-(5-butyl-1,3-dioxan-2-yl)benzene
p-(4-cyano-4-propylcyclohexyl)-(5-pentyl-1,3-dioxan-2-yl)-benzene
p-(4-cyano-4-propylcyclohexyl)-(5-heptyl-1,3-dioxan-2-yl)-benzene
4-(4-cyano-4-heptylcyclohexyl)-4'-(5-ethyl-1,3-dioxan-2-yl)-biphenyl
4-(4-cyano-4-heptylcyclohexyl)-4'-(5-propyl-1,3-dioxan-2-yl)-biphenyl
4-(4-cyano-4-heptylcyclohexyl)-4'-(5-butyl-1,3-dioxan-2-yl)-biphenyl
4-(4-cyano-4-heptylcyclohexyl)-4'-(5-pentyl-1,3-dioxan-2-yl)-biphenyl
4-(4-cyano-4-heptylcyclohexyl)-4'-(5-heptyl-1,3-dioxan-2-yl)-biphenyl
4-(4-cyano-4-pentylcyclohexyl)-4'-(5-ethyl-1,3-dioxan-2-yl)-biphenyl
4-(4-cyano-4-pentylcyclohexyl)-4'-(5-propyl-1,3-dioxan-2-yl)-biphenyl
4-(4-cyano-4-pentylcyclohexyl)-4'-(5-butyl-1,3-dioxan-2-yl)-biphenyl
4-(4-cyano-4-pentylcyclohexyl)-4'-(5-pentyl-1,3-dioxan-2-yl)-biphenyl 4-(4-cyano-4-pentylcyclohexyl)-4'-(5-heptyl-1,3-dioxan-2-yl)-biphenyl
4-(4-cyano-4-butylcyclohexyl)-4'-(5-ethyl-1,3-dioxan-2-yl)-biphenyl
4-(4-cyano-4-butylcyclohexyl)-4'-(5-propyl-1,3-dioxan-2-yl)-biphenyl
4-(4-cyano-4-butylcyclohexyl)-4'-(5-butyl-1,3-dioxan-2-yl)-biphenyl
4-(4-cyano-4-butylcyclohexyl)-4'-(5-pentyl-1,3-dioxan-2-yl)-biphenyl
4-(4-cyano-4-butylcyclohexyl)-4'-(5-heptyl-1,3-dioxan-2-yl)-biphenyl
4-(4-cyano-4-propylcyclohexyl)-4'-(5-ethyl-1,3-dioxan-2-yl)-biphenyl
4-(4-cyano-4-propylcyclohexyl)-4'-(5-propyl-1,3-dioxan-2-yl)-biphenyl
4-(4-cyano-4-propylcyclohexyl)-4'-(5-butyl-1,3-dioxan-2-yl)-biphenyl
4-(4-cyano-4-propylcyclohexyl)-4'-(5-pentyl-1,3-dioxan-2-yl)-biphenyl
4-(4-cyano-4-propylcyclohexyl)-4'-(5-heptyl-1,3-dioxan-2-yl)-biphenyl
4-(4-cyano-4-ethylcyclohexyl)-4'-(5-ethyl-1,3-dioxan-2-yl)-biphenyl
4-(4-cyano-4-ethylcyclohexyl)-4'-(5-propyl-1,3-dioxan-2-yl)-biphenyl
4-(4-cyano-4-ethylcyclohexyl)-4'-(5-butyl-1,3-dioxan-2-yl)-biphenyl
4-(4-cyano-4-ethylcyclohexyl)-4'-(5-pentyl-1,3-dioxan-2-yl)-biphenyl
4-(4-cyano-4-ethylcyclohexyl)-4'-(5-heptyl-1,3-dioxan-2-yl)-biphenyl
4-(4-methyl-4-pentylcyclohexyl)-4'-(5-ethyl-1,3-dioxan-2-yl)-2'-fluoro-biphenyl
4-(4-methyl-4-pentylcyclohexyl)-4'-(5-propyl-1,3-dioxan-2-yl)-2'-fluoro-biphenyl
4-(4-methyl-4-pentylcyclohexyl)-4'-(5-butyl-1,3-dioxan-2-yl)-2'-fluoro-biphenyl
4-(4-methyl-4-pentylcyclohexyl)-4'-(5-pentyl-1,3-dioxan-2-yl)-2'-fluoro-biphenyl
4-(4-methyl-4-pentylcyclohexyl)-4'-(5-heptyl-1,3-dioxan-2-yl)-2'-fluoro-biphenyl
4-(4-methyl-4-propylcyclohexyl)-4'-(5-ethyl-1,3-dioxan-2-yl)-2-fluoro-biphenyl
4-(4-methyl-4-propylcyclohexyl)-4'-(5-propyl-1,3-dioxan-2-yl)-2-fluoro-biphenyl
4-(4-methyl-4-propylcyclohexyl)-4'-(5-butyl-1,3-dioxan-2-yl)-2-fluoro-biphenyl
4-(4-methyl-4-propylcyclohexyl)-4'-(5-pentyl-1,3-dioxan-2-yl)-2-fluoro-biphenyl
4-(4-methyl-4-propylcyclohexyl)-4'-(5-heptyl-1,3-dioxan-2-yl)-2-fluoro-biphenyl

EXAMPLE 13

An isomer mixture of 1-hydroxy-1-[4'-(trans-4-pentylcyclohexyl)-biphenyl-4-yl]-4-n-propylcyclohexane [obtainable by reacting 4-n-propylcyclohexanone with 4'-(trans-4-pentylcyclohexyl)-biphenyl-4-yl-magnesium bromide and subsequent hydrolysis] is separated into the two stereoisomers by chromatography.

4.5 g of one of these alcohols are dissolved in 50 ml of methylene chloride and the solution is added dropwise to a solution of 1.7 ml of diethylamino-sulfur trifluoride (DAST) and 50 ml of methylene chloride at −60° in the course of 20 minutes. After 5 hours, the mixture is allowed to warm to room temperature and is stirred for 8 hours. After customary working up and recrystallisation from ethyl acetate, 2.2 g of r-1-fluoro-[4'-(trans-4-pentylcyclohexyl)-biphenyl-4-yl]-trans-4-propylcyclohexane of m.p. 267° are obtained.

0.3 g of r-1-fluoro-1-[4'-(trans-4-pentylcyclohexyl)-biphenyl-4-yl]-cis-4-propylcyclohexane of m.p. 176° and c.p. 309° is obtained in an analogous manner from 2.0 g of the other alcohol.

The following compounds are prepared analogously from the corresponding alcohols (in each case the two stereoisomers):

1-fluoro-1-ethyl-4-(trans-4-pentylcyclohexyl)-bi-phenyl-4-yl]-cyclohexane
1-fluoro-1-propyl-4-[4'-(trans-4-pentylcyclohexyl)-biphenyl-4-yl]-cyclohexane
1-fluoro-1-butyl-4-[4'-(trans-4-pentylcyclohexyl)-biphenyl-4-yl]-cyclohexane
1-fluoro-1-pentyl-4-[4'-(trans-4-pentylcyclohexyl)-biphenyl-4-yl]-cyclohexane
1-fluoro-1-heptyl-4-[4'-(trans-4-pentylcyclohexyl)-biphenyl-4-yl]-cyclohexane
1-fluoro-1-ethyl-4-[p-trans-4-pentylcyclohexyl)-phenyl]cyclohexane
1-fluoro-1-propyl-4-[p-trans-4-pentylcyclohexyl)-phenyl]cyclohexane
1-fluoro-1-butyl-4-[p-trans-4-pentylcyclohexyl)-phenyl]cyclohexane
1-fluoro-1-pentyl-4-[p-trans-4-pentylcyclohexyl)-phenyl]cyclohexane
1-fluoro-1-heptyl-4-[p-trans-4-pentylcyclohexyl)-phenyl]cyclohexane
1-fluoro-1-[p-(trans-4-pentylcyclohexyl)-phenyl]-4-ethylcyclohexane
1-fluoro-1-[p-(trans-4-pentylcyclohexyl)-phenyl]-4-propylcyclohexane
1-fluoro-1-[p-(trans-4-pentylcyclohexyl)-phenyl]-4-butylcyclohexane
1-fluoro-1-[p-(trans-4-pentylcyclohexyl)-phenyl]-4-pentylcyclohexane
1-fluoro-1-[p-(trans-4-pentylcyclohexyl)-phenyl]-4-heptylcyclohexane
1-fluoro-1-[4'-trans-4-pentylcyclohexyl)-biphenyl-4-yl]4-ethylcyclohexane
1-fluoro-1-[4'-trans-4-pentylcyclohexyl)-biphenyl-4-1]4-propylcyclohexane
1-fluoro-1-[4'-trans-4-pentylcyclohexyl)-biphenyl-4-yl]4-butylcyclohexane
1-fluoro-1-[4'-trans-4-pentylcyclohexyl)-biphenyl-4-yl]4-pentylcyclohexane
1-fluoro-1-[4'-trans-4-pentylcyclohexyl)-biphenyl-4-yl]4-heptylcyclohexane
1-fluoro-1-(4'-propylbiphenyl-4-yl)-4-ethylcyclohexane
1-fluoro-1-(4'-propylbiphenyl-4-yl)-4-propylcyclohexane
1-fluoro-1-(4'-propylbiphenyl-4-yl)-4-butylcyclohexane
1-fluoro-1-(4'-propylbiphenyl-4-yl)-4-pentylcyclohexane
1-fluoro-1-(4'-propylbiphenyl-4-yl)-4-heptylcyclohexane
1-fluoro-1-(4'-cyanobiphenyl-4-yl)-4-ethylcyclohexane
1-fluoro-1-(4'-cyanobiphenyl-4-yl)-4-propylcyclohexane
1-fluoro-1-(4'-cyanobiphenyl-4-yl)-4-butylcyclohexane
1-fluoro-1-(4'-cyanobiphenyl-4-yl)-4-pentylcyclohexane
1-fluoro-1-(4'-cyanobiphenyl-4-yl)-4-heptylcyclohexane
1-fluoro-1-(4'-butoxybiphenyl-4-yl)-4-ethylcyclohexane
1-fluoro-1-(4'-butoxybiphenyl-4-yl)-4-propylcyclohexane 1-fluoro-1-(4'-butoxybiphenyl-4-yl)-4-butylcyclohexane
1-fluoro-1-(4'-butoxybiphenyl-4-yl)-4-pentylcyclohexane
1-fluoro-1-(4'-butoxybiphenyl-4-yl)-4-heptylcyclohexane
1-fluoro-1-ethyl-4-(4'-pentylbiphenyl-4-yl)-cyclohexane
1-fluoro-1-propyl-4-(4'-pentylbiphenyl-4-yl)-cyclohexane
1-fluoro-1-butyl-4-(4'-pentylbiphenyl-4-yl)-cyclohexane
1-fluoro-1-pentyl-4-(4'-pentylbiphenyl-4-yl)-cyclohexane
1-fluoro-1-heptyl-4-(4'-pentylbiphenyl-4-yl)-cyclohexane
1-fluoro-1-ethyl-4-(4'-hexyloxybiphenyl-4-yl)-cyclohexane
1-fluoro-1-propyl-4-(4'-hexyloxybiphenyl-4-yl)-cyclohexane
1-fluoro-1-butyl-4-(4'-hexyloxybiphenyl-4-yl)-cyclohexane
1-fluoro-1-pentyl-4-(4'-hexyloxybiphenyl-4-yl)-cyclohexane
1-fluoro-1-heptyl-4-(4'-hexyloxybiphenyl-4-yl)-cyclohexane
1-fluoro-1-ethyl-4-(4'-propylbiphenyl-4-yl)-cyclohexane
1-fluoro-1-propyl-4-(4'-propylbiphenyl-4-yl)-cyclohexane
1-fluoro-1-butyl-4-(4'-propylbiphenyl-4-yl)-cyclohexane
1-fluoro-1-pentyl-4-(4'-propylbiphenyl-4-yl)-cyclohexane
1-fluoro-1-heptyl-4-(4'-propylbiphenyl-4-yl)-cyclohexane
1-fluoro-1-ethyl-4-(p-pentylphenyl)-cyclohexane
1-fluoro-1-propyl-4-(p-pentylphenyl)-cyclohexane
1-fluoro-1-butyl-4-(p-pentylphenyl)-cyclohexane
1-fluoro-1-pentyl-4-(p-pentylphenyl)-cyclohexane
1-fluoro-1-heptyl-4-(p-pentylphenyl)-cyclohexane
1-fluoro-1-ethyl-4-(p-propylphenyl)-cyclohexane
1-fluoro-1-propyl-4-(p-propylphenyl)-cyclohexane
1-fluoro-1-butyl-4-(p-propylphenyl)-cyclohexane
1-fluoro-1-pentyl-4-(p-propylphenyl)-cyclohexane
1-fluoro-1-heptyl-4-(p-propylphenyl)-cyclohexane
1-fluoro-1-(p-pentylphenyl)-4-ethylcyclohexane
1-fluoro-1-(p-pentylphenyl)-4-propylcyclohexane
1-fluoro-1-(p-pentylphenyl)-4-butylcyclohexane
1-fluoro-1-(p-pentylphenyl)-4-pentylcyclohexane
1-fluoro-1-(p-pentylphenyl)-4-heptylcyclohexane
1-fluoro-1-(p-propylphenyl)-4-ethylcyclohexane
1-fluoro-1-(p-propylphenyl)-4-propylcyclohexane
1-fluoro-1-(p-propylphenyl)-4-butylcyclohexane
1-fluoro-1-(p-propylphenyl)-4-pentylcyclohexane
1-fluoro-1-(p-propylphenyl)-4-heptylcyclohexane
1-fluoro-1-(trans-4-propylcyclohexyl)-4-ethylcyclohexane
1-fluoro-1-(trans-4-propylcyclohexyl)-4-propylcyclohexane
1-fluoro-1-(trans-4-propylcyclohexyl)-4-butylcyclohexane
1-fluoro-1-(trans-4-propylcyclohexyl)-4-pentylcyclohexane
1-fluoro-1-(trans-4-propylcyclohexyl)-4-heptylcyclohexane
1-fluoro-1-(trans-4-cyanocyclohexyl)-4-ethylcyclohexane
1-fluoro-1-(trans-4-cyanocyclohexyl)-4-propylcyclohexane
1-fluoro-1-(trans-4-cyanocyclohexyl)-4-butylcyclohexane
1-fluoro-1-(trans-4-cyanocyclohexyl)-4-pentylcyclohexane
1-fluoro-1-(trans-4-cyanocyclohexyl)-4-heptylcyclohexane
1-fluoro-1-ethyl-4-(trans-4-ethylcyclohexyl)-cyclohexane
1-fluoro-1-propyl-4-(trans-4-ethylcyclohexyl)-cyclohexane
1-fluoro-1-butyl-4-(trans-4-ethylcyclohexyl)-cyclohexane
1-fluoro-1-pentyl-4-(trans-4-ethylcyclohexyl)-cyclohexane
1-fluoro-1-heptyl-4-(trans-4-ethylcyclohexyl)-cyclohexane
1-fluoro-1-ethyl-4-(trans-4-propylcyclohexyl)-cyclohexane
1-fluoro-1-propyl-4-(trans-4-propylcyclohexyl)-cyclohexane
1-fluoro-1-butyl-4-(trans-4-propylcyclohexyl)-cyclohexane
1-fluoro-1-pentyl-4-(trans-4-propylcyclohexyl)-cyclohexane
1-fluoro-1-heptyl-4-(trans-4-propylcyclohexyl)-cyclohexane
1-fluoro-1-ethyl=4-(trans-4-pentylcyclohexyl)-cyclohexane
1-fluoro-1-propyl-4-(trans-4-pentylcyclohexyl)-cyclohexane
1-fluoro-1-butyl-4-(trans-4-pentylcyclohexyl)-cyclohexane
1-fluoro-1-pentyl-4-(trans-4-pentylcyclohexyl)-cyclohexane
1-fluoro-1-heptyl-4-(trans-4-pentylcyclohexyl)-cyclohexane
1-fluoro-1-ethyl-4-(trans-4-heptylcyclohexyl)-cyclohexane
1-fluoro-1-propyl-4-(trans-4-heptylcyclohexyl)-cyclohexane
1-fluoro-1-butyl-4-(trans-4-heptylcyclohexyl)-cyclohexane
1-fluoro-1-pentyl-4-(trans-4-heptylcyclohexyl)-cyclohexane
1-fluoro-1-heptyl-4-(trans-4-heptylcyclohexyl)-cyclohexane

EXAMPLE 14

125 ml (0.2 mole) of a 1.6N solution of butyllithium in hexane and 53 g (0.2 mole) of methyl 4-transpropylbicyclohexyl-4'-carboxylate in 40 ml of THF are added dropwise in succession to 20.3 g (0.2 mole) of diisopropylamine in 140 ml of THF at a temperature between $-10°$ and $-15°$, with exclusion of moisture and under a nitrogen atmosphere. The reaction mixture is then stirred for 20 minutes. 37.6 g (0.21 mole) of 1-bromoheptane are then added, likewise at $-10°$, and the mixture is subsequently stirred at room temperature for a further two hours. Customary working up gives methyl 4-propyl4'-heptyl-bicyclohexyl-4'-carboxylate of m.p. 49°.

The following compounds are prepared analogously:
methyl 4-butyl-4'-heptyl-bicyclohexyl-4'-carboxylate
methyl 4-pentyl-4'-heptyl-bicyclohexyl-4'-carboxylate
methyl 4-heptyl-4'-heptyl-bicyclohexyl-4'-carboxylate
methyl 4-ethyl-4'-pentyl-bicyclohexyl-4'-carboxylate
methyl 4-propyl-4'-pentyl-bicyclohexyl-4'-carboxylate
methyl 4-butyl-4'-pentyl-bicyclohexyl-4'-carboxylate methyl 4-pentyl-4'-pentyl-bicyclohexyl-4'-carboxylate
methyl 4-heptyl-4'-pentyl-bicyclohexyl-4'-carboxylate
methyl 4-propyl-4'-methyl-bicyclohexyl-4'-carboxylate
ethyl 4-propyl-4'-methyl-bicyclohexyl-4'-carboxylated
propyl 4-propyl-4'-methyl-bicyclohexyl-4'-carboxylate
butyl 4-propyl-4'-methyl-bicyclohexyl-4'-carboxylate
pentyl 4-propyl-4'-methyl-bicyclohexyl-4'-carboxylate
hexyl 4-propyl-4'-methyl-bicyclohexyl-4'-carboxylate
heptyl 4-propyl-4'-methyl-bicyclohexyl-4'-carboxylate
methyl 4-butyl-4'-methyl-bicyclohexyl-4'-carboxylate
ethyl 4-butyl-4'-methyl-bicyclohexyl-4'-carboxylate
propyl 4-butyl-4'-methyl-bicyclohexyl-4'-carboxylate
butyl 4-butyl-4'-methyl-bicyclohexyl-4'-carboxylate
pentyl 4-butyl-4'-methyl-bicyclohexyl-4'-carboxylate
hexyl 4-butyl-4'-methyl-bicyclohexyl-4'-carboxylate
heptyl 4-butyl-4'-methyl-bicyclohexyl-4'-carboxylate
methyl 4-pentyl-4'-methyl-bicyclohexyl-4'-carboxylate
ethyl 4-pentyl-4'-methyl-bicyclohexyl-4'-carboxylate
propyl 4-pentyl-4'-methyl-bicyclohexyl-4'-carboxylate
butyl 4-pentyl-4'-methyl-bicyclohexyl-4'-carboxylate
pentyl 4-pentyl-4'-methyl-bicyclohexyl-4'-carboxylate
hexyl 4-pentyl-4'-methyl-bicyclohexyl-4'-carboxylate
heptyl 4-pentyl-4'-methyl-bicyclohexyl-4'-carboxylate
methyl 4-[2-(trans-4-propylcyclohexyl)-ethyl]-4'-heptylbicyclohexyl-4-carboxylate
methyl 4-[2-(trans-4-butylcyclohexyl)-ethyl]-4'-heptylbicyclohexyl-4-carboxylate
methyl 4-[2-(trans-4-pentylcyclohexyl)-ethyl]-4'-heptylbicyclohexyl-4-carboxylate
methyl 4-[2-(trans-4-heptylcyclohexyl)-ethyl]-4'-heptylbicyclohexyl-4-carboxylate
methyl 4-[2-(trans-4-propylcyclohexyl)-ethyl]-4'-pentylbicyclohexyl-4-carboxylate
methyl 4-[2-(trans-4-butylcyclohexyl)-ethyl]-4'-pentylbicyclohexyl-4-carboxylate
methyl 4-[2-(trans-4-pentylcyclohexyl)-ethyl]-4'-pentylbicyclohexyl-4-carboxylate
methyl 4-[2-(trans-4-heptylcyclohexyl)-ethyl]-4'-pentylbicyclohexyl-4-carboxylate
methyl 4-[2-(trans-4-propylcyclohexyl)-ethyl]-4'-methylbicyclohexyl-4-carboxylate
ethyl 4-[2-(trans-4-propylcyclohexyl)-ethyl]-4'-methylbicyclohexyl-4-carboxylate
propyl 4-[2-(trans-4-propylcyclohexyl)-ethyl]-4'-methylbicyclohexyl-4-carboxylate
butyl 4-[2-(trans-4-propylcyclohexyl)-ethyl]-4'-methylbicyclohexyl-4-carboxylate
pentyl 4-[2-(trans-4-propylcyclohexyl)-ethyl]-4'-methylbicyclohexyl-4-carboxylate
heptyl 4-[2-(trans-4-propylcyclohexyl)-ethyl]-4'-methylbicyclohexyl-4-carboxylate
methyl 4-[2-(trans-4-pentylcyclohexyl)-ethyl]-4'-methylbicyclohexyl-4-carboxylate
ethyl 4-[2-(trans-4-pentylcyclohexyl)-ethyl]-4'-methylbicyclohexyl-4-carboxylate
propyl 4-[2-(trans-4-pentylcyclohexyl)-ethyl]-4'-methylbicyclohexyl-4-carboxylate
butyl 4-[2-(trans-4-pentylcyclohexyl)-ethyl]-4'-methylbicyclohexyl-4-carboxylate
pentyl 4-[2-(trans-4-pentylcyclohexyl)-ethyl]-4'-methylbicyclohexyl-4-carboxylate
heptyl 4-[2-(trans-4-pentylcyclohexyl)-ethyl]-4'-methylbicyclohexyl-4-carboxylate
methyl 4-(p-propylphenyl)-4'-pentyl-bicyclohexyl-4'-carboxylate
methyl 4-(p-butylphenyl)-4'-pentyl-bicyclohexyl-4'-carboxylate
methyl 4-(p-pentylphenyl)-4'-pentyl-bicyclohexyl-4'carboxylate
methyl 4-(p-heptylphenyl)-4'-pentyl-bicyclohexyl-4'carboxylate
methyl 4-(p-propylphenyl)-4'-heptyl-bicyclohexyl-4'carboxylate
methyl 4-(p-butylphenyl)-4'-heptyl-bicyclohexyl-4'carboxylate
methyl 4-(p-pentylphenyl)-4'-heptyl-bicyclohexyl-4'-carboxylate
methyl 4-(p-heptylphenyl)-4'-heptyl-bicyclohexyl-4'-carboxylate
methyl 4-(p-propylphenyl)-4'-methyl-bicyclohexyl-4'-carboxylate
methyl 4-(p-propylphenyl)-4'-methyl-bicyclohexyl-4'-carboxylate
propyl 4-(p-propylphenyl)-4'-methyl-bicyclohexyl-4'-carboxylate
butyl 4-(p-propylphenyl)-4'-methyl-bicyclohexyl-4'-carboxylate
hexyl 4-(p-propylphenyl)-4'-methyl-bicyclohexyl-4'-carboxylate
heptyl 4-(p-propylphenyl)-4'-methyl-bicyclohexyl-4'-carboxylate
methyl 4-(p-butylphenyl)-4'-methyl-bicyclohexyl-4'-carboxylate
ethyl 4-(p-butylphenyl)-4'-methyl-bicyclohexyl-4'-carboxylate
propyl 4-(p-butylphenyl)-4'-methyl-bicyclohexyl-4'-carboxylate
butyl 4-(p-butylphenyl)-4'-methyl-bicyclohexyl-4'-carboxylate
hexyl 4-(p-butylphenyl)-4'-methyl-bicyclohexyl-4'-carboxylate
heptyl 4-(p-butylphenyl)-4'-methyl-bicyclohexyl-4'-carboxylate
methyl 4-(p-pentylphenyl)-4'-methyl-bicyclohexyl-4'-carboxylate
ethyl 4-(p-pentylphenyl)-4'-methyl-bicyclohexyl-4'-carboxylate
propyl 4-(p-pentylphenyl)-4'-methyl-bicyclohexyl-4'-carboxylate
butyl 4-(p-pentylphenyl)-4'-methyl-bicyclohexyl-4'-carboxylate
hexyl 4-(p-pentylphenyl)-4'-methyl-bicyclohexyl-4'-carboxylate
heptyl 4-(p-pentylphenyl)-4'-methyl-bicyclohexyl-4'-carboxylate
methyl 4-(p-butoxyphenyl)-4'-methyl-bicyclohexyl-4'-carboxylate
ethyl 4-(p-butoxyphenyl)-4'-methyl-bicyclohexyl-4'-carboxylate
propyl 4-(p-butoxyphenyl)-4'-methyl-bicyclohexyl-4'-carboxylate
butyl 4-(p-butoxyphenyl)-4'-methyl-bicyclohexyl-4'-carboxylate
hexyl 4-(p-butoxyphenyl)-4'-methyl-bicyclohexyl-4'-carboxylate
heptyl 4-(p-butoxyphenyl)-4'-methyl-bicyclohexyl-4'-carboxylate
methyl 4-[4'-(trans-4-propylcyclohexyl)-biphenyl-4-yl]1-heptyl-cyclohexane-1-carboxylate
methyl 4-[4'-(trans-4-butylcyclohexyl)-biphenyl-4-yl]-1-heptyl-cyclohexane-1-carboxylate
methyl 4-[4'-(trans-4-pentylcyclohexyl)-biphenyl-4-yl]-1-heptyl-cyclohexane-1-carboxylate
methyl 4-[4'-(trans-4-heptylcyclohexyl)-biphenyl-4-yl]-1-heptyl-cyclohexane-1-carboxylate methyl 4-[4'-(trans-4-propylcyclohexyl)-biphenyl-4-yl]-1-pentyl-cyclohexane-1-carboxylate
1 methyl 4-[4'-(trans-4-butylcyclohexyl)-biphenyl-4-yl]-1-pentyl-cyclohexane-1-carboxylate
methyl 4-[4'-(trans-4-pentylcyclohexyl)-biphenyl-4-yl]1-pentyl-cyclohexane-1-carboxylate
methyl 4-[4'-(trans-4-heptylcyclohexyl)-biphenyl-4-yl]1-pentyl-cyclohexane-1-carboxylate
methyl 4-[4'-(trans-4-propylcyclohexyl)-biphenyl-4-yl]1-methyl-cyclohexane-1-carboxylate
ethyl 4-[4'-(trans-4-propylcyclohexyl)-biphenyl-4-yl]-1-methyl-cyclohexane-1-carboxylate
propyl 4-[4'-(trans-4-propylcyclohexyl)-biphenyl-4-yl]1-methyl-cyclohexane-1-carboxylate
butyl 4-[4'-(trans-4-propylcyclohexyl)-biphenyl-4-yl]-1-methyl-cyclohexane-1-carboxylate
pentyl 4-[4'-(trans-4-propylcyclohexyl)-biphenyl-4-yl]1-methyl-cyclohexane-1-carboxylate
methyl 4-[4'-(trans-4-pentylcyclohexyl)-biphenyl-4-yl]1-methyl-cyclohexane-1-carboxylate
ethyl 4-[4'-(trans-4-pentylcyclohexyl)-biphenyl-4-yl]-11methyl-cyclohexane-1-carboxylate
propyl 4-[4'-(trans-4-pentylcyclohexyl)-biphenyl-4-yl]-methyl-cyclohexane-1-carboxylate
butyl 4-[4'-(trans-4-pentylcyclohexyl)-biphenyl-4-yl]1-methyl-cyclohexane-1-carboxylate
pentyl 4-[4'-(trans-4-pentylcyclohexyl)-biphenyl-4-yl]1-methyl-cyclohexane-1-carboxylate

EXAMPLE 15

7.2 g of ethanethiol and 35 g of 4-pentyl-4'heptyl-4'-hydroxybicyclohexane in 70 ml of glacial acetic acid are added dropwise to a mixture of 30 ml of glacial acetic acid, 11.1 g of acetic anhydride and 7 g of 72% aqueous perchloric acid solution at −20°. The mixture is stirred at room temperature for 24 hours, poured into 250 ml of saturated sodium chloride solution, extracted with petroleum ether and worked up in the customary manner. 4-Pentyl-4'-heptyl-4'-ethylthiobicyclohexane is obtained.

The following compounds are prepared analogously:
4-pentyl-4'-propyl-4'-ethylthiobicyclohexane
4-pentyl-4'-butyl-4'-ethylthiobicyclohexane
4-pentyl-4'-pentyl-4'-ethylthiobicyclohexane
4-pentyl-4'-hexyl-4'-ethylthiobicyclohexane
4-pentyl-4'-octyl-4'-ethylthiobicyclohexane
4-propyl-4'-propyl-4'-methylthiobicyclohexane
4-propyl-4'-butyl-4'-methylthiobicyclohexane
4-propyl-4'-pentyl-4'-methylthiobicyclohexane
4-propyl-4'-hexyl-4'-methylthiobicyclohexane
4-propyl-4'-heptyl-4'-methylthiobicyclohexane
4-butyl-4'-propyl-4'-methylthiobicyclohexane
4-butyl-4'-butyl-4'-methylthiobicyclohexane
4-butyl-4'-pentyl-4'-methylthiobicyclohexane
4-butyl-4'-hexyl-4'-methylthiobicyclohexane
4-butyl-4'-heptyl-4'-methylthiobicyclohexane
4-pentyl-4'-propyl-4'-methylthiobicyclohexane
4-pentyl-4'-butyl-4'-methylthiobicyclohexane
4-pentyl-4'-pentyl-4'-methylthiobicyclohexane
4-pentyl-4'-hexyl-4'-methylthiobicyclohexane
4-pentyl-4'-heptyl-4'-methylthiobicyclohexane
4-heptyl-4'-propyl-4'-methylthiobicyclohexane
4-heptyl-4'-butyl-4'-methylthiobicyclohexane
4-heptyl-4'-pentyl-4'-methylthiobicyclohexane
4-heptyl-4'-hexyl-4'-methylthiobicyclohexane
4-heptyl-4'-heptyl-4'-methylthiobicyclohexane
4-pentyl-4'-methyl-4'-ethylthiobicyclohexane
4-pentyl-4'-methyl-4'-propylthiobicyclohexane
4-pentyl-4'-methyl-4'-butylthiobicyclohexane
4-pentyl-4'-methyl-4'-pentylthiobicyclohexane
4-pentyl-4'-methyl-4'-hexylthiobicyclohexane
4-propyl-4'-methyl-4'-ethylthiobicyclohexane
4-propyl-4'-methyl-4'-propylthiobicyclohexane
4-propyl-4'-methyl-4'-butylthiobicyclohexane
4-propyl-4'-methyl-4"-pentylthiobicyclohexane
4-propyl-4'-methyl-4'-hexylthiobicyclohexane

EXAMPLE 16

3.3 g of 4-pentyl-4'-heptyl-4'-ethylthiobicyclohexane are dissolved in 20 ml of chloroform. A solution of 5.3 g of 70% m-chloroperbenzoic acid in 100 ml of chloroform is added dropwise at 5°–10°. After the mixture has been left to stand for 15 hours and after customary working up, 4-pentyl-4'-heptyl-4'-ethylsulfonylbicyclohexane is obtained.

The following compounds are prepared analogously:
4-pentyl-4'-propyl-4'-ethylsulfonylbicyclohexane
4-pentyl-4'-butyl-4'-ethylsulfonylbicyclohexane
4-pentyl-4'-pentyl-4'-ethylsulfonylbicyclohexane
4-pentyl-4'-hexyl-4'-ethylsulfonylbicyclohexane
4-pentyl-4'-octyl-4'-ethylsulfonylbicyclohexane
4-propyl-4'-propyl-4'-methylsulfonylbicyclohexane
4-propyl-4'-butyl-4'-methylsulfonylbicyclohexane
4-propyl-4,-pentyl-4'-methylsulfonylbicyclohexane
4-propyl-4'-hexyl-4'-methylsulfonylbicyclohexane
4-propyl-4'-heptyl-4'-methylsulfonylbicyclohexane
4-butyl-4'-propyl--4'-methylsulfonylbicyclohexane
4-butyl-4'-butyl-4'-methylsulfonylbicyclohexane
4-butyl-4'-pentyl-4'-methylsulfonylbicyclohexane
4-butyl-4'-hexyl-4'-methylsulfonylbicyclohexane
4-butyl-4'-heptyl-4'-methylsulfonylbicyclohexane
4-pentyl-4'-propyl-4'-methylsulfonylbicyclohexane
4-pentyl-4'-butyl-4'-methylsulfonylbicyclohexane
4-pentyl-4'-pentyl-4'-methylsulfonylbicyclohexane
4-pentyl-4'-hexyl-4'-methylsulfonylbicyclohexane
4-pentyl-4'-heptyl-4'-methylsulfonylbicyclohexane
4-heptyl-4'-propyl-4'-methylsulfonylbicyclohexane
4-heptyl-4'-butyl-4'-methylsulfonylbicyclohexane
4-heptyl-4'-pentyl-4'-methylsulfonylbicyclohexane
4-heptyl-4'-hexyl-4'-methylsulfonylbicyclohexane
4-heptyl-4'-heptyl-4'-methylsulfonylbicyclohexane
4-pentyl-4'-methyl-4'-ethylsulfonylbicyclohexane
4-pentyl-4'-methyl-4'-propylsulfonylbicyclohexane
4-pentyl-4'-methyl-4'-butylsulfonylbicyclohexane
-pentyl-4'-methyl-4'-pentylsulfonylbicyclohexane
-pentyl-4'-methyl-4'-hexylsulfonylbicyclohexane
-propyl-4'-methyl-4'-ethylsulfonylbicyclohexane
-propyl-4'-methyl-4'-propylsulfonylbicyclohexane
-propyl-4'-methyl-4'-butylsulfonylbicyclohexane
-propyl-4'-methyl-4'-pentylsulfonylbicyclohexane
-propyl-4'-methyl-4'-hexylsulfonylbicyclohexane

EXAMPLE 17

1 ml of 30% $H_2O_2$ is added to 3.8 g of 4-pentyl-4'-heptyl-4'-ethylthiobicyclohexane in 25 ml of glacial acetic acid and the mixture is stirred at room temperature for 3 hours. After customary working up, 4-pentyl-4'-heptyl-4'-ethylsulfinylbicyclohexane is obtained.

The following compounds are prepared analogously:
4-pentyl-4'-propyl-4'-ethylsulfinylbicyclohexane
4-pentyl-4'-butyl-4'-ethylsulfinylbicyclohexane
4-pentyl-4'-pentyl-4'-ethylsulfinylbicyclohexane
4-pentyl-4'-hexyl-4'-ethylsulfinylbicyclohexane
4-pentyl-4'-octyl-4'-ethylsulfinylbicyclohexane
4-propyl-4'-propyl-4'-methylsulfinylbicyclohexane
4-propyl-4'-butyl-4'-methylsulfinylbicyclohexane 4-propyl-4'-pentyl-4'-methylsulfinylbicyclohexane
4-propyl-4'-hexyl-4'-methylsulfinylbicyclohexane
4-propyl-4'-heptyl-4'-methylsulfinylbicyclohexane
4-butyl-4'-propyl-4'-methylsulfinylbicyclohexane
4-butyl-4'-butyl-4'-methylsulfinylbicyclohexane
4-butyl-4'-pentyl-4'-methylsulfinylbicyclohexane
4-butyl-4'-hexyl-4'-methylsulfinylbicyclohexane
4-butyl-4'-heptyl-4'-methylsulfinylbicyclohexane
4-pentyl-4'-propyl-4'-methylsulfinylbicyclohexane
4-pentyl-4'-butyl-4'-methylsulfinylbicyclohexane
4-pentyl-4'-pentyl-4'-methylsulfinylbicyclohexane
4-pentyl-4'-hexyl-4'-methylsulfinylbicyclohexane
4-pentyl-4'-heptyl-4'-methylsulfinylbicyclohexane
4-heptyl-4'-propyl-4'-methylsulfinylbicyclohexane
4-heptyl-4'-butyl-4'-methylsulfinylbicyclohexane
4-heptyl-4'-pentyl-4'-methylsulfinylbicyclohexane
4-heptyl-4'-hexyl-4'-methylsulfinylbicyclohexane
4-heptyl-4'-heptyl-4'-methylsulfinylbicyclohexane
4-pentyl-4'-methyl-4'-ethylsulfinylbicyclohexane
4-pentyl-4'-methyl-4'-propylsulfinylbicyclohexane
4-pentyl-4'-methyl-4'-butylsulfinylbicyclohexane
4-pentyl-4'-methyl-4'-pentylsulfinylbicyclohexane
4-pentyl-4'-methyl-4'-hexylsulfinylbicyclohexane
4-propyl-4'-methyl-4'-ethylsulfinylbicyclohexane
4-propyl-4'-methyl-4'-propylsulfinylbicyclohexane
4-propyl-4'-methyl-4'-butylsulfinylbicyclohexane
4-propyl-4'-methyl-4'-pentylsulfinylbicyclohexane
4-propyl-4'-methyl-4'-hexylsulfinylbicyclohexane

EXAMPLE 18

16.4 g of 2-butylpropane-1,3-dithiol, 20.7 g of 4-cyano-4-pentylcyclohexanecarbaldehyde [obtainable by a Wittig reaction from 4-cyano-4-pentylcyclohexanone with triphenylphosphine-toluyloxymethylene and subsequent hydrolysis], 200 ml of methylene chloride and 150 mg of $AlCl_3$ are stirred for 15 hours. Customary working up gives 2-(4-cyano-4-pentylcyclohexyl)-5-butyl-1,3-dithiane.

The following compounds are prepared analogously:
2-(4-cyano-4-pentylcyclohexyl)-5-ethyl-1,3-dithiane
2-(4-cyano-4-pentylcyclohexyl)-5-propyl-1,3-dithiane
2-(4-cyano-4-pentylcyclohexyl)-5-pentyl-1,3-dithiane
2-(4-cyano-4-pentylcyclohexyl)-5-heptyl-1,3-dithiane
2-(4-cyano-4-heptylcyclohexyl)-5-ethyl-1,3-dithiane
2-(4-cyano-4-heptylcyclohexyl)-5-propyl-1,3-dithiane
2-(4-cyano-4-heptylcyclohexyl)-5-butyl-1,3-dithiane
2-(4-cyano-4-heptylcyclohexyl)-5-pentyl-1,3-dithianze
2-(4-cyano-4-heptylcyclohexyl)-5-heptyl-1,3-dithiane
2-(4-cyano-4-propylcyclohexyl)-5-ethyl-1,3-dithiane
2-(4-cyano-4-propylcyclohexyl)-5-propyl-1,3-dithiane
2-(4-cyano-4-propylcyclohexyl)-5-butyl-1,3-dithiane
2-(4-cyano-4-propylcyclohexyl)-5-pentyl-1,3-dithiane
2-(4-cyano-4-propylcyclohexyl)-5-heptyl-1,3-dithiane
2-[p-(4-cyano-4-propylcyclohexyl)-phenyl]-5-ethyl-1,3-dithiane
2-[p-(4-cyano-4-propylcyclohexyl)-phenyl]-5-propyl-1,3-dithiane
2-[p-(4-cyano-4-propylcyclohexyl)-phenyl]-5-butyl-1,3-dithiane
2-[p-(4-cyano-4-propylcyclohexyl)-phenyl]-5-pentyl-1,3-dithiane
2-[p-(4-cyano-4-propylcyclohexyl)-phenyl]-5-heptyl-1,3-dithiane
2-[p-(4-cyano-4-butylcyclohexyl)-phenyl]-5-ethyl-1,3-dithiane
2-[p-(4--cyano-4-butylcyclohexyl)-phenyl]-5-propyl-1,3-dithiane
2-[p-(4-cyano-4-butylcyclohexyl)-phenyl]-5-butyl-1,3-dithiane
2-[p-(4-cyano-4-butylcyclohexyl)-phenyl]-5-pentyl-3-dithiane
2-[p-(4-cyano-4-butylcyclohexyl)-phenyl]-5-heptyl-1,3-dithiane
2-[p-(4-cyano-4-pentylcyclohexyl)-phenyl]-5-ethyl-1,3-dithiane
2-[p-(4-cyano-4-pentylcyclohexyl)-phenyl]-5-propyl-1,3-dithiane
2-[p-(4-cyano-4-pentylcyclohexyl)-phenyl]-5-butyl-1,3-dithiane
2-[p-(4-cyano-4-pentylcyclohexyl)-phenyl]-5-pentyl-1,3-dithiane
2-[p-(4-cyano-4-pentylcyclohexyl)-phenyl]-5-heptyl-1,3-dithiane
2-[4-(4-cyano-4-propylcyclohexyl)-biphenyl-4'-yl]-5-ethyl-1,3-dithiane
2-[4-(4-cyano-4-propylcyclohexyl)-biphenyl-4'-yl]-5-propyl-1,3-dithiane
2-[4-(4-cyano-4-propylcyclohexyl)-biphenyl-4'-yl]-5-butyl-1,3-dithiane
2-[4-(4-cyano-4-propylcyclohexyl)-biphenyl-4'-yl]-5-pentyl-1,3-dithiane
2-[4-(4-cyano-4-propylcyclohexyl)-biphenyl-4'-yl]-5-heptyl-1,3-dithiane
2-[4-(4-cyano-4-butylcyclohexyl)-biphenyl-4'-yl]-5-ethyl-1,3-dithiane
2-[4-(4-cyano-4-butylcyclohexyl)-biphenyl-4'-yl]-5-propyl-1,3-dithiane
2-[4-(4-cyano-4-butylcyclohexyl)-biphenyl-4'-yl]-5-butyl-1,3-dithiane
2-[4-(4-cyano-4-butylcyclohexyl)-biphenyl-4'-yl]-5-pentyl-1,3-dithiane
2-[4-(4-cyano-4-butylcyclohexyl)-biphenyl-4'-yl]-5-heptyl-1,3-dithiane
2-[4-(4-cyano-4-pentylcyclohexyl)-biphenyl-4'-yl]-5-ethyl-1,3-dithiane
2-[4-(4-cyano-4-pentylcyclohexyl)-biphenyl-4'-yl]-5-propyl-1,3-dithiane
2-[4-(4-cyano-4-pentylcyclohexyl)-biphenyl-4'-yl]-5-butyl-1,3-dithiane
2-[4-(4-cyano-4-pentylcyclohexyl)-biphenyl-4'-yl]-5-pentyl-1,3-dithiane
2-[4-(4-cyano-4-pentylcyclohexyl)-biphenyl-4'-yl]-5-heptyl-1,3-dithiane
2-[4-(4-cyano-4-heptylcyclohexyl)-biphenyl-4'-yl]-5-ethyl1,3-dithiane
2-[4-(4-cyano-4-heptylcyclohexyl)-biphenyl-4'-yl]-5-propyl-1,3-dithiane
2-[4-(4-cyano-4-heptylcyclohexyl)-biphenyl-4'-yl]-5-butyl-1,3-dithiane
2-[4-(4-cyano-4-heptylcyclohexyl)-biphenyl-4'-yl]-5-pentyl-1,3-dithiane
2-[4-(-4-cyano-4-heptylcyclohexyl)-biphenyl-4'-yl]-5-heptyl-1,3-dithiane

EXAMPLE 19

62.5 ml of a 1.6 molar solution of n-butyllithium in hexane and 28.7 g of (4aαH,8aαH)-decahydro-6β-propyl-2α-(4-cyanocyclohexyl)-naphthalene [obtainable by a process analogous to those described in German Offenlegungsschrift 3,150,312] in 40 ml of THF are added dropwise in succession to 10.1 g of diisopropylamine in 70 ml of tetrahydrofuran at −10°, under a nitrogen atmosphere. The reaction mixture is stirred for 20 minutes. 16.6 g of 1-bromopentane are then added at −10° and the mixture is stirred at room temperature for 20 minutes and worked up in the customary manner to give (4aαH,8aβH)-decahydro-6β-propyl-2α-(4-cyano-4-pentyl)-naphthalene.

The following compounds are prepared analogously:
(4aαH,8aαH)-decahydro-6β-propyl-2α-(4-cyano-4-ethyl)naphthalene
(4aαH,8aαH)-decahydro-6β-propyl-2α-(4-cyano-4-propyl)naphthalene
(4aαH,8aαH)-decahydro-6β-propyl-2α-(4-cyano-4-butyl)naphthalene
(4aαH,8aαH)-decahydro-6β-propyl-2α-(4-cyano-4-hexyl)naphthalene
(4aαH,8aαH)-decahydro-6β-propyl-2α-(4-cyano-4-heptyl)naphthalene
(4aαH,8aαH)-decahydro-6β-propyl-2α-(4-cyano-4-nonyl)naphthalene
(4aαH,8aαH)-decahydro-6β-butyl-2α-(4-cyano-4-ethyl)naphthalene
(4aαH,8aαH)-decahydro-6β-butyl-2α-(4-cyano-4-propyl)naphthalene
(4aαH,8aαH)-decahydro-6β-butyl-2α-(4-cyano-4-butyl)naphthalene
(4aαH,8aαH)-decahydro-6β-butyl-2α-(4-cyano-4-hexyl)naphthalene
(4aαH,8aαH)-decahydro-6β-butyl-2α-(4-cyano-4-heptyl)naphthalene
(4aαH,8aαH)-decahydro-6β-butyl-2α-(4-cyano-4-nonyl)naphthalene
(4aαH,8aαH)-decahydro-6β-pentyl-2α-(4-cyano-4-ethyl)naphthalene
(4aαH,8aαH)-decahydro-6β-pentyl-2α-(4-cyano-4-propyl)naphthalene
(4aαH,8aαH)-decahydro-6β-pentyl-2α-(4-cyano-4-butyl)naphthalene
(4aαH,8aαH)-decahydro-6β-pentyl-2α-(4-cyano-4-hexyl)naphthalene
(4aαH,8aαH)-decahydro-6β-pentyl-2α-(4-cyano-4-heptyl)naphthalene
(4aαH,8aαH)-decahydro-6β-pentyl-2α-(4-cyano-4-nonyl)naphthalene
(4aαH,8aαH)-decahydro-6β-heptyl-2α-(4-cyano-4-ethyl)naphthalene
(4aαH,8aαH)-decahydro-6β-heptyl-2α-(4-cyano-4-propyl)naphthalene
(4aαH,8aαH)-decahydro-6β-heptyl-2α-(4-cyano-4-butyl)naphthalene
(4aαH,8aαH)-decahydro-6β-heptyl-2α-(4-cyano-4-hexyl)naphthalene
(4aαH,8aαH)-decahydro-6β-heptyl-2α-(4-cyano-4-heptyl)naphthalene
(4aαH,8aαH)-decahydro-6β-heptyl-2α-(4-cyano-4-nonyl)naphthalene
(4aαH,8aαH)-decahydro-6β-butoxy-2α-(4-cyano-4-ethyl)naphthalene
(4aαH,8aαH)-decahydro-6β-butoxy-2α-(4-cyano-4-propyl)naphthalene
(4aαH,8aαH)-decahydro-6β-butoxy-2α-(4-cyano-4-butyl)naphthalene
(4aαH,8aαH)-decahydro-6β-butoxy-2α-(4-cyano-4-hexyl)naphthalene
(4aαH,8aαH)-decahydro-6β-butoxy-2α-(4-cyano-4-heptyl)naphthalene
(4aαH,8aαH)-decahydro-6β-butoxy-2α-(4-cyano-4-nonyl)naphthalene

EXAMPLE 20

4.3 g of NaNH$_2$ (50% in toluene) are added to a solution of 31.5 g of trans,trans,trans-4-cyano-4'''-propylter-cyclohexyl and 41 g of butylbromide in 70 ml of toluene. The reaction mixture is then boiled for 5 hours. After customary working up, r-1-cyano-1-butyl-cis-4-[trans-4-(trans-4-propylcyclohexyl)-cyclohexyl]-cyclohexane is obtained.

The following compounds are prepared analogously by alkylation of corresponding nitriles:
r-1-cyano-1-ethyl-cis-4-[trans-4-(trans-4-propylcyclohexyl)cyclohexyl]-cyclohexane
r-1-cyano-1-propyl-cis-4-[trans-4-(trans-4-propylcyclohexyl)cyclohexyl]-cyclohexane
r-1-cyano-1-pentyl-cis-4-[trans-4-(trans-4-propylcyclohexyl)cyclohexyl]-cyclohexane
r-1-cyano-1-hexyl-cis-4-[trans-4-(trans-4-propylcyclohexyl)cyclohexyl]-cyclohexane
r-1-cyano-1-heptyl-cis-4-[trans-4-(trans-4-propylcyclohexyl)cyclohexyl]-cyclohexane
r-1-cyano-1-octyl-cis-4-[trans-4-(trans-4-propylcyclohexyl)cyclohexyl]-cyclohexane
r-1-cyano-1-nonyl-cis-4-[trans-4-(trans-4-propylcyclohexyl)cyclohexyl]-cyclohexane
r-1-cyano-1-ethyl-cis-4-[trans-4-(trans-4-ethylcyclohexyl)cyclohexyl]-cyclohexane
r-1-cyano-1-propyl-cis-4-[trans-4-(trans-4-ethylcyclohexyl)cyclohexyl]-cyclohexane
r-1-cyano-1-butyl-cis-4-[trans-4-(trans-4-ethylcyclohexyl)cyclohexyl]-cyclohexane
r-1-cyano-1-pentyl-cis-4-[trans-4-(trans-4-ethylcyclohexyl)cyclohexyl]-cyclohexane
r-1-cyano-1-heptyl-cis-4-[trans-4-(trans-4-ethylcyclohexyl)cyclohexyl]-cyclohexane
r-1-cyano-1-ethyl-cis-4-[trans-4-(trans-4-butylcyclohexyl)cyclohexyl]-cyclohexane
r-1-cyano-1-propyl-cis-4-[trans-4-(trans-4-butylcyclohexyl)cyclohexyl]-cyclohexane
r-1-cyano-1-butyl-cis-4-[trans-4-(trans-4-butylcyclohexyl)cyclohexyl]-cyclohexane
r-1-cyano-1-pentyl-cis-4-[trans-4-(trans-4-butylcyclohexyl)cyclohexyl]-cyclohexane
r-1-cyano-1-heptyl-cis-4-[trans-4-(trans-4-butylcyclohexyl)cyclohexyl]-cyclohexane
r-1-cyano-1-ethyl-cis-4-[trans-4-(trans-4-pentylcyclohexyl)cyclohexyl]-cyclohexane
r-1-cyano-1-propyl-cis-4-[trans-4-(trans-4-pentylcyclohexyl)cyclohexyl]-cyclohexane
r-1-cyano-1-butyl-cis-4-[trans-4-(trans-4-pentylcyclohexyl)cyclohexyl]-cyclohexane
r-1-cyano-1-pentyl-cis-4-[trans-4-(trans-4-pentylcyclohexyl)cyclohexyl]-cyclohexane
r-1-cyano-1-heptyl-cis-4-[trans-4-(trans-4-pentylcyclohexyl)cyclohexyl]-cyclohexane
r-1-cyano-1-ethyl-cis-4-[trans-4-(trans-4-heptylcyclohexyl)cyclohexyl]-cyclohexane
r-1-cyano-1-propyl-cis-4-[trans-4-(trans-4-heptylcyclohexyl)cyclohexyl]-cyclohexane
r-1-cyano-1-butyl-cis-4-[trans-4-(trans-4-heptylcyclohexyl)cyclohexyl]-cyclohexane
r-1-cyano-1-pentyl-cis-4-[trans-4-(trans-4-heptylcyclohexyl)cyclohexyl]-cyclohexane
r-1-cyano-1-heptyl-cis-4-[trans-4-(trans-4-heptylcyclohexyl)cyclohexyl]-cyclohexane
r-1-cyano-1-[trans-4-(trans-4-ethylcyclohexyl)cyclohexyl]-cis-4-ethylcyclohexane
r-1-cyano-1-[trans-4-(trans-4-ethylcyclohexyl)cyclohexyl]-cis-4-propylcyclohexane
r-1-cyano-1-[trans-4-(trans-4-ethylcyclohexyl)cyclohexyl]-cis-4-butylcyclohexane r-1-cyano-1-[trans-4-(trans-4-ethylcyclohexyl)-cyclohexyl]-cis-4-pentylcyclohexane
r-1-cyano-1-[trans-4-(trans-4-ethylcyclohexyl)-cyclohexyl]-cis-4-heptylcyclohexane
r-1-cyano-1-[trans-4-(trans-4-propylcyclohexyl)-cyclohexyl]-cis-4-ethylcyclohexane
r-1-cyano-1-[trans-4-(trans-4-propylcyclohexyl)-cyclohexyl]-cis-4-propylcyclohexane
r-1-cyano-1-[trans-4-(trans-4-propylcyclohexyl)-cyclohexyl]-cis-4-butylcyclohexane
r-1-cyano-1-[trans-4-(trans-4-propylcyclohexyl)-cyclohexyl]-cis-4-pentylcyclohexane
r-1-cyano-1-[trans-4-(trans-4-propylcyclohexyl)-cyclohexyl]-cis-4-heptylcyclohexane
r-1-cyano-1-[trans-4-(trans-4-butylcyclohexyl)-cyclohexyl]-cis-4-ethylcyclohexane
r-1-cyano-1-[trans-4-(trans-4-butylcyclohexyl)-cyclohexyl]-cis-4-propylcyclohexane
r-1-cyano-1-[trans-4-(trans-4-butylcyclohexyl)-cyclohexyl]-cis-4-butylcyclohexane
r-1-cyano-1-[trans-4-(trans-4-butylcyclohexyl)-cyclohexyl]-cis-4-pentylcyclohexane
r-1-cyano-1-[trans-4-(trans-4-butylcyclohexyl)-cyclohexyl]-cis-4-heptylcyclohexane
r-1-cyano-1-trans-4-(trans-4-pentylcyclohexyl)-cyclohexyl]-cis-4-ethylcyclohexane
r-1-cyano-1-[trans-4-(trans-4-pentylcyclohexyl)-cyclohexyl]-cis-4-propylcyclohexane
r-1-cyano-1-[trans-4-(trans-4-pentylcyclohexyl)-cyclohexyl]-cis-4-butylcyclohexane
r-1-cyano-1-[trans-4-(trans-4-pentylcyclohexyl)-cyclohexyl]-cis-4-pentylcyclohexane
r-1-cyano-1-[trans-4-(trans-4-pentylcyclohexyl)-cyclohexyl]-cis-4-heptylcyclohexane
r-1-cyano-1-[trans-4-(trans-4-heptylcyclohexyl)-cyclohexyl]-cis-4-ethylcyclohexane
r-1-cyano-1-[trans-4-(trans-4-heptylcyclohexyl)-cyclohexyl]-cis-4-propylcyclohexane
r-1-cyano-1-[trans-4-(trans-4-heptylcyclohexyl)-cyclohexyl]-cis-4-butylcyclohexane
r-1-cyano-1-[trans-4-(trans-4-heptylcyclohexyl)-cyclohexyl]-cis-4-pentylcyclohexane
r-1-cyano-1-[trans-4-(trans-4-heptylcyclohexyl)-cyclohexyl]-cis-4-heptylcyclohexane
r-1-cyano-1-(trans-4-ethylcyclohexyl)-cis-4-(trans-4-ethylcyclohexyl)-cyclohexane
r-1-cyano-1-(trans-4-ethylcyclohexyl)-cis-4-(trans-4-propylcyclohexyl)-cyclohexane
r-1-cyano-1-(trans-4-ethylcyclohexyl)-cis-4-(trans-4-butylcyclohexyl)-cyclohexane
r-1-cyano-1-(trans-4-ethylcyclohexyl)-cis-4-(trans-4-pentylcyclohexyl)-cyclohexane
r-1-cyano-1-(trans-4-ethylcyclohexyl)-cis-4-(trans-4-hexylcyclohexyl)-cyclohexane
r-1-cyano-1-(trans-4-ethylcyclohexyl)-cis-4-(trans-4-heptylcyclohexyl)-cyclohexane
r-1-cyano-1-(trans-4-propylcyclohexyl)-cis-4-(trans-4-ethylcyclohexyl)-cyclohexane
r-1-cyano-1-(trans-4-propylcyclohexyl)-cis-4-(trans-4-propylcyclohexyl)-cyclohexane
r-1-cyano-1-(trans-4-propylcyclohexyl)-cis-4-(trans-4-butylcyclohexyl)-cyclohexane
r-1-cyano-1-(trans-4-propylcyclohexyl)-cis-4-(trans-4-pentylcyclohexyl)-cyclohexane
r-1-cyano-1-(trans-4-propylcyclohexyl)-cis-4-(trans-4-hexylcyclohexyl)-cyclohexane
r-1-cyano-1-(trans-4-propylcyclohexyl)-cis-4-(trans-4-heptylcyclohexyl)-cyclohexane
r-1-cyano-1-(trans-4-butylcyclohexyl)-cis-4-(trans-4-ethylcyclohexyl)-cyclohexane
r-1-cyano-1-(trans-4-butylcyclohexyl)-cis-4-(trans-4-propylcyclohexyl)-cyclohexane
r-1-cyano-1-(trans-4-butylcyclohexyl)-cis-4-(trans-4-butylcyclohexyl)-cyclohexane
r-1-cyano-1-(trans-4-butylcyclohexyl)-cis-4-(trans-4-pentylcyclohexyl)-cyclohexane
r-1-cyano-1-(trans-4-butylcyclohexyl)-cis-4-(trans-4-hexylcyclohexyl)-cyclohexane
r-1-cyano-1-(trans-4-butylcyclohexyl)-cis-4-(trans-4-heptylcyclohexyl)-cyclohexane
r-1-cyano-1-(trans-4-pentylcyclohexyl)-cis-4-(trans-4-ethylcyclohexyl)-cyclohexane
r-1-cyano-1-(trans-4-pentylcyclohexyl)-cis-4-(trans-4-propylcyclohexyl)-cyclohexane, m.p. 61°, c.p. 198°
r-1-cyano-1-(trans-4-pentylcyclohexyl)-cis-4-(trans-4-butylcyclohexyl)-cyclohexane
r-1-cyano-1-(trans-4-pentylcyclohexyl)-cis-4-(trans-4-pentylcyclohexyl)-cyclohexane, m.p. 33°, c.p. 199°
r-1-cyano-1-(trans-4-pentylcyclohexyl)-cis-4-(trans-4-hexylcyclohexyl)-cyclohexane
r-1-cyano-1-(trans-4-pentylcyclohexyl)-cis-4-(trans-4-heptylcyclohexyl)-cyclohexane, m.p. 44°, c.p. 192°
r-1-cyano-1-(trans-4-hexylcyclohexyl)-cis-4-(trans-4-ethylcyclohexyl)-cyclohexane
r-1-cyano-1-(trans-4-hexylcyclohexyl)-cis-4-(trans-4-propylcyclohexyl)-cyclohexane
r-1-cyano-1-(trans-4-hexylcyclohexyl)-cis-4-(trans-4-butylcyclohexyl)-cyclohexane
r-1-cyano-1-(trans-4-hexylcyclohexyl)-cis-4-(trans-4-pentylcyclohexyl)-cyclohexane
r-1-cyano-1-(trans-4-hexylcyclohexyl)-cis-4-(trans-4-hexylcyclohexyl)-cyclohexane
r-1-cyano-1-(trans-4-hexylcyclohexyl)-cis-4-(trans-4-heptylcyclohexyl)-cyclohexane
r-1-cyano-1-(trans-4-heptylcyclohexyl)-cis-4-(trans-4-ethylcyclohexyl)-cyclohexane
r-1-cyano-1-(trans-4-heptylcyclohexyl)-cis-4-(trans-4-propylcyclohexyl)-cyclohexane
r-1-cyano-1-(trans-4-heptylcyclohexyl)-cis-4-(trans-4-butylcyclohexyl)-cyclohexane
r-1-cyano-1-(trans-4-heptylcyclohexyl)-cis-4-(trans-4-pentylcyclohexyl)-cyclohexane
r-1-cyano-1-(trans-4-heptylcyclohexyl)-cis-4-(trans-4-hexylcyclohexyl)-cyclohexane
r-1-cyano-1-(trans-4-heptylcyclohexyl)-cis-4-(trans-4-heptylcyclohexyl)-cyclohexane
r-1-cyano-1-(trans-4-octylcyclohexyl)-cis-4-(trans-4-ethylcyclohexyl)-cyclohexane
r-1-cyano-1-(trans-4-octylcyclohexyl)-cis-4-(trans-4-propylcyclohexyl)-cyclohexane
r-1-cyano-1-(trans-4-octylcyclohexyl)-cis-4-(trans-4-butylcyclohexyl)-cyclohexane
r-1-cyano-1-(trans-4-octylcyclohexyl)-cis-4-(trans-4-pentylcyclohexyl)-cyclohexane, m.p. 60°, c.p. 187,5°
r-1-cyano-1-(trans-4-octylcyclohexyl)-cis-4-(trans-4-hexylcyclohexyl)-cyclohexane
r-1-cyano-1-(trans-4-octylcyclohexyl)-cis-4-(trans-4-heptylcyclohexyl)-cyclohexane
r-1-cyano-1-(trans-4-methoxycyclohexyl)-cis-4-(trans4-ethylcyclohexyl)-cyclohexane
r-1-cyano-1-(trans-4-methoxycyclohexyl)-cis-4-(trans4-propylcyclohexyl)-cyclohexane
r-1-cyano-1-(trans-4-methoxycyclohexyl)-cis-4-(trans4-butylcyclohexyl)-cyclohexane
r-1-cyano-1-(trans-4-methoxycyclohexyl)-cis-4-(trans-4-pentylcyclohexyl)-cyclohexane r-1-cyano-1-(trans-4-methoxycyclohexyl)-cis-4-(trans-4-hexylcyclohexyl)-cyclohexane
r-1-cyano-1-(trans-4-methoxycyclohexyl)-cis-4-(trans-4-heptylcyclohexyl)-cyclohexane
r-1-cyano-1-(trans-4-ethoxycyclohexyl)-cis-4-(trans-4-ethylcyclohexyl)-cyclohexane
r-1-cyano-1-(trans-4-ethoxycyclohexyl)-cis-4-(trans-4-propylcyclohexyl)-cyclohexane
r-1-cyano-1-(trans-4-ethoxycyclohexyl)-cis-4-(trans-4-butylcyclohexyl)-cyclohexane
r-1-cyano-1-(trans-4-ethoxycyclohexyl)-cis-4-(trans-4-pentylcyclohexyl)-cyclohexane
r-1-cyano-1-(trans-4-ethoxycyclohexyl)-cis-4-(trans-4-hexylcyclohexyl)-cyclohexane
r-1-cyano-1-(trans-4-ethoxycyclohexyl)-cis-4-(trans-4-heptylcyclohexyl)-cyclohexane
r-1-cyano-1-(trans-4-propoxycyclohexyl)-cis-4-(trans-4-ethylcyclohexyl)-cyclohexane
r-1-cyano-1-(trans-4-propoxycyclohexyl)-cis-4-(trans-4-propylcyclohexyl)-cyclohexane
r-1-cyano-1-(trans-4-propoxycyclohexyl)-cis-4-(trans-4-butylcyclohexyl)-cyclohexane
r-1-cyano-1-(trans-4-propoxycyclohexyl)-cis-4-(trans-4-pentylcyclohexyl)-cyclohexane
r-1-cyano-1-(trans-4-propoxycyclohexyl)-cis-4-(trans-4-hexylcyclohexyl)-cyclohexane
r-1-cyano-1-(trans-4-propoxycyclohexyl)-cis-4-(trans-4-heptylcyclohexyl)-cyclohexane
r-1-cyano-1-(trans-4-butoxycyclohexyl)-cis-4-(trans-4-ethylcyclohexyl)-cyclohexane
r-1-cyano-1-(trans-4-butoxycyclohexyl)-cis-4-(trans-4-propylcyclohexyl)-cyclohexane
r-1-cyano-1-(trans-4-butoxycyclohexyl)-cis-4-(trans-4-butylcyclohexyl)-cyclohexane
r-1-cyano-1-(trans-4-butoxycyclohexyl)-cis-4-(trans-4-pentylcyclohexyl)-cyclohexane
r-1-cyano-1-(trans-4-butoxycyclohexyl)-cis-4-(trans-4-hexylcyclohexyl)-cyclohexane
r-1-cyano-1-(trans-4-butoxycyclohexyl)-cis-4-(trans-4-heptylcyclohexyl)-cyclohexane
r-1-cyano-1-ethyl-cis-4-[p-(trans-4-propylcyclohexyl)-phenyl]-cyclohexane
r-1-cyano-1-propyl-cis-4-[p-(trans-4-propylcyclohexyl)-phenyl]-cyclohexane
r-1-cyano-1-butyl-cis-4-[p-(trans-4-propylcyclohexyl)-phenyl]-cyclohexane
r-1-cyano-1-pentyl-cis-4-[p-(trans-4-propylcyclohexyl)-phenyl]-cyclohexane
r-1-cyano-1-heptyl-cis-4-[p-(trans-4-propylcyclohexyl)-phenyl]-cyclohexane
r-1-cyano-1-ethyl-cis-4-[p-(trans-4-butylcyclohexyl)-phenyl]-cyclohexane
r-1-cyano-1-propyl-cis-4-[p-(trans-4-butylcyclohexyl)-phenyl]-cyclohexane
r-1-cyano-1-butyl-cis-4-[p-(trans-4-butylcyclohexyl)-phenyl]-cyclohexane
r-1-cyano-1-pentyl-cis-4-[p-(trans-4-butylcyclohexyl)-phenyl]-cyclohexane
r-1-cyano-1-heptyl-cis-4-[p-(trans-4-butylcyclohexyl)-phenyl]-cyclohexane
r-1-cyano-1-ethyl-cis-4-[p-(trans-4-pentylcyclohexyl)-phenyl]-cyclohexane
r-1-cyano-1-propyl-cis-4-[p-(trans-4-pentylcyclohexyl)-phenyl]-cyclohexane
r-1-cyano-1-butyl-cis-4-[p-(trans-4-pentylcyclohexyl)-phenyl]-cyclohexane
r-1-cyano-1-pentyl-cis-4-[p-(trans-4-pentylcyclohexyl)-phenyl]-cyclohexane
r-1-cyano-1-heptyl-cis-4-[p-(trans-4-pentylcyclohexyl)-phenyl]-cyclohexane
r-1-cyano-1-propyl-cis-4-[4-(trans-4-propylcyclohexyl)-biphenyl-4'-yl]-cyclohexane
r-1-cyano-1-butyl-cis-4-[4-(trans-4-propylcyclohexyl)-biphenyl-4'-yl-cyclohexane
r-1-cyano-1-pentyl-cis-4-[4-(trans-4-propylcyclohexyl)-biphenyl-4'-yl]-cyclohexane
r-1-cyano-1-heptyl-cis-4-[4-(trans-4-propylcyclohexyl)-biphenyl-4'-yl]-cyclohexane
r-1-cyano-1-ethyl-cis-4-[4-(trans-4-pentylcyclohexyl)-biphenyl-4'-yl]-cyclohexane
r-1-cyano-1-propyl-cis-4-[4-(trans-4-pentylcyclohexyl)-biphenyl-4'-yl]-cyclohexane
r-1-cyano-1-butyl-cis-4-[4-(trans-4-pentylcyclohexyl)-biphenyl-4'-yl]-cyclohexane
r-1-cyano-1-pentyl-cis-4-[4-(trans-4-pentylcyclohexyl)-biphenyl-4'-yl]-cyclohexane
r-1-cyano-1-heptyl-cis-4-[4-(trans-4-pentylcyclohexyl)-biphenyl-4'-yl]-cyclohexane

EXAMPLE 21

6 g of NaH (50% in paraffin) are added under stirring to a solution of 26.3 g of 4'-pentyl-biphenylyl-4-acetonitrile [m.p. 80°, c.p. −10°; obtainable from 4-acetyl-4'-pentyl-biphenyl by 4'-pentyl-biphenylylacetic acid (m.p. 160°) and the corresponding amide (m.p. 185°)/in 150 ml of dimethylsulfoxide.

Subsequently a solution of 30 g of 1-bromo-3-(2-bromoethyl)-n-hexane in 50 ml of dioxane is added, whereas the temperature is kept under 35° by cooling. The mixture is stirred for 2 hours and, after addition of isopropanol, worked up as customary. r-1-cyano-1-(4'-pentyl-4-biphenylyl)-cis-4-propylcyclohexane is obtained.

The following compounds are prepared analogously from the corresponding acetonitriles and the corresponding dibromides:
r-1-cyano-1-(4'-pentyl-4-biphenylyl)-cis-4-ethylcyclohexane
r-1-cyano-1-(4'-pentyl-4-biphenylyl)-cis-4-butylcyclohexane
r-1-cyano-1-(4'-pentyl-4-biphenylyl)-cis-4-pentylcyclohexane
r-1-cyano-1-(4'-pentyl-4-biphenylyl)-cis-4-heptylcyclohexane
r-1-cyano-1-(4'-propyl-4-biphenylyl)-cis-4-ethylcyclohexane
r-1-cyano-1-(4'-propyl-4-biphenylyl)-cis-4-propylcyclohexane
r-1-cyano-1-(4'-propyl-4-biphenylyl)-cis-4-butylcyclohexane
r-1-cyano-1-(4'-propyl-4-biphenylyl)-cis-4-pentylcyclohexane
r-1-cyano-1-(4'-propyl-4-biphenylyl)-cis-4-heptylcyclohexane
r-1-cyano-1-(4'-butyl-4-biphenylyl)-cis-4-ethylcyclohexane
r-1-cyano-1-(4'-butyl-4-biphenylyl)-cis-4-propylcyclohexane
r-1-cyano-1-(4'-butyl-4-biphenylyl)-cis-4-butylcyclohexane
r-1-cyano-1-(4'-butyl-4-biphenylyl)-cis-4-pentylcyclohexane
r-1-cyano-1-(4'-butyl-4-biphenylyl)-cis-4-heptylcyclohexane
r-1-cyano-1-(4'-heptyl-4-biphenylyl)-cis-4-ethylcyclohexane r-1-cyano-1-(4'-heptyl-4-biphenylyl)-cis-4-propylcyclohexane
r-1-cyano-1-(4'-heptyl-4-biphenylyl)-cis-4-butylcyclohexane
r-1-cyano-1-(4'-heptyl-4-biphenylyl)-cis-4-pentylcyclohexane
r-1-cyano-1-(4'-heptyl-4-biphenylyl)-cis-4-heptylcyclohexane
r-1-cyano-1-(p-ethylphenyl)-cis-4-(trans-4-ethylcyclohexyl)cyclohexane
r-1-cyano-1-(p-ethylphenyl)-cis-4-(trans-4-propylcyclohexyl)cyclohexane
r-1-cyano-1-(p-ethylphenyl)-cis-4-(trans-4-butylcyclohexyl)cyclohexane
r-1-cyano-1-(p-ethylphenyl)-cis-4-(trans-4-pentylcyclohexyl)cyclohexane
r-1-cyano-1-(p-ethylphenyl)-cis-4-(trans-4-heptylcyclohexyl)cyclohexane
r-1-cyano-1-(p-propylphenyl)-cis-4-(trans-4-ethylcyclohexyl)cyclohexane
r-1-cyano-1-(p-propylphenyl)-cis-4-(trans-4-propylcyclohexyl)cyclohexane
r-1-cyano-1-(p-propylphenyl)-cis-4-(trans-4-butylcyclohexyl)cyclohexane
r-1-cyano-1-(p-propylphenyl)-cis-4-(trans-4-pentylcyclohexyl)cyclohexane
r-1-cyano-1-(p-propylphenyl)-cis-4-(trans-4-heptylcyclohexyl)cyclohexane
r-1-cyano-1-(p-butylphenyl)-cis-4-(trans-4-ethylcyclohexyl)cyclohexane
r-1-cyano-1-(p-butylphenyl)-cis-4-(trans-4-propylcyclohexyl)cyclohexane
r-1-cyano-1-(p-butylphenyl)-cis-4-(trans-4-butylcyclohexyl)cyclohexane
r-1-cyano-1-(p-butylphenyl)-cis-4-(trans-4-pentylcyclohexyl)cyclohexane
r-1-cyano-1-(p-butylphenyl)-cis-4-(trans-4-heptylcyclohexyl)cyclohexane
r-1-cyano-1-(p-pentylphenyl)-cis-4-(trans-4-ethylcyclohexyl)cyclohexane
r-1-cyano-1-(p-pentylphenyl)-cis-4-(trans-4-propylcyclohexyl)cyclohexane
r-1-cyano-1-(p-pentylphenyl)-cis-4-(trans-4-butylcyclohexyl)cyclohexane
r-1-cyano-1-(p-pentylphenyl)-cis-4-(trans-4-pentylcyclohexyl)cyclohexane
r-1-cyano-1-(p-pentylphenyl)-cis-4-(trans-4-heptylcyclohexyl)cyclohexane
r-1-cyano-1-(p-heptylphenyl)-cis-4-(trans-4-ethylcyclohexyl)cyclohexane
r-1-cyano-1-(p-heptylphenyl)-cis-4-(trans-4-propylcyclohexyl)cyclohexane
r-1-cyano-1-(p-heptylphenyl)-cis-4-(trans-4-butylcyclohexyl)cyclohexane
r-1-cyano-1-(p-heptylphenyl)-cis-4-(trans-4-pentylcyclohexyl)cyclohexane
r-1-cyano-1-(p-heptylphenyl)-cis-4-(trans-4-heptylcyclohexyl)cyclohexane
r-1-cyano-1-(4-propylcyclohex-1-enyl)-cis-4-(trans-4-ethylcyclohexyl)-cyclohexane
r-1-cyano-1-(4-propylcyclohex-1-enyl)-cis-4-(trans-4-propylcyclohexyl)-cyclohexane
r-1-cyano-1-(4-propylcyclohex-1-enyl)-cis-4-(trans-4-butylcyclohexyl)-cyclohexane
r-1-cyano-1-(4-propylcyclohex-1-enyl)-cis-4-(trans-4-pentylcyclohexyl)-cyclohexane
r-1-cyano-1-(4-propylcyclohex-1-enyl)-cis-4-(trans-4-heptylcyclohexyl)-cyclohexane
r-1-cyano-1-(4-butylcyclohex-1-enyl)-cis-4-(trans-4-ethylcyclohexyl)-cyclohexane
r-1-cyano-1-(4-butylcyclohex-1-enyl)-cis-4-(trans-4-propylcyclohexyl)-cyclohexane
r-1-cyano-1-(4-butylcyclohex-1-enyl)-cis-4-(trans-4-butylcyclohexyl)-cyclohexane
r-1-cyano-1-(4-butylcyclohex-1-enyl)-cis-4-(trans-4-pentylcyclohexyl)-cyclohexane
r-1-cyano-1-(4-butylcyclohex-1-enyl)-cis-4-(trans-4-heptylcyclohexyl)-cyclohexane
r-1-cyano-1-(4-pentylcyclohex-1-enyl)-cis-4-(trans-4-ethylcyclohexyl)-cyclohexane
r-1-cyano-1-(4-pentylcyclohex-1-enyl)-cis-4-(trans-4-propylcyclohexyl)-cyclohexane
r-1-cyano-1-(4-pentylcyclohex-1-enyl)-cis-4-(trans-4-butylcyclohexyl)-cyclohexane
r-1-cyano-1-(4-pentylcyclohex-1-enyl)-cis-4-(trans-4-pentylcyclohexyl)-cyclohexane, m.p. 34°, c.p. 137°
r-1-cyano-1-(4-pentylcyclohex-1-enyl)-cis-4-(trans-4-heptylcyclohexyl)-cyclohexane, m.p. 30°, c.p. 133°
r-1-cyano-1-[4-(trans-4-propylcyclohexyl)-cyclohex-1-enyl)cis-4-ethylcyclohexane
r-1-cyano-1-[4-(trans-4-propylcyclohexyl)-cyclohex-1-enyl)cis-4-propylcyclohexane
r-1-cyano-1-[4-(trans-4-propylcyclohexyl)-cyclohex-1-enyl)cis-4-butylcyclohexane
r-1-cyano-1-[4-(trans-4-propylcyclohexyl)-cyclohex-1-enyl)cis-4-pentylcyclohexane
r-1-cyano-1-[4-(trans-4-propylcyclohexyl)-cyclohex-1-enyl)cis-4-heptylcyclohexane
r-1-cyano-1-[4-(trans-4-butylcyclohexyl)-cyclohex-1-enyl)cis-4-ethylcyclohexane
r-1-cyano-1-[4-(trans-4-butylcyclohexyl)-cyclohex-1-enyl)cis-4-propylcyclohexane
r-1-cyano-1-[4-(trans-4-butylcyclohexyl)-cyclohex-1-enyl)cis-4-butylcyclohexane
r-1-cyano-1-[4-(trans-4-butylcyclohexyl)-cyclohex-1-enyl)cis-4-pentylcyclohexane
r-1-cyano-1-[4-(trans-4-butylcyclohexyl)-cyclohex-1-enyl)cis-4-heptylcyclohexane
r-1-cyano-1-[4-(trans-4-pentylcyclohexyl)-cyclohex-1-enyl)cis-4-ethylcyclohexane
r-1-cyano-1-[4-(trans-4-pentylcyclohexyl)-cyclohex-1-enyl)cis-4-propylcyclohexane
r-1-cyano-1-[4-(trans-4-pentylcyclohexyl)-cyclohex-1-enyl)cis-4-butylcyclohexane
r-1-cyano-1-[4-(trans-4-pentylcyclohexyl)-cyclohex-1-enyl)cis-4-pentylcyclohexane
r-1-cyano-1-[4-(trans-4-pentylcyclohexyl)-cyclohex-1-enyl)cis-4-heptylcyclohexane
r-1-cyano-1-(4-ethylcyclohex-1-enyl)-cis-4-propylcyclohexane
r-1-cyano-1-(4-propylcyclohex-1-enyl)-cis-4-propylcyclohexane
r-1-cyano-1-(4-butylcyclohex-1-enyl)-cis-4-propylcyclohexane
r-1-cyano-1-(4-pentylcyclohex-1-enyl)-cis-4-propylcyclohexane
r-1-cyano-1-(4-heptylcyclohex-1-enyl)-cis-4-propylcyclohexane
r-1-cyano-1-(4-ethylcyclohex-1-enyl)-cis-4-butylcyclohexane
r-1-cyano-1-(4-propylcyclohex-1-enyl)-cis-4-butylcyclohexane
r-1-cyano-1-(4-butylcyclohex-1-enyl)-cis-4-butylcyclohexane
r-1-cyano-1-(4-pentylcyclohex-1-enyl)-cis-4-butylcyclohexane r-1-cyano-1-(4-heptylcyclohex-1-enyl)-cis-4-butylcyclohexane
r-1-cyano-1-(4-ethylcyclohex-1-enyl)-cis-4-pentylcyclohexane
r-1-cyano-1-(4-propylcyclohex-1-enyl)-cis-4-pentylcyclohexane
r-1-cyano-1-(4-butylcyclohex-1-enyl)-cis-4-pentylcyclohexane
r-1-cyano-1-(4-pentylcyclohex-1-enyl)-cis-4-pentylcyclohexane
r-1-cyano-1-(4-heptylcyclohex-1-enyl)-cis-4-pentylcyclohexane

EXAMPLE 22

26 g of phosphorus oxytrichloride are added dropwise, at 50° C., to a solution of 12.1 g of p-[trans-4-(trans-4-n-pentyl-4-methylcyclohexyl)-cyclohexyl]-benzamide [obtainable from 4-n-pentyl-4-methylcyclohexanone by reaction with a Grignard solution obtained from p-bromoanisole, elimination of water, hydrogenation of the resulting double bond, cleavage of the ether, hydrogenation of the aromatic ring, dehydrogenation to give the cyclohexanone, reaction with phenyl magnesium bromide, elimination of water, hydrogenation of the resulting double bond, Friedel-Crafts acylation with acetyl chloride/AlCl$_3$, haloform degradation of the resulting acetophenone to give p-[trans-4-(trans-4-n-pentyl-4-methylcyclohexyl)-cyclohexyl]-benzoic acid and conversion to its amide] in 100 ml of dimethylformamide. After 1 hour, the reaction mixture is worked up in the customary manner. p-[trans-(trans-4-n-Pentyl-4-methylcyclohexyl)cyclohexyl]-benzonitrile is obtained.

The following compounds are obtained in an analogous manner: p0 p-[trans-4-(trans-4-hexyl-4-methylcyclohexyl)-cyclohexyl]benzonitrile p0 p-[trans-4-(trans-4-heptyl-4-methylcyclohexyl)-cyclohexyl]-benzonitrile p0 p-[trans-4-(trans-4-butyl-4-methylcyclohexyl)-cyclohexyl]benzonitrile p0 p-[trans-4-(trans-4-propyl-4-methylcyclohexyl)-cyclohexyl]-benzonitrile
p-[trans-4-(trans-4-ethyl-4-methylcyclohexyl)-cyclohexyl]benzonitrile

EXAMPLE 23

A solution of 2.7 g of 4-cyano-3-fluorophenol and 5 ml of pyridine in 30 ml of toluene is added dropwise to a solution of 6.1 g of p-(4-methyl-4-n-pentylcyclohexyl)benzoyl chloride [obtainable by reaction of the enamine, obtainable from 2-methylheptanal and pyrrolidine, with methyl vinyl ketone according to G. Otani and S. Yamada, Chem. Pharm. Bull. 21(10), 2112–2118 (1973), hydrogenation of the resulting 4-methyl-4-pentyl-2-cyclohexanone to give 4-methyl-4-pentylcyclohexanone (an intermediate of the formula (A)), reaction With phenyl magnesium bromide, hydrolysis and hydrogenation to 4-methyl-4-n-pentylcyclohexylbenzene, reaction with acetyl chloride in the presence of aluminium chloride, subsequent haloform degradation of the resulting acetophenone to give the corresponding benzoic acid and conversion to the acid chloride] in 40 ml of toluene, and the mixture is boiled for 2 hours. After the customary working-up, 4-cyano-3-fluorophenyl p-(4-methyl-4-n-pentylcyclohexyl)benzoate is obtained.

The following compounds are prepared in an analogous manner:
4-cyano-3-fluorophenyl p-(4-methyl-4-ethylcyclohexyl)benzoate
4-cyano-3-fluorophenyl p-(4-methyl-4-propylcyclohexyl)benzoate
4-cyano-3-fluorophenyl p-(4-methyl-4-butylcyclohexyl)benzoate
4-cyano-3-fluorophenyl p-(4-methyl-4-hexylcyclohexyl)benzoate
4-cyano-3-fluorophenyl p-(4-methyl-4-heptylcyclohexyl)benzoate.

EXAMPLE 24

62,5 ml of butyllithium dissolved in hexane (1,6 m) and 37,7 g of trans-1-(trans-4-cyanocyclohexyl)-4-(trans-4-n-pentylcyclohexyl)-cyclohexane (described in German Patent Application P 3,426,035) dissolved in 40 ml of toluene are added subsequently to a solution of 10,1 g diisopropylamine in 70 ml of THF under nitrogen atmosphere at −10°. The mixture is stirred For 20 minutes.

Subsequently 14,2 g of methyljodide is added at −10°. the mixture is stirred for another 20 minutes at room temperature and worked up as customary. r-1-cyano-1-methyl-trans-4/trans-4-(trans-4-n-pentylcyclohexyl)cyclohexy-1/-cyclohexane is obtained.

The following positive materials are obtained in an analogous manner:
r-1-cyano-1-methyl-trans-4-[trans-4-(trans-4-ethylcyclohexyl)-cyclohexyl]-cyclohexane
r-1-cyano-1-methyl-trans-4-[trans-4-(trans-4-propylcyclohexyl)-cyclohexyl]-cyclohexane
r-1-cyano-1-methyl-trans-4-[trans-4-(trans-4-butylcyclohexyl)-cyclohexyl]-cyclohexane
r-1-cyano-1-methyl-trans-4-[trans-4-(trans-4-hexylcyclohexyl)-cyclohexyl]-cyclohexane
r-1-cyano-1-methyl-trans-4-[trans-4-(trans-4-heptylcyclohexyl)-cyclohexyl]-cyclohexane
r-1-cyano-1-methyl-trans-4-[trans-4-(trans-4-octylcyclohexyl)-cyclohexyl]-cyclohexane
r-1-cyano-1-methyl-trans-4-[trans-4-trans-4-nonylcyclohexyl)-cyclohexyl]-cyclohexane
r-1-cyano-1-methyl-trans-4-[trans-4-(trans-4-decylcyclohexyl)-cyclohexyl]-cyclohexane The following negative materials are obtained in an analogous manner by alkylation with appropriate alkyl halides:
r-1-cyano-1-ethyl-cis-4-[trans-4-(trans-4-ethylcyclohexyl)-cyclohexyl]-cyclohexane
r-1-cyano-1-ethyl-cis-4-[trans-4-(trans-4-propylcyclohexyl)-cyclohexyl]-cyclohexane
r-1-cyano-1-ethyl-cis-4-[trans-4-(trans-4-butylcyclohexyl)-cyclohexyl]-cyclohexane
r-1-cyano-1-ethyl-cis-4-[trans-4-(trans-4-pentylcyclohexyl)-cyclohexyl]-cyclohexane
r-1-cyano-1-ethyl-cis-4-[trans-4-(trans-4-hexylcyclohexyl)-cyclohexyl]-cyclohexane
r-1-cyano-1-ethyl-cis-4-[trans-4-(trans-4-heptylcyclohexyl)-cyclohexyl]-cyclohexane
r-1-cyano-1-propyl-cis-[trans-4-(trans-4-ethylcyclohexyl)cyclohexyl]-cyclohexane
r-1-cyano-1-propyl-cis-[trans-4-(trans-4-propylcyclohexyl)-cyclohexyl]-cyclohexane
r-1-cyano-1-propyl-cis-[trans-4-(trans-4-butylcyclohexyl)-cyclohexyl]-cyclohexane
4-1-cyano-1-propyl-cis-[trans-4-(trans-4-pentylcyclohexyl)cyclohexyl]-cyclohexane
4-1-cyano-1-propyl-cis-[trans-4-(trans-4-hexylcyclohexyl)cyclohexyl]-cyclohexane
4-1-cyano-1-propyl-cis-[trans-4-(trans-4-heptylcyclohexyl)-cyclohexyl]-cyclohexane r-1-cyano-1-butyl-cis-4-[trans-4-(trans-4-ethylcyclohexyl)-cyclohexyl]-cyclohexane
r-1-cyano-1-butyl-cis-4-[trans-4-(trans-4-propylcyclohexyl)-cyclohexyl]-cyclohexane
r-1-cyano-1-butyl-cis-4-[trans-4-(trans-4-butylcyclohexyl)-cyclohexyl]-cyclohexane
r-1-cyano-1-butyl-cis-4-[trans-4-(trand-4-pentylcyclohexyl)-cyclohexyl]cyclohexane
r-1-cyano-1-butyl-cis-4-[trans-4-(trans-4-hexylcyclohexyl)-cyclohexyl]-cyclohexane
r-1-cyano-1-butyl-cis-4-]trans-4-(trans-4-heptylcyclohexyl)-cyclohexyl]-cyclohexane
r-1-cyano-1-pentyl-cis-[trans-4-(trans-(methylcyclohexyl)cyclohexyl]-cyclohexane
r-1-cyano-1-pentyl-cis-[trans-4-(trans-4-propylcyclohexyl)-cyclohexyl]-cyclohexane
r-1-cyano-1-pentyl-cis-[trans-4-(trans-4-butylcyclohexyl)cyclohexyl]-cyclohexane
4-1-cyano-1-pentyl-cis-[trans-4-(trans-4-pentylcyclohexyl)-cyclohexyl]-cyclohexane
4-1-cyano-1-pentyl-cis-[trans-4-(trans-4-hexylcyclohexyl)cyclohexyl]-cyclohexane
4-1-cyano-1-pentyl-cis-[trans-4-(trans-4-heptylcyclohexyl)-cyclohexyl]-cyclohexane
r-1-cyano-1-hexyl-cis-4-[trans-4-(trans-4-ethylcyclohexyl)-cyclohexyl]-cyclohexane
r-1-cyano-1-hexyl-cis-4-[trans-4-(trans-4-propylcyclohexyl)-cyclohexyl]-cyclohexane
r-1-cyano-1-hexyl-cis-4-[trans-4-(trans-4-butylcyclohexyl)-cyclohexyl]-cyclohexane
r-1-cyano-1-hexyl-cis-4-[trans-4-(trans-4-pentylcyclohexyl)-cyclohexyl]-cyclohexane
r-1-cyano-1-hexyl-cis-4-[trans-4-(trans-4-hexylcyclohexyl)-cyclohexyl]-cyclohexane
r-1-cyano-1-hexyl-cis-4-[trans-4-(trans-4-heptylcyclohexyl)-cyclohexyl]-cyclohexane
r-1-cyano-1-heptyl-cis-[trans-4-(trans-4-ethylcyclohexyl)cyclohexyl]-cyclohexane
r-1-cyano-1-heptyl-cis-[trans-4-(trans-4-propylcyclohexyl)-cyclohexyl]-cyclohexane
r-1-cyano-1-heptyl-cis-[trans-4-(trans-4-butylcyclohexyl)cyclohexyl]cyclohexane
4-1-cyano-1-heptyl-cis-[trans-4-(trans-4-pentylcyclohexyl)-cyclohexyl]-cyclohexane
4-1-cyano-1-heptyl-cis-[trans-4-(trans-4-hexylcyclohexyl)cyclohexyl]-cyclohexane
4-1-cyano-1-heptyl-cis-[trans-4-(trans-4-heptylcyclohexyl)-cyclohexyl]-cyclohexane.

EXAMPLE 25

A mixture of 12.4 g of 4-(trans-4-n-propylcyclohexyl)-1-methyl-3-cyclohexene-1-carbonitrile [obtainable by reaction of trans-4-propylcyclohexanecarboxylic acid chloride with vinyltrimethylsilane under AlCl3 catalysis according to J. P. Pillot, J. Dunogues and R. Calas, Bull. Soc. Chem. Fr. 2143 (1975); C.r. hebd. Seanc. Acad. Sci., Paris 278, 787, 789 (1974), reaction of the resulting trans-4-n-propylcyclohexyl vinyl ketone with the Tebbe reagent or with methylenetriphenylphosphorane by the Wittig method to give 2-(trans-4-n-propylcyclohexyl)-1,3-butadiene, and reaction of the diene with methyl methacrylate according to W. Kreiser, P. Below and L. Ernst, Liebigs Ann. Chem. 1985, 194; G. Bartels, thesis, Technical University of Braunschweig, 1978, to give methyl 4-(4-trans-n-propylcyclohexyl)-1-methyl-3-cyclohexene-1-carboxylate by a regiospecific route, and basic hydrolysis of the latter compound followed by conversion to the nitrile by the customary route, via the acid chloride and amide], 40 g of Raney nickel and 200 ml of ethanol is hydrogenated at room temperature. After the customary working-up, r-1-cyano-1-methyl-trans-4-(trans-4-n-propylcyclohexyl)-cyclohexane is obtained.

The following compounds are prepared in an analogous manner:
r-1-cyano-1-methyl-4-trans-4-(trans-4-ethylcyclohexyl)-cyclohexane
r-1-cyano-1-methyl-trans-4-(trans-4-butylcyclohexyl)-cyclohexane
r-1-cyano-1-methyl-trans-4-(trans-4-pentylcyclohexyl)-cyclohexane
r-1-cyano-1-methyl-trans-4-(trans-4-hexylcyclohexyl)-cyclohexane
r-1-cyano-methyl-trans-4-(trans-4-heptylcyclohexyl)cyclohexane.

EXAMPLE 26

A solution of 26.6 g of r-1-methyl-1-n-pentyl-cis-4-(trans-4-hydroxycyclohexyl)-cyclohexane [obtainable analogously to Example 22 by hydrogenation of the corresponding phenol] in 250 ml of tetrahydrofuran is added dropwise, at 50° C., to a stirred mixture of 22 g of n-butyl iodide and 8.9 g of KH in 250 ml of tetrahydrofuran, and stirring is continued for a further 2 hours at 50° C. After the customary working-up, r-1-methyl-1-n-pentyl-cis-4-(trans-4-butoxycyclohexyl)-cyclohexane is obtained.

The following compounds are prepared in an analogous manner:
r-1-methyl-1-pentyl-cis-4-(trans-4-ethoxycyclohexyl)-cyclohexane
r-1-methyl-1-pentyl-cis-4-(trans-4-propoxycyclohexyl)-cyclohexane
r-1-methyl-1-pentyl-cis-4-(trans-4-pentoxycyclohexyl)-cyclohexane
r-1-methyl-1-pentyl-cis-4-(trans-4-propionyloxycyclohexyl)-cyclohexane
r-1-methyl-1-pentyl-cis-4-(trans-4-butyryloxycyclohexyl)cyclohexane
r-1-methyl-1-propyl-cis-4-(trans-4-ethoxycyclohexyl)-cyclohexane
r-1-methyl-1-propyl-cis-4-(trans-4-propoxycyclohexyl)-cyclohexane
r-1-methyl-1-propyl-cis-4-(trans-4-pentoxycyclohexyl)-cyclohexane
r-1-methyl-1-propyl-cis-4-(trans-4-propionyloxycyclohexyl)-cyclohexane
r-1-methyl-1-propyl-cis-4-(trans-4-butyryloxycyclohexyl)cyclohexane.

The following compounds are obtained from r-1-methyl-1-n-pentyl-cis-4-hydroxyphenyl-cyclohexane [obtainable analogously to Example 22 by ether cleavage of the corresponding anisole] by etherification with an appropriate alkyl halide in the presence of potassium carbonate:
r-1-methyl-1-pentyl-cis-4-ethoxyphenyl-cyclohexane
r-1-methyl-1-pentyl-cis-4-propoxyphenyl-cyclohexane
r-1-methyl-1-pentyl-cis-4-butoxyphenyl-cyclohexane
r-1-methyl-1-pentyl-cis-4-pentoxyphenyl-cyclohexane
r-1-methyl-1-pentyl-cis-4-propionyloxyphenyl-cyclohexane
r-1-methyl-1-pentyl-cis-4-butyryloxyphenyl-cyclohexane
r-1-methyl-1-propyl-cis-4-ethoxyphenyl-cyclohexane
r-1-methyl-1-propyl-cis-4-propoxyphenyl-cyclohexane
r-1-methyl-1-propyl-cis-4-butoxyphenyl-cyclohexane r-1-methyl-1-propyl-cis-4-pentoxyphenyl-cyclohexane
r-1-methyl-1-propyl-cis-4-propionyloxyphenyl-cyclohexane
r-1-methyl-1-propyl-cis-4-butyryloxyphenyl-cyclohexane.

EXAMPLE 27

A mixture of 10.9 g of 1-methyl-1-n-pentyl-4-(p-(n-propyl)-phenyl)-3-cyclohexene [obtainable from 4-n-pentyl-4-methylcyclohexanone by reaction with a Grignard solution, obtained from p-(n-propyl)-bromobenzene, and elimination of water], 40 g of Raney nickel and 200 ml of ethanol is hydrogenated at room temperature. After the customary working-up, r-1-methyl-1-n-pentyl-cis-4-(p-(n-propyl)-phenyl)-cyclohexane is obtained.

The following compounds are prepared in an analogous manner:
r-1-methyl-1-pentyl-cis-4-(p-ethylphenyl)-cyclohexane
r-1-methyl-1-pentyl-cis-4-(p-butylphenyl)-cyclohexane
r-1-methyl-1-pentyl-cis-4-(p-pentylphenyl)-cyclohexane
r-1-methyl-1-pentyl-cis-4-(p-heptylphenyl)-cyclohexane
r-1-methyl-1-butyl-cis-4-(p-ethylphenyl)-cyclohexane
r-1-methyl-1-butyl-cis-4-(p-propylphenyl)-cyclohexane
r-1-methyl-1-butyl-cis-4-(p-butylphenyl)-cyclohexane
r-1-methyl-1-butyl-cis-4-(p-pentylphenyl)-cyclohexane
r-1-methyl-1-butyl-cis-4-(p-heptylphenyl)-cyclohexane
r-1-methyl-1-propyl-cis-4-(p-ethylphenyl)-cyclohexane
r-1-methyl-1-propyl-cis-4-(p-propylphenyl)-cyclohexane
r-1-methyl-1-propyl-cis-4-(p-butylphenyl)-cyclohexane
r-1-methyl-1-propyl-cis-4-(p-pentylphenyl)-cyclohexane
r-1-methyl-1-propyl-cis-4-(p-heptylphenyl)-cyclohexane.

EXAMPLE 28

2.9 g of 2-/4-(trans-4-n-pentylcyclohexyl)-1-cyanocyclohex-1-yl/-acetaldehyde /obtained by reaction of trans-1-(trans-4-cyanocyclohexyl)-4-n-pentylcyclohexane (described in German Patent 2,702,598) with ethylenoxide followed by conversion of the alcohol to the corresponding aldehyde by reaction with pyridimium chlorochromate/and 20 ml of ether are added to a mixture of 5.4 g of n-butyl-triphenylphosphoniumbromide in 100 ml/of ether and 7,4 ml of n-butyllithium in hexane (1,7M) at −40°. The mixture is stirred at −40° for 2 hours and warmed up. After the customary working-up and isomerisation, r-1-cyano-1-(trans-2-hexenyl)-cis-4-(trans-4-n-pentylcyclohexyl)-cyclohexane is obtained.

The following compounds are prepared in an analogous manner (the homologous aldehydes are prepared from the anion of trans-1-(trans-4-cyanocyclohexyl)-4-alkylcyclohexanes by reaction with formic acid ethyl ester, ethylen oxide or oxetane and subsequent reaction with pyridiniumchlorochromate, if necessary. The trans-alkenyl isomers are obtained by conventional isomerisation procedures):
r-1-cyano-1-(trans-2-butenyl)-cis-4-(trans-4-pentylcyclohexyl)-cyclohexane
r-1-cyano-1-(trans-2-pentenyl)-cis-4-(trans-4-pentylcyclohexyl)-cyclohexane
r-1-cyano-1-(trans-2-heptenyl)-cis-4-(trans-4pentylcyclohexyl)-cyclohexane
r-1-cyano-1-(trans-1-propenyl)-cis-4-(trans-4-propylcyclohexyl)-cyclohexane
r-1-cyano-1-(trans-1-butenyl)-cis-4-(trans-4-propylcyclohexyl)-cyclohexane
r-1-cyano-1-(trans-1-pentenyl)-cis-4-(trans-4-propylcyclohexyl)-cyclohexane
r-1-cyano-1-(trans-1-hexenyl)-cis-4-(trans-4-propylcyclohexyl)-cyclohexane
r-1-cyano-1-(trans-1-heptenyl)-cis-4-(trans-4-propylcyclohexyl)-cyclohexane
r-1-cyano-1-(trans-1-propenyl)-cis-4-(trans-4-bulylcyclohexyl)-cyclohexane
r-1-cyano-1-(trans-1-butenyl)-cis-4-(trans-4-butylcyclohexyl)-cyclohexane
r-1-cyano-1-(trans-1-pentenyl)-cis-4-(trans-4-butylcyclohexyl)-cyclohexane
r-1-cyano-1-(trans-1-hexenyl)-cis-4-(trans-4-butylcyclohexyl)-cyclohexane
r-1-cyano-1-(trans-1-heptenyl)-cis-4-(trans-4-butylcyclohexyl)-cyclohexane
r-1-cyano-1-(trans-1-propenyl)-cis-4-(trans-4-pentycyclohexyl)-cyclohexane
r-1-cyano-1-(trans-1-butenyl)-cis-4-(trans-4-penlylcyclohexyl)-cyclohexane
r-1-cyano-1-(trans-1-pentenyl)-cis-4-(trans-4-pentylcyclohexyl)-cyclohexane
r-1-cyano-1-(trans-1-hexenyl)-cis-4-(trans-4-pentylcyclohexyl)-cyclohexane
r-1-cyano-1-(trans-1-heptenyl)-cis-4-(trans-4-pentylcyclohexyl)-cyclohexane
r-1-cyano-1-(trans-1-propenyl)-cis-4-(trans-4-heptylcyclohexyl)-cyclohexane
r-1-cyano-1-(trans-1-butenyl)-cis-4-(trans-4-heptylcyclohexyl)-cyclohexane
r-1-cyano-1-(trans-1-pentenyl)-cis-4-(trans-4-heptylcyclohexyl)-cyclohexane
r-1-cyano-1-(trans-1-hexenyl)-cis-4-(trans-4-heplylcyclohexyl)-cyclohexane
r-1-cyano-1- (trans-1-heptenyl)-cis-4-(trans-4-heptylcyclohexyl)-cyclohexane
r-1-cyano-1-(trans-3-butenyl)-cis-4-(trans-4-propylcyclohexyl)-cyclohexane
r-1-cyano-1-(trans-3-pentenyl)-cis-4-(trans-4-propylcyclohexyl)-cyclohexane
r-1-cyano-1-(trans-3-hexenyl)-cis-4-(trans-4-propylcyclohexyl)-cyclohexane
r-1-cyano-1-(trans-3-heptenyl)-cis-4-(trans-4-propylcyclohexyl)-cyclohexane
r-1-cyano-1-(trans-3-butenyl)-cis-4-(trans-4-butylcyclohexyl)-cyclohexane
r-1-cyano-1-(trans-3-pentenyl)-cis-4-(trans-4-butylcyclohexyl)-cyclohexane
r-1-cyano-1-(trans-3-hexenyl)-cis-4-(trans-4-bulylcyclohexyl)-cyclohexane
r-1-cyano-1-(trans-3-heptenyl)-cis-4-(trans-4-butylcyclohexyl)-cyclohexane
r-1-cyano-1-(trans-)-butenyl)-cis-4-(trans-4-pentylcyclohexyl)-cyclohexane
r-1-cyano-1-(trans-3-pentenyl)-cis-4-(trans-4-pentylcyclohexyl)-cyclohexane
r-1-cyano-1-(trans-3-hexenyl)-cis-4-(trans-4-pentylcyclohexyl)-cyclohexane
r-1-cyano-1-(trans-3-heptenyl)-cis-4-(trans-4-pentylcyclohexyl)-cyclohexane
r-1-cyano-1-(trans-3-butenyl)-cis-4-(trans-4-heptylcyclohexyl)-cyclohexane
r-1-cyano-1-(trans-3-pentenyl)-cis-4-(trans-4-heptylcyclohexyl)-cyclohexane r-1-cyano-1-(trans-3-hexenyl)-cis-4-(trans-4-heptylcyclohexyl)-cyclohexane r-1-cyano-1-(trans-3-heptenyl)-cis-4-(trans-4-heptylcyclohexyl)-cyclohexane The following examples relate to liquid crystal phases according to the invention.

EXAMPLE A

A liquid crystal phase is prepared from:
15% of 2-p-cyanophenyl-5-propyl-1,3-dioxane,
23% of 2-p-cyanophenyl-5-butyl-1,3-dioxane,
17% of 2-p-cyanophenyl-5-pentyl-1,3-dioxane,
7% of 4-(4-cyano-4-propylcyclohexyl)-4'-pentylbiphenyl,
12% of 4-cyano-4-heptyl-4'-(trans-4-pentyl-cyclohexylcarbonyloxy)-bicyclohexane,
11% of methyl 4-propyl-4'-heptyl-bicyclohexyl-4'-carboxylate,
6% of p-cyanophenyl p-trans-4-ethylcyclohexyl-benzoate,
7% of p-cyanophenyl p-trans-4-pentylcyclohexylbenzoate and
2% of p-cyanophenyl p-(o-propylbenzoyloxy)-benzoate.

EXAMPLE B

A liquid crystal phase is prepared from:
17% of 2-p-cyanophenyl-5-propyl-1,3-dioxane,
25% of 2-p-cyanophenyl-5-butyl-1,3-dioxane,
19% of 2-p-cyanophenyl-5-pentyl-1,3-dioxane,
13% of 2-p-cyanophenyl-5-heptyl-1,3-dioxane,
0.5% of 4-(4-formyl-4-prooylcyclohexyl)-4'-pentylbiphenyl,
0.5% o-trans-4-pentylcyclohexyl-benzonitrile,
14% of 4-cyano-4'-(trans-4-pentylcyclohexyl)-biphenyl,
7% of p-ethoxyphenyl trans-4-propylcyclohexanecarboxylate and
4% of trans-4-propylcyclohexyl trans-4-pentylcyclohexanecarboxylate.

EXAMPLE C

A liquid crystal phase is prepared from:
9% of trans-4-propylcyclohexyl trans-4-propylcyclohexanecarboxylate,
7% of trans-4-propylcyclohexyl trans-4-pentylcyclohexanecarboxylate,
17% of 2-p-cyanophenyl-5-propyl-1,3-dioxane,
25% of 2-p-cyanophenyl-5-butyl-1,3-dioxane,
18% of 2-p-cyanophenyl-5-pentyl-1,3-dioxane,
7% of 1-fluoro-1-[4'-(trans-4-pentylcyclohexyl)-biphenyl-4-yl]-4-propylcyclohexane,
3% of 1-fluoro-1-[4'-(trans-4-propylcyclohexyl)-biphenyl-4-yl]-4-propylcyclohexane,
5% of 4-(trans-4-pentylcyclohexyl)-4'-(trans-4-propylcyclohexyl)-biphenyl and
9% of p-pentylphenyl p-methoxybenzoate.

EXAMPLE D

A liquid crystal phase of
10% of 4-pentyl-4'-heptyl-4'-ethylthiobicyclohexane,
17% of 4-pentyl-4'-heptyl-4'-ethylsulfonylbicyclohexane,
9% of 4-propyl-4'-methyl-4'-hexylsulofinylbicyclohexane,
27% of 4-propyl-4'-methyl-4'-heptylsulfinylbicyclohexane,
32% of 4-pentyl-4'-methyl-4'-pentylsulfonylbicyclohexane and
5% of 4-p-cyanophenyl-4'-pentyl-biphenyl has an excellent dissolving power for pleochroic dyestuffs and is suitable as a base mixture for positive guest-/host systems.

EXAMPLE E

A liquid crystal phase of
20% r-1-cyano-cis-4-(trans-4-butylcyclohexyl)-1-heptylcyclohexane,
21% r-1-cyano-cis-4-(trans-4-pentylcyclohexyl)-1-pentylcyclohexane,
11% trans,trans-4-propyl-4,-methoxycyclohexylcyclohexane,
10% trans,trans-4-propyl-4,-ethoxycyclohexylcyclohexane,
4% trans,trans-4-butylcyclohexyl-cyclohexane-4'-carboxylic acid-trans-4-propylcyclohexylester,
4% trans,trans-4-butylcyclohexyl-cyclohexane-4'-carboxylic acid-trans-4-pentylcyclohexylester,
4% trans,trans-4-propylcyclohexyl-cyclohexane-4'-carboxylic acid-trans-4-propylcyclohexylester,
4% trans,trans-4-propylcyclohexyl-cyclohexane-4'-carboxylic acid-trans-4-pentylcyclohexylester and
22% r-1-cyano-1-(trans-4-pentylcyclohexyl)-cis-4-(trans-4-pentylcyclohexyl)-cyclohexane has a clear point of 100° and an optical anisotropy of 0.04.

EXAMPLE F

A liquid-crystalline phase is prepared from
15% of 2-p-cyanophenyl-5-propyl-1,3-dioxane,
23% of 2-p-cyanophenyl-5-butyl-1,3-dioxane,
17% of 2-p-cyanophenyl-5-pentyl-1,3-dioxane,
7% of p-[trans-4-(trans-4-pentyl-4-methylcyclohexyl)-cyclohexyl]-benzonitrile,
12% of 4-cyano-4'-(trans-4-pentylcyclohexyl)-biphenyl,
11% of r-1-cyano-1-methyl-trans-4-(trans-4-propylcyclohexyl)-cyclohexane,
6% of p-cyanophenyl p-trans-4-ethylcyclohexylbenzoate,
7% of p-cyanophenyl p-trans-4-pentylcyclohexylbenzoate and
2% of p-cyanophenyl p-(p-propylbenzoyloxy)-benzoate.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cyclohexane derivative of the formula

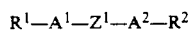

wherein
R$^1$ and R$^2$ independently are (a) C$_{1-15}$-alkyl, (b) C$_{1-15}$-alkyl substituted by halo or CN, (c) C$_{1-15}$-alkyl wherein one or two non-adjacent CH$_2$ groups are replaced by at least one of —O—, —CO—, —O—CO—, —CO—O—, —C≡C—, —CH=CH—, —S—, the maximum number of C-atoms still being 15, (d) F, (e) Cl, (f) Br, (g) CN or (h) $R^3-(A^3)_p-Z^2-$, $A^1$ is —A—, $-A^4-Z^3-A-$ or $-A-Z^3-A^4-$, A is 1,4-cyclohexylene which is additionally substituted in the 1- or 4-position by CN, $A^2$, $A^3$ and $A^4$ in each case independently are (a) 1,4-phenylene, (b) 1,4-phenylene substituted by one or two F, Cl, $CH_3$ or CN, (c) any of groups (a) or (b) wherein one or two CH groups are replaced by N atoms, (d) 1,4-cyclohexylene, (e) 1,4-cyclohexylene wherein one or two non-adjacent $CH_2$ groups are replaced by O-atoms, (f) 1,4-cyclohex-1-enyl, $Z^1$, $Z^2$ each independently are —CO—O—, —O—CO—, and $Z^3$ —$OCH_2$—, —$CH_2O$—, —$CH_2CH_2$— or a single bond, $R^3$ is (a) $C_{1-15}$-alkyl, (b) $C_{1-15}$-alkyl, substituted by halo or CN, (c) a group (a)-(b) wherein one or two non-adjacent $CH_2$ groups are replaced by one of —O—, —CO—, —O—CO—, —CO—O—, —C≡C—, —CH=CH— or —S—, the maximum number of C-atoms still being 15, (d) F, (e) Cl, (f) Br or (g) CN and $p$ is 1 or 2, and when p=2, the groups $A^3$ can be identical or different.

2. A compound of claim 1 of the formula $R^1-A-A^2-R^2$ or $R^1-A-Z^1-A^2-R^2$

3. A compound of claim 1 of the formula $R^1-A^4-A-A^2-R^2$ $R^1-A-A^4-A^2-R^2$ $R^3-A^3-A-A^2-R^2$ $R^1-A-A^2-A^3-R^3$ $R^1-A^4-Z^3-A-A^2-R^2$ $R^1-A-Z^3-A^4-A^2-R^2$ $R^1-A-Z^1-A^2-A^3-R^3$ $R^1-A^4-Z^3-A-A^2-R^2$ $R^1-A-Z^3-A^4-A^2-R^2$ $R^1-A^4-A-Z^1-A^2-R^2$ $R^1-A-A^4-Z^1-A^2-R$ $R^3-A^3-A-Z^1-A^2-R^2$ $R^1-A-A^2-Z^2-A^3-R^3$ $R^3-A^3-Z^2-A-A^2-R^2$ $R^3-A^3-Z^2-A-Z^1-A^2-R^2$ $R^1-A-Z^1-A^2-Z^2-A^3-R^3$ $R^1-A^4-Z^3-A-Z^1-A^2-R^2$ or
$R^1-A-Z^3-A^4-Z^1-A^2-R$ 4. A compound of claim 1 of the formula $R^3-A^3-A^4-A-A^2-R^2$ $R^3-A^3-A-A^4-A^2-R^2$ $R^1-A^4-A-A^2-A^3-R^3$ $R^1-A-A^4-A^2-A^3-R^3$ $R^3-A^3-A-A^2-A^3-R^3$ $R^3-A^3-A-A^2-R^3$ $R^1-A-A^2-A^3-R^3$ $R^3-A^3-Z^2-A-A^2-A^3-R^3$ $R^3-A^3-A-Z^1-A^2-A^3-R^3$ $R^3-A^3-A-Z^1-A^2-A^3-R^3$ $R^3-A^3-A-A^2-Z^2-A^3-R^3$ $R^1-A-A^4-Z^1-A^2-A^3-R^3$ $R^1-A^4-A-Z^1-A^2-A^3-R^3$ $R^3-A^3-A^4-A-Z^1-A^2-R^2$ $R^3-A^3-A-A^4-Z^1-A^2-R^2$ $R^1-A^4-A-A^2-Z^2-A^3-R^3$ $R^1-A-A^4-A^2-Z^2-A^3-R^3$ $R^3-A^3-Z^2-A^4-A-A^2-R^2$ $R^3-A^3-Z^2-A-A^4-A^2-R^2$ $R^3-A^3-A-A^2-Z^2-A^3-R^3$ $R^3-A^3-Z^2-A-A^2-A^3-R^3$ $R^3-A^3-A^3-A-Z^1-A^2-R^2$ $R^3-A^3-A^4-Z^3-A-A^2-R^2$ $R^3-A^3-A-Z^3-A^4-A^2-R^2$ $R^1-A-A^2-Z^2-A^3-A^3-R^3$ $R^1-A^4-Z^3-A-A^2-A^3-R^3$ $R^1-A-Z^3-A^4-A^2-A^3-R^3$ $R^3-A^3-A^3-Z^2-A-A^2-R^2$ $R^1-A-Z^1-A^2-A^3-A^3-R^3$ $R^3-A^3-Z^2-A^4-A-Z^1-A^2-R^2$ $R^3-A^3-Z^2-A-A^4-Z^1-A^2-R^2$ $R^1-A^4-A-Z^1-A^2-Z^2-A^3-R^3$ $R^1-A-A^4-Z^1-A^2-Z^2-A^3-R^3$ $R^3-A^3-A-Z^1-A^2-Z^2-A^3-R^3$ $R^3-A^3-Z^2-A-A^2-Z^2-A^3-R^3$ $R^3-A^3-Z^2-A-Z^1-A^2-A^3-R^3$ $R^3-A^3-A^4-Z^3-A-Z^1-A^2-R^2$ $R^3-A^3-A-Z^3-A^4-Z^1-A^2-R^2$ $R^1-A^4-Z^3-A-A^2-Z^2-A^3-R^3$ $R^1-A-Z^3-A^4-A^2-Z^2-A^3-R^3$ $R^3-A^3-Z^2-A^4-Z^3-A-A^2-R^2$ $R^3-A^3-Z^2-A-Z^3-A^4-A^2-R^2$ $$R^1—A—Z^1—A^2—Z^2—A^3—A^3—R^3$$

$$R^3—A^3—Z^2—A—Z^1—A^2—Z^2—A^3—R^3$$

$$R^3—A^3—Z^2—A^4—Z^3—A—Z^1—A^2—R^2$$

$$R^3—A^3—Z^2—A—Z^3—A^4—Z^1—A^2—R^2$$

$$R^1—A^4—Z^3—A—Z^1—A^2—Z^2—A^3—R^3 \text{ or}$$

$$R^1—A—Z^3—A^4—Z^1—A^2—Z^2—A^3—R^3$$

5. A phase of claim 1 of the formula $$R^3—A^3—A^4—A—A^2—A^3—R^3$$

$$R^3—A^3—A—A^4—A^2—A^3—R^3$$

$$R^3—A^3—A^4—A—A^2—A^3—R^3$$

$$R^3—A^3—A—A^4—A^2—A^3—R^3$$

$$R^1—A—A^4—A^2—A^3—A^3—R^3$$

$$R^3—A^3—A^4—A—A^2—Z^2—A^3—R^3$$

$$R^3—A^3—A—A^4—A^2—Z^2—A^3—R^3$$

$$R^3—A^3—A^4—A—Z^1—A^2—A^3—R^3$$

$$R^3—A^3—A—A^4—Z^1—A^2—A^3—R^3$$

$$R^3—A^3—Z^2—A^4—A—A^2—A^3—R^3$$

$$R^3—A^3—Z^2—A—A^4—A^2—A^3—R^3$$

$$R^3—A^3—A^4—A—Z^1—A^2—Z^2—A^3—R^3$$

$$R^3—A^3—A—A^4—Z^1—A^2—Z^2—A^3—R^3$$

$$R^3—A^3—Z^2—A^4—A—A^2—Z^2—A^3—R^3$$

$$R^3—A^3—Z^2—A—A^4—A^2—Z^2—A^3—R^3$$

$$R^3—A^3—Z^2—A^4—A—Z^1—A^2—A^3—R^3$$

$$R^3—A^3—Z^2—A—A^4—Z^1—A^2—A^3—R^3$$

$$R^3—A^3—Z^2—A^4—A—Z^1—A^2—Z^2—A^3—R^3$$

$$R^3—A^3—Z^2—A—A^4—Z^1—A^2—Z^2—A^3—R^3$$

$$R^1—A^4—Z^3—A—Z^1—A^2—Z^2—A^3—A^3—R^3$$

$$R^1—A—Z^3—A^4—Z^1—A^2—Z^2—A^3—A^3—R^3$$

$$R^3—A^3—A^3—Z^2—A—Z^1—A^2—Z_2—A^3—R_3 \text{ or}$$

$$R^3—A^3—Z^2—A—Z^1—A^2—Z^2—A^3—A^3—R^3$$

6. A phase of claim 1 of the formula $$R^1—Phe—Z^1—A\text{-}R^2$$

$$R^1—Cy—Z^1—A—R^2$$

$$R^1—Dio—Z^1—A—R^2$$

$$R^1—Pyr—Z^1—A—R^2$$

$$R^1—Phe—Z^1—A—Z^2—Phe\text{-}R^2$$

$$R^1—Dio—Z^1—A—Z^2—Cy—R^2$$

$$R^1—Cy—Z^1—A—Z^2—Phe—R^2$$

$$R^1—Cy—Z^1—A—Z^2—Cy—R^2$$

$$R^1—Phe—Phe—Z^1—A—R^2$$

$$R^1—Phe—Cy—Z^1—A—R_2$$

$$R^1—Phe—Phe—Z^1—A—Z^2—Phe\text{-}R^2$$

$$R^1—Phe—Phe—Z^1—A—Z^2—Cy—R^2$$

$$R^1—Phe—Cy—Z^1—A—Z^2—Phe—R^2$$

$$R^1—Phe—Cy—Z^1—A—Z^2—Cy—R^2$$

$$R^1—Cy—Phe—Z^1—A—Z^2—Phe—R^2$$

$$R^1—Cy—Phe—Z^1—A—Z^2—Cy—R^2$$

$$R^1—Cy—Cy—Z^1—A—Z^2—Phe—R^2$$

$$R^1—Cy—Cy—Z^1—A—Z^2—Cy—R^2$$

wherein the Phe is 1,4-phenylene, Cy is 1,4-cyclohexylene, Dio is 1,3-dioxane-2,5-diyl and Pyr is pyrimidine-2,5-diyl.

7. A compound of claim 1 of the formula $$R^1—(A^1)_m—Z^1—A—Z^2—(A^2)_n—R^2$$

wherein $R^1$ and $R^2$ are each independently, $C_{1-10}$ straight chain alkyl or $C_{1-10}$ branched alkyl of only one chain branching, in each of which one or two $CH_2$ groups is optionally replaced by 0 atoms; or —O—COR;

$A^1$ and $A^2$ are each independently 1,4-phenylene, which is unsubstituted or substituted by 1-4 F atoms; or 1,4-cyclohexylene;

A is 1,4-cyclohexylene which is additionally substituted in the 1-position or in the 4-position by CN;

$Z^1$ and $Z^2$ are each independently —CO—O—, —O—CO—, —$CH_2CH_2$—, —$OCH_2$—, —$CH_2O$— or a single bond;

R is alkyl of 1–5 C atoms;

m is 1 or 2 and n is 0 or 1, wherein when m is 2, the two $A^1$ groups are identical or different from one another.

8. A compound of claim 7 of the formula $$R^1—A^1—Z^1—A—Z^2—R^2.$$

9. A compound of claim 7 of the formula $$R^1—A^1—Z^1—A—Z^2—A^2—R^2.$$

10. A compound of claim 7 of the formula $$R^1—(A^1)_2—Z^1—A—Z^2—R^2.$$

11. A compound of claim 7 of the formula $$R^1—(A^1)_2—Z^1—A—Z^2—A^2—R^2.$$

12. A compound of claim 7 of the formula $$R^1—Phe—Z^1—A—Z^2—R^2 \text{ or}$$

$$R^1—Cy—Z^1—A—Z^2—R^2$$

wherein Phe is 1,4-phenylene, and Cy is 1,4-cyclohexylene.

13. A compound of claim 7 of the formula $$R^1—Phe—Z^1—A—Z^2—R^2 \text{ or}$$

$$R^1—Cy—Z^1—A—Z^2—R^2$$

wherein Phe is 1,4-phenylene, and Cy is 1,4-cyclohexylene.

14. A compound of claim 7 of the formula

R¹—Phe—Z¹—A—Z²—Phe—R²

R¹—Cy—Z¹—A—Z²—Phe—R²

R¹—Cy—Z¹—A—Z²—Cy—R²

R¹—Phe—Phe—Z¹—A—Z²—R²

R¹—Phe—Cy—Z¹—A—Z²—R²

R¹—Cy—Phe—Z¹—A—Z₂—R₂

R¹—Cy—Cy—Z¹—A—Z²—R²

R¹—Phe—Phe—Z¹—A—Z²—Phe—R²

R¹—Phe—Phe—Z¹—A—Z²—Cy—R²

R¹—Phe—Cy—Z¹—A—Z²—Phe—R²

R¹—Phe—Cy—Z¹—A—Z²—Cy—R²

R¹—Cy—Phe—Z¹—A—Z²—Phe—R²

R¹—Cy—Phe—Z¹—A—Z²—Cy—R²

R¹—Cy—Cy—Z¹—A—Z²—Phe—R² or

Rhu 1—Cy—Cy—Z¹—A—Z²—Cy—R² wherein Phe is 1,4-phenylene, and Cy is 1,4-cyclohexylene.

15. A compound of claim 7 wherein R¹ and R², independently, are each alkyl or oxa-containing alkyl.

16. A compound of claim 7 wherein A¹ and A², independently, are each 1,4-cyclohexylene or 1,4-phenylene.

17. A compound of claim 7 wherein Z¹ and Z² are each single bonds.

18. A compound of claim 7 wherein m is 1 and n is 0.

19. A compound of claim 7 of the formula

R¹—A¹—Z¹—A—R²

R¹—Phe—A—R²

R¹—Phe—CO—O—A—R²

R¹—Phe—O—CO—A—R²

R¹—Phe—CH₂CH₂—A—R²

R¹—Phe—O—CH₂—A—R²

R¹—Phe—CH₂—O—A—R²

R¹—Cy—A—R²

R¹—Cy—CO—O—A—R²

R¹—Cy—O—CO—A—R²

R¹—Cy—CH₂—CH₂—A—R²

R¹—Cy—O—CH₂—A—R²

R¹—Cy—CH₂—O—A—R² or

R¹—Phe—Phe—A—R² wherein Phe is 1,4-phenylene, and Cy is 1,4-cyclohexylene.

20. A compound of claim 7 wherein the groups R¹—(A¹)$_m$—Z¹— and —Z²—(A²)$_n$—R² are in the trans-position in relation to one another, and the 1-substitutent on A is in the cis-position in relation to the group 21. r-1-cyano-1-pentyl-cis-4-(trans-4-pentylcyclohexyl)-cyclohexane, a compound of claim 7.

22. A compound of claim 7 of the formula

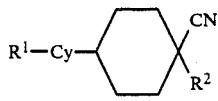

wherein R¹ is alkyl of 2-7 C atoms, R² is alkyl of 2-10 C atoms, or alkyl of 2-10 C atoms wherein one CH₂ group is replaced by an oxygen atom and Cy is 1,4-cyclohexylene.

23. A compound of claim 22 which is
(a) r-1-cyano-1-ethyl-cis-4-(trans-4-ethylcyclohexyl)-cyclohexane,
(b) r-1-cyano-1-ethyl-cis-4-(trans-4-heptylcyclohexyl)-cyclohexane,
(c) r-1-cyano-1-propyl-cis-4-(trans-4-propylcyclohexyl)-cyclohexane,
(d) r-1-cyano-1-propyl-cis-4-(trans-4-butylcyclohexyl)-cyclohexane,
(e) r-1-cyano-1-propyl-cis-4-(trans-4-pentylcyclohexyl)-cyclohexane,
(f) r-1-cyano-1-propyl-cis-4-(trans-4-heptylcyclohexyl)-cyclohexane,
(g) r-1-cyano-1-isopropyl-cis-4-(trans-4-heptylcyclohexyl)cyclohexane,
(h) r-1-cyano-1-butyl-cis-4-(trans-4-propylcyclohexyl)-cyclohexane,
(i) r-1-cyano-1-butyl-cis-4-(trans-4-butylcyclohexyl)-cyclohexane,
(j) r-1-cyano-1-pentyl-cis-4-(trans-4-propylcyclohexyl)-cyclohexane,
(k) r-1-cyano-1-pentyl-cis-4-(trans-4-butylcyclohexyl)-cyclohexane,
(l) r-1-cyano-1-pentyl-cis-4-(trans-4-pentylcyclohexyl)-cyclohexane,
(m) r-1-cyano-1-pentyl-cis-4-(trans-4-heptylcyclohexyl)-cyclohexane,
(n) r-1-cyano-1-hexyl-cis-4-(trans-4-propylcyclohexyl)-cyclohexane,
(o) r-1-cyano-1-hexyl-cis-4-(trans-4-butylcyclohexyl)-cyclohexane,
(p) r-1-cyano-1-heptyl-cis-4-(trans-4-propylcyclohexyl)-cyclohexane,
(q) r-1-cyano-1-heptyl-cis-4-(trans-4-butylcyclohexyl)-cyclohexane,
(r) r-1-cyano-1-heptyl-cis-4-(trans-4-pentylcyclohexyl)-cyclohexane,
(s) r-1-cyano-1-octyl-cis-4-(trans-4-propylcyclohexyl)-cyclohexane,
(t) r-1-cyano-1-nonyl-cis-4-(trans-4-propylcyclohexyl)-cyclohexane,
(u) r-1-cyano-1-decyl-cis-4-(trans-4-propylcyclohexyl)-cyclohexane,
(v) r-1-cyano-1-ethoxymethyl-cis-4-(trans-4-pentylcyclohexyl)cyclohexane.

24. A compound of claim 7 of the formula

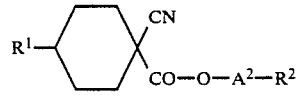

wherein R¹ is alkyl of 2-7 C atoms, A² is 1,4-cyclohexylene or 1,4-phenylene and R² is alkyl of 2-10 C atoms.

25. A compound of claim 24 which is
(a) trans-4-propylcyclohexyl 1-cyano-trans-4-pentylcyclohexane-r-1-carboxylate,
(b) trans-4-butylcyclohexyl 1-cyano-trans-4-pentylcyclohexane-r-1-carboxylate,
(c) trans-4-pentylcyclohexyl 1-cyano-trans-4-pentylcyclohexane-r-1-carboxylate,
(d) trans-4-hexylcyclohexyl 1-cyano-trans-4-pentylcyclohexane-r-1-carboxylate, or
(e) p-propylphenyl 1-cyano-trans-4-pentyl-cyclohexane-r-1-carboxylate.

26. A compound, of claim 1 of the formula $$R^{1'}-A-Z^0-(A^{1'}-Z')_m-(A^{2'})_n-R^{2'}$$

wherein
R$^{1'}$ and R$^{2'}$ are each C$_{1-10}$-alkyl; C$_{1-10}$-alkyl wherein one or two non-adjacent CH$_2$ groups are replaced by 0 atoms or —CH=CH—, the maximum number of C-atoms still being 15; F; Cl,; Br; CN; —COOR; —O—COR; or —C≡C—R$^{340}$,
A$^{1'}$ and A$^{2'}$ are each 1,4-cyclohexylene, 1,3-dioxane-2,5-diyl, 1,4-phenylene, pyridazine-3,6-diyl or pyrimidine-2,5-diyl, or one of the last three groups C-substituted by one or two of F, Cl, CH$_3$, or CN,
A is 1,4-cyclohexylene substituted in the 1- or 4-position by CN,
Z$^0$ and Z$^{1'}$ are each —CO—O—, —O—CO—, —CH$_2$—CH$_2$—, —OCH$_2$, —CH$_2$—O— or a single bond,
R$^{3'}$ is alkyl of 1–7 C atoms,
R is alkyl of 1–10 C atoms and
m and n are each independently 1 or 2, and
wherein (m+n)≧3, or, when Z$^0$ is a single bond and Z$^{1'}$ is not a single bond, ≧2 and when m=2 or n=2, all groups A$^{1'}$, A$^{2'}$ and Z$^{1'}$ which are present are identical or different.

27. A compound of claim 26 of the formula $$R^{1'}-A-A^{1'}-Z^{1'}-A^{2'}-R^{2'}$$

$$R^{1'}-A-(A^{1'})_2-A^{2'}-R^{2'}$$

$$R^{1'}-A-A^{1'}-Z^{1'}-(A^{2'})_2-R^{2'}$$

$$R^{1'}-A-(A^{1'})_2-Z^{1'}-A^{2'}-R^{2'}$$

$$R^{1'}-A-Z^0-(A^{1'})_2-A^{2'}-R^{2'}$$

$$R^{1'}-A-Z^0-(A^{1'})_2-Z^{1'}-A^{2'}-R^{2'}$$

$$R^{1'}-A-(A^{1'}-Z^{1'})_2-A^{2'}-R^{2'}$$

$$R^{1'}-A-(A^{1'})_2-(A^{2'})_2-R^{2'} \text{ or}$$

$$R^{1'}-A-(A^{1'})_2-Z^{1'}-(A^{2'})_2-R^{2'}$$

28. A compound, of claim 26 of the formula $$R^{1'}-A-Pyr-Z^{1'}-Cy-R^{2'}$$

$$R^{1'}-A-Pyr-Z^{1'}-Phe-R^{2'}$$

$$R^{1'}-A-Pyn-Z^{1'}-Phe-R^{2'}$$

$$R^{1'}-A-Pyn-Z^{1'}-Cy-R^{2'}$$

$$R^{1'}-A-Phe-Phe-Cy-R^{2'}$$

$$R^{1'}-A-Phe-Phe-Dio-R^{2'}$$

$$R^{1'}-A-Cy-Phe-Phe-R^{2'}$$

$$R^{1'}-A-Cy-Phe-Cy-R^{2'}$$

$$R^{1'}-A-Cy-Phe-Dio-R^{2'}$$

$$R^{1'}-A-Phe-Cy-Cy-R^{2'}$$

$$R^{1'}-A-Phe-Cy-Dio-R^{2'}$$

$$R^{1'}-A-Phe-Pyr-Cy-R^{2'}$$

$$R^{1'}-A-Phe-Pyn-Cy-R^{2'}$$

$$R^{1'}-A-Pyr-Phe-Cy-R^{2'}$$

$$R^{1'}-A-Pyn-Phe-Cy-R^{2'}$$

$$R^{1'}-A-Pyn-Phe-Dio-R^{2'}$$

$$R^{1'}-A-Phe-Z^{1'}-Phe-R^{2'}$$

$$R^{1'}-A-Phe-Z^{1'}-Cy-R^{2'}$$

$$R^{1'}-A-Cy-Z^{1'}-Cy-R^{2'}$$

$$R^{1'}-A-Cy-Z^{1'}-Phe-R^{2'}$$

$$R^{1'}-A-Pyr-Z^{1'}-Phe-R^{2'}$$

$$R^{1'}-A-Pyr-Z^{1'}-Cy-R^{2'}$$

$$R^{1'}-A-Cy-Z^{1'}-Dio-R^{2'}$$

$$R^{1'}-A-Cy-Z^{1'}-Pyr-R^{2'}$$

$$R^{1'}-A-Cy-Z^{1'}-Pyn-R^{2'}$$

$$R^{1'}-A-Phe-Z^{1'}-Dio-R^{2'}$$

$$R^{1'}-A-Phe-Z^{1'}-Pyn-R^{2'}$$

$$R^{1'}-A-Dio-Z^{1'}-Phe-R^{2'}$$

$$R^{1'}-A-Dio-Z^{1'}-Cy-R^{2'}$$

$$R^{1'}-A-Phe-Phe-Z^{1'}-Cy-R^{2'}$$

$$R^{1'}-A-Phe-Phe-Z^{1'}-Dio-R^{2'}$$

$$R^{1'}-A-Phe-Phe-Z^{1'}-Phe-R^{2'}$$

$$R^{1'}-A-Cy-Phe-Z^{1'}-Cy-R^{2'}$$

$$R^{1'}-A-Cy-Phe-Z^{1'}-Phe-R^{2'}$$

$$R^{1'}-A-Cy-Cy-Zhu\ 1'-Phe-R^{2'}$$

$$R^{1'}-A-Cy-Cy-Z^{1'}-Cy-R^{2'}$$

$$R^{1'}-A-Cy-Phe-Z^{1'}-Dio-R^{2'}$$

$$R^{1'}-A-Z^0-Phe-Phe-Cy-R^{2'}$$

$$R^{1'}-A-Z^0-Cy-Phe-Phe-R^{2'}$$

$$R^{1'}-A-Z^0-Cy-Phe-Cy-R^{2'}$$

$$R^{1'}-A-Z^0-Phe-Phe-Dio-R^{2'}$$

$$R^{1'}-A-Z^0-Cy-Cy-Phe-R^{2'}$$

$$R^{1'}-A-Z^0-Phe-Cy-Cy-R^{2'}$$

$$R^{1'}-A-Z^0-Dio-Cy-Phe-R^{2'} \text{ or}$$

$$R^{1'}-A-Z^0-Phe-Cy-Dio-R^{2'}$$

wherein Phe is 1,4-phenylene, Cy is 1,4-cyclohexylene, Dio is 1,3-dioxane-2,5-diyl, Pyn is pyridazine-3,6-diyl and Pyr is pyrimidine-2,5-diyl.

29. A compound of claim 1 of the formula $$Alkyl-A^1-Z^1-A-Alkyl$$

$$Alkoxy-A^1-Z^1-A-Alkyl$$

$$Alkyl-Phe-Z^1-A-Alkyl$$

Alkyl—Phe—A—Alkyl

Alkoxy—Phe—A—Alkyl

Alkyl—Phe—CO—O—A—Alkyl

Alkoxy—Phe—CO—O—A—Alkyl

Alkyl—Phe—O—CO—A—Alkyl

Alkoxy—Phe—O—CO—A—Alkyl

Alkoxy—Phe—CH$_2$CH$_2$—A—Alkyl

Alkoxy—Phe—CH$_2$CH$_2$—A—Alkyl

Alkyl—Phe—Phe—CH$_2$CH$_2$—A—Alkyl

Alkoxy—Phe—Phe—CH$_2$CH$_2$—A—Alkyl

Alkyl—Phe—O—CH$_2$—A—Alkyl

Alkoxy—Phe—O—CH$_2$—A—Alkyl

Alkyl—Phe—CH$_2$—O—A—Alkyl

Alkoxy—Phe—CH$_2$—O—A—Alkyl

Alkyl—Cy—Zl—A—Alkyl

Alkyl—Cy—A—Alkyl

Alkyl—Cy—CO—O—A—Alkyl

Alkyl—Cy—O—CO—A—Alkyl

Alkyl—Cy—CH$_2$CH$_2$—A—Alkyl

Alkyl—Cy—O—CH$_2$—A—Alkyl

Alkyl—Cy—CH$_2$—O—A—Alkyl

Alkyl—Dio—A-Alkyl

Alkyl—Pyr—A—Alkyl

Alkoxy—Pyr—A—Alkyl

Alkyl—Pyn—A—Alkyl

Alkyl—Phe—Phe—A—Alkyl

Alkoxy—Phe—Phe—A—Alkyl

Alkyl—Phe—Cy—A—Alkyl

Alkoxy—Phe—Cy—A—Alkyl

Alkyl—Phe—A—Cy—Alkyl

Alkyl—Cy—Cy—A—Alkyl

Alkoxy—Cy—Cy—A—Alkyl

Alkyl—Cy—Phe—A—Alkyl

Alkyl—Cy—Cy—CO—O—A—Alkyl

Alkyl—Cy—Cy—O—CO—A—Alkyl

Alkyl—Dio—Phe—CO—O—A—Alkyl

Alkyl—Dio—Phe—O—CO—A—Alkyl

Alkyl—Cy—Phe—CH$_2$CH$_2$—A—Alkyl

Alkyl—Cy—Cy—CH$_2$CH$_2$—A—Alkyl

Alkyl—Dio—Phe—CH$_2$CH$_2$—A—Alkyl

Alkyl—Phe—Phe—CO—O—A—Alkyl

Alkoxy—Phe—Phe—CO—O—A—Alkyl

Alkyl—Phe—Phe—O—CO—A—Alkyl or

Alkoxy—Phe—Phe—O—CO—A—Alkyl wherein Phe is 1,4-phenylene, Cy is 1,4-cyclohexylene, Dio is 1,3-dioxane-2,5-diyl, Pyn is pyridazine-3,6-diyl and Pyr is pyrimidine-2,5-diyl.

30. A phase of claim 26 wherein said cyclohexane derivative is of the formula

Alkyl—A—Phe—Phe—Cy—Alkyl

Alkyl—A—Phe—Phe—Dio—Alkyl

Alkyl—A—Phe—Phe—Dio—Alkoxy

Alkyl—A—Cy—Phe—Phe—Alkyl

Alkyl—A—Cy—Phe—Phe—Alkoxy

Alkyl—A—Cy—Phe—Phe—CN

Alkyl—A—Phe—CH$_2$CH$_2$—Phe—Alkyl

Alkyl—A—Phe—CH$_2$CH$_2$—Phe—Alkoxy

Alkyl—A—Phe—CH$_2$CH$_2$—Phe—CN

Alkyl—A—phe—CH$_2$CH$_2$—Cy—Alkyl

Alkyl—A—Cy—CH$_2$CH$_2$—Cy—Alkyl

Alkyl—A—Cy—CH$_2$CH$_2$—Phe—Alkyl

Alkyl—A—Cy—CH$_2$CH$_2$—Phe—Alkoxy

Alkyl—A—Phe—COO—Phe—CN

Alkyl—A—Phe—COO—Phe—Alkyl

Alkyl—A—Phe—COO—Phe—Alkoxy

Alkyl—A—Phe—COO—Phe—CN

Alkyl—A—Phe—OCO—Phe—Alkyl

Alkyl—A—Phe—OCO—Phe—Alkoxy

Alkyl—A—Phe—OCO—Phe—CN

Alkyl—A—Phe—COO—Cy—Alkyl

Alkyl—A—Phe—OCO—Cy—Alkyl

Alkyl—A—CH$_2$CH$_2$—Phe—Phe—Cy—Alkyl or

Alkyl—A—Phe—Phe—CH$_2$CH$_2$—Cy—Alkyl wherein Phe is 1,4-phenylene, Cy is 1,4-cyclohexylene and Dio is 1,3-dioxane-2,5-diyl.

31. A compound of claim 26 of the formula

32. A compound of claim 26 of the formula
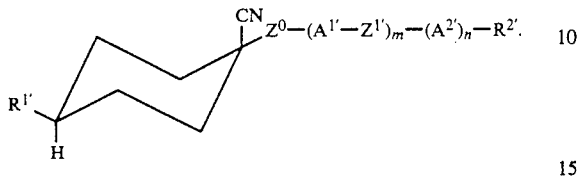
33. A compound of claim 1, wherein A is
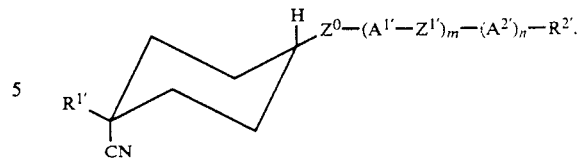
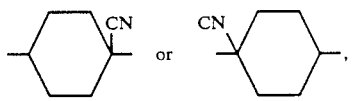
wherein the substituents in the 1- and 4-positions are in the trans-position relative to one another, while the CN group is in the position cis to the opposite group.
* * * * *

UNITED STATES PATENT AND TRADEMARK OFFICE
CERTIFICATE OF CORRECTION

PATENT NO. : 4,985,583
DATED : January 15, 1991
INVENTOR(S) : Rudolf Eidenschink et al It is certified that error appears in the above-identified patent and that said Letters Patent is hereby corrected as shown below:

On the title page item [75] Inventors: please add the following named inventors:

--Günther Haas, Neckargemünd, Fed. Rep. of Germany

Ludwig Pohl, Darmstadt, Fed. Rep. of Germany

Michael Römer, Rodgau, Fed. Rep. of Germany--

Signed and Sealed this

Sixteenth Day of June, 1992

*Attest:*

DOUGLAS B. COMER

*Attesting Officer*     *Acting Commissioner of Patents and Trademarks*